(12) United States Patent
Olsen et al.

(10) Patent No.: US 10,220,171 B2
(45) Date of Patent: Mar. 5, 2019

(54) INTERFACE COMPRISING A ROLLING NASAL BRIDGE PORTION

(75) Inventors: Gregory James Olsen, Auckland (NZ); Peter David Alexander Bearne, Auckland (NZ); Leon Edward Evans, Auckland (NZ); Matthew Roger Stephenson, Auckland (NZ); Craig Robert Prentice, Auckland (NZ); Bernard Tsz Lun Ip, Auckland (NZ); Tony William Spear, Auckland (NZ); Mark Arvind McLaren, Auckland (NZ); Roheet Patel, Auckland (NZ); Brad Michael Howarth, Auckland (NZ); Jonathan David Harwood, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 469 days.

(21) Appl. No.: 14/111,739

(22) PCT Filed: Apr. 13, 2012

(86) PCT No.: PCT/IB2012/000858
§ 371 (c)(1),
(2), (4) Date: Oct. 14, 2013

(87) PCT Pub. No.: WO2012/140514
PCT Pub. Date: Oct. 18, 2012

(65) Prior Publication Data
US 2014/0096774 A1 Apr. 10, 2014

Related U.S. Application Data

(60) Provisional application No. 61/476,188, filed on Apr. 15, 2011, provisional application No. 61/504,295, (Continued)

(51) Int. Cl.
*A61M 16/00* (2006.01)
*A62B 9/00* (2006.01)
(Continued)

(52) U.S. Cl.
CPC ........ *A61M 16/0057* (2013.01); *A61M 16/06* (2013.01); *A61M 16/0611* (2014.02);
(Continued)

(58) Field of Classification Search
CPC .................. A61M 16/00–16/0096; A61M 16/08–16/0891; A61M 16/16–16/168;
(Continued)

(56) References Cited

U.S. PATENT DOCUMENTS 2,376,871 A 5/1945 Fink
2,706,983 A 4/1955 Matheson et al.
(Continued)

FOREIGN PATENT DOCUMENTS

AU 744593 2/2002
AU 2003257274 3/2004
(Continued)

OTHER PUBLICATIONS

International Search Report; PCT/IB2012/000858; dated Jul. 30, 2012; 7 pages.
(Continued)

*Primary Examiner* — Gregory Anderson
*Assistant Examiner* — Ned T Heffner
(74) *Attorney, Agent, or Firm* — Knobbe, Martens, Olson & Bear, LLP

(57) ABSTRACT

An interface for positive pressure therapy includes a mask assembly, a headgear assembly and a connection port assembly. The mask assembly comprises a seal member that has an upper portion movably connected to an integrated lower portion, wherein the upper portion rolls during hinging
(Continued)

movement of the upper portion relative to the lower portion. The headgear assembly allows connection to the mask assembly in a direction substantially normal to a direction of strap tension. The connection port assembly includes a swivel elbow with a valve member that controls flow through a port that opens toward the user.

28 Claims, 64 Drawing Sheets

Related U.S. Application Data filed on Jul. 4, 2011, provisional application No. 61/553,067, filed on Oct. 28, 2011.

(51) Int. Cl.
*A61M 16/06* (2006.01)
*A61M 16/08* (2006.01)

(52) U.S. Cl.
CPC .... *A61M 16/0616* (2014.02); *A61M 16/0683* (2013.01); *A61M 16/0816* (2013.01); *A61M 16/0825* (2014.02); *A61M 16/0875* (2013.01); *A61M 2205/584* (2013.01)

(58) Field of Classification Search
CPC .... A61M 16/20; A61M 16/208; A61M 11/00; A61M 11/001; A61M 11/02; A61M 11/04; A61M 11/041–11/048; A61M 39/00; A61M 39/10; F24F 6/00; F16L 11/00–11/26; F16L 27/00; F16L 31/00; F16L 39/00; F16L 41/00; E21B 21/02
USPC ............ 128/205.24, 207.12, 207.16, 201.28, 128/203.11
See application file for complete search history.

(56) References Cited

U.S. PATENT DOCUMENTS

| | | | |
|---|---|---|---|
| 2,858,828 A | 11/1958 | Matheson | |
| 2,874,693 A | 2/1959 | Matheson | |
| 2,881,444 A | 4/1959 | Fresh et al. | |
| 2,893,387 A | 7/1959 | Gongoll et al. | |
| 2,939,458 A | 6/1960 | Lundquist | |
| 2,999,498 A | 9/1961 | Matheson | |
| 3,037,501 A | 6/1962 | Miller | |
| 4,069,516 A | 1/1978 | Watkins, Jr. | |
| 4,739,755 A | 4/1988 | White et al. | |
| 5,074,297 A | 12/1991 | Venegas | |
| 5,349,949 A | 9/1994 | Schegerin | |
| 5,353,789 A | 10/1994 | Schlobohm | |
| 5,355,878 A | 10/1994 | Griffiths et al. | |
| 5,438,981 A | 8/1995 | Starr et al. | |
| 5,540,223 A | 7/1996 | Starr et al. | |
| 5,647,355 A | 7/1997 | Starr et al. | |
| 5,746,201 A | 5/1998 | Kidd | |
| 5,842,470 A | 12/1998 | Ruben | |
| 5,878,743 A | 3/1999 | Zdrojkowski et al. | |
| 5,896,857 A | 4/1999 | Hely et al. | |
| 5,921,239 A | 7/1999 | McCall et al. | |
| 5,937,851 A * | 8/1999 | Serowski | A61M 16/06 128/202.27 |
| 6,006,748 A | 12/1999 | Hollis | |
| 6,016,804 A | 1/2000 | Gleason et al. | |
| 6,050,294 A | 4/2000 | Makowan | |
| 6,355,878 B1 | 3/2002 | Kim | |
| 6,467,483 B1 | 10/2002 | Kopacko et al. | |
| 6,491,034 B1 | 12/2002 | Gunaratnam et al. | |
| 6,557,555 B1 | 5/2003 | Hollis | |
| 6,634,357 B1 | 10/2003 | Hamilton | |
| 6,644,316 B2 | 11/2003 | Bowman et al. | |
| 6,651,663 B2 | 11/2003 | Barnett et al. | |
| 6,691,707 B1 | 2/2004 | Gunaratnam et al. | |
| 6,729,333 B2 | 5/2004 | Barnett et al. | |
| 6,851,425 B2 * | 2/2005 | Jaffre | A61M 16/08 128/204.18 |
| 6,851,428 B2 | 2/2005 | Dennis | |
| 6,889,692 B2 | 5/2005 | Hollis | |
| 7,066,178 B2 * | 6/2006 | Gunaratnam | A61M 16/06 128/206.21 |
| 7,089,939 B2 | 8/2006 | Walker et al. | |
| 7,174,893 B2 | 2/2007 | Walker et al. | |
| 7,185,652 B2 | 3/2007 | Gunaratnam et al. | |
| D582,546 S | 12/2008 | Fujiura et al. | |
| 7,523,754 B2 | 4/2009 | Lithgow et al. | |
| 7,568,482 B2 | 8/2009 | Jaffre et al. | |
| 7,597,100 B2 | 10/2009 | Ging et al. | |
| 7,665,464 B2 | 2/2010 | Kopacko et al. | |
| 7,779,832 B1 | 8/2010 | Ho | |
| 7,827,990 B1 | 11/2010 | Melidis et al. | |
| 8,342,181 B2 | 1/2013 | Selvarajan et al. | |
| 8,517,024 B2 | 8/2013 | Selvarajan et al. | |
| 8,596,276 B2 | 12/2013 | Omura et al. | |
| 9,132,256 B2 | 9/2015 | Gunaratnam et al. | |
| 2002/0029780 A1 | 3/2002 | Frater | |
| 2003/0127101 A1 | 7/2003 | Dennis | |
| 2003/0196658 A1 | 10/2003 | Ging et al. | |
| 2004/0094157 A1 | 5/2004 | Dantanarayana et al. | |
| 2004/0118406 A1 * | 6/2004 | Lithgow | A61M 16/06 128/206.24 |
| 2006/0130844 A1 | 6/2006 | Ho et al. | |
| 2006/0207599 A1 | 9/2006 | Busch et al. | |
| 2007/0044804 A1 | 3/2007 | Matula, Jr. et al. | |
| 2007/0125385 A1 | 6/2007 | Ho et al. | |
| 2007/0215161 A1 | 9/2007 | Frater et al. | |
| 2007/0267017 A1 | 11/2007 | McAuley et al. | |
| 2008/0110464 A1 | 5/2008 | Davidson et al. | |
| 2009/0014008 A1 | 1/2009 | Takishita et al. | |
| 2009/0065729 A1 | 3/2009 | Worboys et al. | |
| 2009/0095301 A1 | 4/2009 | Hitchcock et al. | |
| 2009/0126739 A1 | 5/2009 | Ng et al. | |
| 2009/0139526 A1 | 6/2009 | Melidis et al. | |
| 2009/0139527 A1 | 6/2009 | Ng et al. | |
| 2009/0178679 A1 | 7/2009 | Lithgow et al. | |
| 2009/0188505 A1 | 7/2009 | Smart et al. | |
| 2009/0272380 A1 | 11/2009 | Jaffre et al. | |
| 2010/0282265 A1 | 11/2010 | Melidis et al. | |
| 2010/0319700 A1 | 12/2010 | Ng et al. | |
| 2011/0048425 A1 | 3/2011 | Chang | |
| 2013/0092169 A1 | 4/2013 | Frater et al. | |
| 2013/0306066 A1 | 11/2013 | Selvarajan et al. | |
| 2015/0090266 A1 | 4/2015 | Melidis et al. | |

FOREIGN PATENT DOCUMENTS

| | | |
|---|---|---|
| DE | 196 03 949 | 8/1997 |
| DE | 19962515 | 7/2001 |
| EP | 0 303 090 | 4/1992 |
| EP | 1259279 | 11/2007 |
| FR | 1 299 470 | 6/1962 |
| GB | 309770 | 4/1929 |
| GB | 823887 | 11/1959 |
| GB | 823897 | 11/1959 |
| GB | 2 393 126 | 3/2004 |
| GB | 2393126 | 11/2004 |
| JP | 11-000397 | 1/1999 |
| JP | 2008-526393 | 7/2008 |
| NZ | 573196 | 7/2010 |
| NZ | 556198 | 10/2010 |
| NZ | 556043 | 1/2011 |
| NZ | 551715 | 2/2011 |
| WO | WO 1999/021618 | 5/1999 |
| WO | WO 2001/062326 | 8/2001 |
| WO | WO 2002/047749 | 6/2002 |
| WO | WO 2004/022146 | 3/2004 |
| WO | WO 2004/071565 | 8/2004 |
| WO | WO 2004/071565 A1 | 8/2004 |
| WO | WO 2005/068002 | 7/2005 |
| WO | WO 2005/123166 | 12/2005 |
| WO | WO 2005/123166 A1 | 12/2005 |
| WO | WO 2006/074513 | 7/2006 |

(56) References Cited

FOREIGN PATENT DOCUMENTS

| | | |
|---|---|---|
| WO | WO 2006/074515 | 7/2006 |
| WO | WO 2006/130903 | 12/2006 |
| WO | WO 2006/138416 | 12/2006 |
| WO | WO 2007/139531 | 12/2007 |
| WO | WO 2007/147088 | 12/2007 |
| WO | WO 2008/040050 | 4/2008 |
| WO | WO 2009/002608 | 12/2008 |
| WO | WO 2009/108995 | 9/2009 |
| WO | WO 2010/009877 | 1/2010 |
| WO | WO 2010/067237 | 6/2010 |
| WO | WO 2010/071453 A1 | 6/2010 |
| WO | WO 2012/020359 | 2/2012 |
| WO | WO 2012/040791 | 4/2012 |
| WO | WO 2012/140514 | 10/2012 |
| WO | WO 2015/022629 | 2/2015 |

OTHER PUBLICATIONS

Written Opinion of the ISA; PCT/IB2012/000858, dated Jul. 30, 2012; 7 pages.

* cited by examiner

INTERFACE COMPRISING A ROLLING NASAL BRIDGE PORTION

CROSS-REFERENCE TO RELATED APPLICATIONS

This application is a National Phase Application of PCT International Application Number PCT/IB2012/000858, filed Apr. 13, 2012, which claims priority to U.S. Provisional Patent Application No. 61/476,188, filed Apr. 15, 2011, U.S. Provisional Patent Application No. 61/504,295, filed Jul. 4, 2011 and U.S. Provisional Patent Application No. 61/553,067, filed Oct. 28, 2011, each of which is hereby incorporated by reference in its entirety.

BACKGROUND OF THE INVENTION

Field of the Invention

The present invention generally relates to face masks that cover at least one of a nose and a mouth of a user to supply respiratory gas under positive pressure. More particularly, certain aspects of the present invention relate to such masks that have a nasal bridge seal portion that moves relative to another seal portion of the mask.

Description of the Related Art

Face masks can be used to provide respiratory gases to a user under positive pressure. In configurations in which both a mouth and a nose of a user are covered, the full face mask typically will overlie a bridge of the nose. Generally, a single seal will circumscribe the nose and the mouth of the user.

Such full face masks commonly are secured to a head of the user with headgear. In order to sufficiently reduce leakage, the headgear typically is tightened, which results in an elevated pressure being exerted on a bridge of a user's nose. In other words, as the headgear is tightened, the silicone seal typically applies a progressively increasing load on the bridge of the nose. The pressure can be a source of discomfort and, in some circumstances, can lead to pressure sores over time.

SUMMARY OF THE INVENTION

It is an object of the present disclosure to provide one or more constructions and/or methods that will at least go some way towards improving on the above or that will at least provide the public or the medical profession with a useful choice.

Accordingly, an interface is provided for use in providing positive pressure respiratory therapy. The interface comprises a mask assembly. The mask assembly comprises a mask seal and a mask base that is removably connected to the mask seal. The mask seal comprises a mask seal clip that is more rigid than at least a portion of the mask seal. The mask seal clip is generally cup-shaped in configuration with an open proximal end and a generally closed distal end. A generally pentagonal lip extends around the proximal end. The mask seal clip comprises an arcuate upper portion with an outer surface. A mask seal clip arc length is defined along the outer surface adjacent an upper extremity of the upper portion between a pair of hinge points. A hinge axis extends laterally across the mask assembly between the hinge points and at least a portion of the upper portion of the mask seal clip is positioned vertically higher than the hinge axis. The mask seal clip upper portion comprises a support surface. A generally central passage extends through the mask clip into a chamber defined by the mask seal. The mask seal comprises a flexible upper portion that is configured to be positioned over a nasal region of a user. The mask seal upper portion is positioned vertically higher than the hinge axis. The mask seal upper portion comprises a region of reduced stiffness located between two regions of increased stiffness. The region of reduced stiffness is capable of rolling to allow pivoting of the mask seal upper portion relative to the mask seal clip. One of the two regions of increased stiffness is positioned adjacent to a small radius bend and the other of the two regions of increased stiffness is position adjacent to a reinforcing component. The small radius bend and the reinforcing component define boundaries between which the upper portion of the mask exhibits rolling during pivoting of the upper portion about the pivot axis. The mask seal upper portion has a first curve length adjacent to the small radius bend and a second curve length adjacent to the reinforcing band. The first curve length can be smaller than the second curve length. The curve length increases as a measured location moves away from the mask seal clip. The mask base overlies at least a portion of the mask seal clip. The mask base comprises a first pocket and a second pocket. The first and second pockets are positioned symmetrically relative to a center plane that substantially bisects the mask base. Each of the first pocket and the second pocket comprises a vertical dimension that is larger than a transverse dimension. The mask base also comprises a wall that defines a central opening. The wall extends into the generally central passage of the mask seal clip. A connection port assembly comprises an elbow terminating in a ball shaped member. The ball shaped member is sized and configured to be held by the wall that defines the central opening. The connection port assembly also comprises a removable swivel member. The removable swivel member is secured by a lever. The lever overlies a port. The port is selectively coverable with a flap. The flap also is capable of closing a central passage within the elbow. The port opening is in a general direction of the mask when the elbow is connected to the mask. A headgear assembly comprises a pair of upper straps and a pair of lower straps. One of the pair of upper straps and one of the pair of lower straps is connected to a first clip. Another of the pair of upper straps and another of the pair of lower straps is connected to a second clip. The first clip and the second clip are securable within the pockets of the mask base such that the clips are brought into engagement within the pockets by moving in a direction substantially normal to a strap tensile force direction.

In some configurations, the mask seal is a full face mask.

In some configurations, the mask seal clip is integrated into the mask seal such that the mask seal clip is non-separable from the mask seal.

In some configurations, the mask base is removably connected to the mask seal.

In some configurations, an outer surface of the upper portion rolls onto the support surface of the mask seal clip and the support surface defines an outer surface of the upper portion of the mask seal clip.

In some configurations, the region of reduced stiffness comprises a region of reduced thickness compared to the regions of increased stiffness.

In some configurations, the upper portion of the mask seal comprises an apex defined by a first wall and a second wall and the reinforcing component extends along at least a portion of the first wall and along at least a portion of the second wall. Preferably, the reinforcing component extends over the apex of the upper portion of the mask seal.

In some configurations, the reinforcing component ends at both ends in a location generally vertically higher than the hinge points.

A mask assembly can comprise a mask seal. The mask seal comprises an upper portion and a lower portion. The upper portion is pivotable relative to the lower portion. The upper portion comprises a region of reduced stiffness that is positioned between a first boundary and a second boundary. The first boundary is defined by a stiffness greater than that in the region of reduced stiffness. The second boundary is defined by a stiffness greater than that in the region of reduced stiffness. When the first boundary is moved toward the second boundary, the region of reduced stiffness buckles in a single direction to define a roll of material that changes in size as the first boundary continues to move toward the second boundary.

In some configurations, the region of reduced stiffness facilitates movement of the upper portion of the seal member relative to the lower portion of the seal member. Preferably, the upper portion comprises a nasal bridge portion of the mask and movement of the first boundary toward the second boundary facilitates movement of the nasal bridge portion of the mask relative to the lower portion of the mask.

In some configurations, the second boundary is positioned between the upper portion and the lower portion. Preferably, the mask further comprises a mask seal clip that has an increased rigidity relative to the mask seal and the second boundary is positioned along an end of the mask seal clip. More preferably, the roll of material overlies at least a portion of the mask seal clip.

In some configurations, the first boundary is defined along a reinforcing component. Preferably, the reinforcing component comprises a plastic band.

In some configurations, the region of reduced stiffness is defined with a reduced thickness relative to the first boundary.

In some configurations, the second boundary is defined by a corner having a small radius.

In some configurations, the roll extends over at least a portion of the mask seal.

In some configurations, the roll overlies at least a portion of the mask seal clip when the first boundary is moved fully toward the second boundary.

A mask assembly can comprise a mask seal. The mask seal comprises a nasal region and an oral region. The nasal region and the oral region are integrally formed. The nasal region is movable relative to the oral region such that forces exerted by the nasal region in multiple positions remain substantially constant while forces exerted by the oral region increase.

A mask assembly comprises a mask seal connected to a headgear assembly. The mask seal is configured to encircle a nasal bridge region and an oral region of a user. The mask seal comprises nonpleated means for applying a substantially constant force to the nasal bridge region while applying increasing forces to an oral region when the headgear assembly is tightened.

A mask assembly comprises a seal. The seal comprises a flange that engages a face of a user. The seal is removably connected to a mask base. The mask base comprises a first opening and a second opening. The first opening and the second opening receive a first clip and a second clip from an associated headgear assembly. The mask base further comprises a passageway positioned generally between the first opening and the second opening. The passageway is adapted to receive a breathing tube connector.

In some configurations, the mask assembly further comprises a mask seal clip that is connected to the mask seal and that is removably connected to the mask base. Preferably, the mask base overlies a substantial portion of the mask seal clip. More preferably, the mask base comprises a peripheral edge and at least one recess is defined along the peripheral edge of the mask base at a location that overlies the mask seal clip.

A mask assembly comprises a mask seal. The mask seal comprises a proximal flange adapted to contact a face of a user. The mask seal comprises a distal facing surface. A mask base comprises a peripheral edge and a cover surface extends from the peripheral edge. The mask base cover surface overlies at least a portion of the distal facing surface of the mask seal such that the mask base cover surface is spaced apart in a distal direction from the mask seal distal facing surface whereby the mask base cover surface and the mask seal distal facing surface provide an insulating effect to the mask assembly that reduces humidity rainout.

A headgear assembly is configured to secure a mask assembly to a user's head. The headgear assembly comprises a strap assembly. The strap assembly comprises a rear, upper and lower arms, and at least one crown arm. The upper and lower arms define arcuate regions shaped to at least partially encircle a user's ears. A soft edging is attached to at least a portion of a periphery of the strap assembly.

In some configurations, the strap assembly comprises a semi-rigid strap and the soft edging is butt-joined to the semi-rigid strap without overlapping the semi-rigid strap. In some configurations, the semi-rigid strap comprises a first thickness and the soft edging comprising a second thickness with the first thickness and the second thickness being substantially the same. In some configurations, the semi-rigid strap comprising a thickness and the soft edging is thinner than the thickness in at least one region. In some configurations, the semi-rigid strap comprises a thickness and the soft edging is thicker than the thickness in at least one region. In some configurations, the soft edging forms a bulbous end to the semi-rigid strap.

A clip assembly is configured to secure headgear to a mask assembly. The clip assembly comprises an outer cover and an inner catch. The inner catch is configured to attach to the outer cover thereby holding onto one or more straps from a headgear assembly. The inner catch comprises an elongated slot and a circular opening. The elongated slot can extend along an elongate axis and can have a width transverse to the elongate axis. The circular opening can have a diameter larger than the width. The elongate axis extends along a direction transverse to the straps when attached to the outer cover and the inner catch.

An elbow assembly is configured to connect a mask assembly to an air conduit. The elbow assembly comprises an elbow. The elbow comprises inner and outer walls and defines an air flow channel therebetween. The inner wall comprises a port on a side of the elbow. A sleeve is coupled with the elbow. The sleeve comprises a flap. When the flap is at a first position, the flap at least partially blocks the port and allows gas from the air conduit to pass to a user via the elbow and, when the flap is at a second position, the flap at least partially blocks the air conduit thereby allowing gas to flow from the user to a location outside of the sleeve via the port and air flow channel. The air flow channel can direct air away from the side of the elbow.

In some configurations, the air flow channel comprises two air flow channels. In some configurations, the sleeve further comprises a bump extending around an outer surface of the sleeve and a recess adjacent to the bump. In some arrangements, the bump and the recess are adapted to receive a swiveling component incorporating a ridge to engage with the bump.

BRIEF DESCRIPTION OF THE DRAWINGS

These and other features, aspects and advantages of embodiments of the present invention will be described with reference to the following drawings.

DETAILED DESCRIPTION OF THE PREFERRED EMBODIMENT

Figure 1:
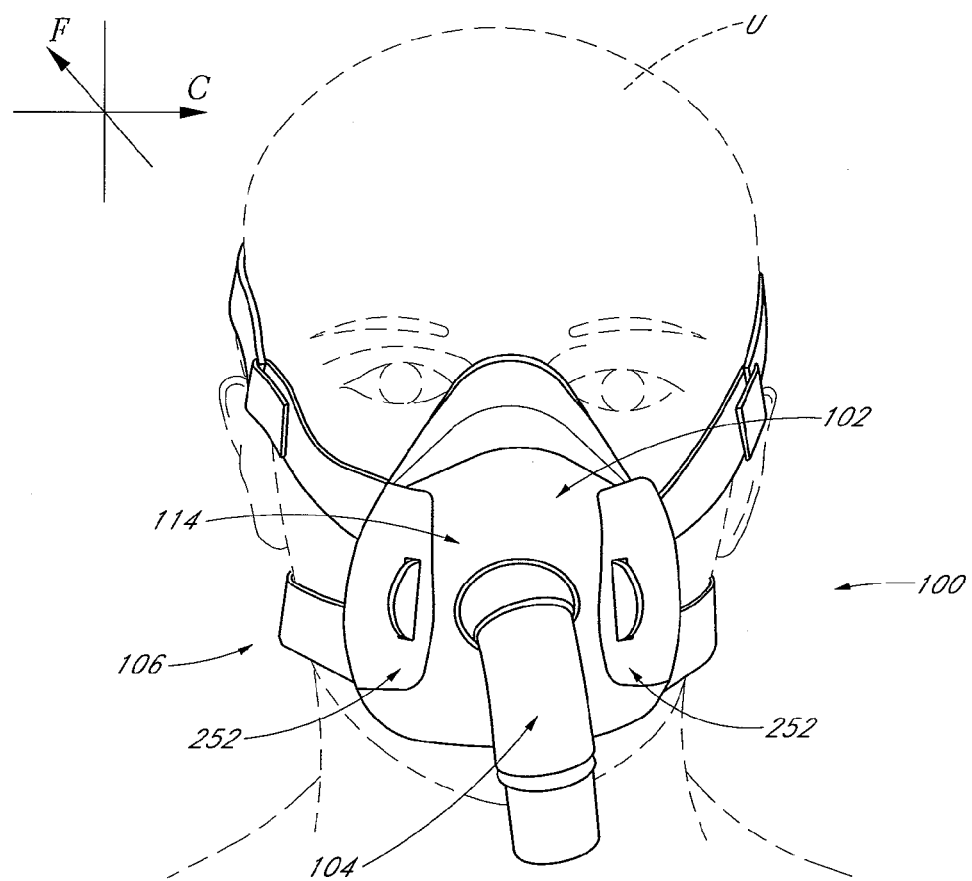
FIG. 1 is front view of a user wearing an interface that is arranged and configured in accordance with certain features, aspects and advantages of the present invention.
Figure 2:
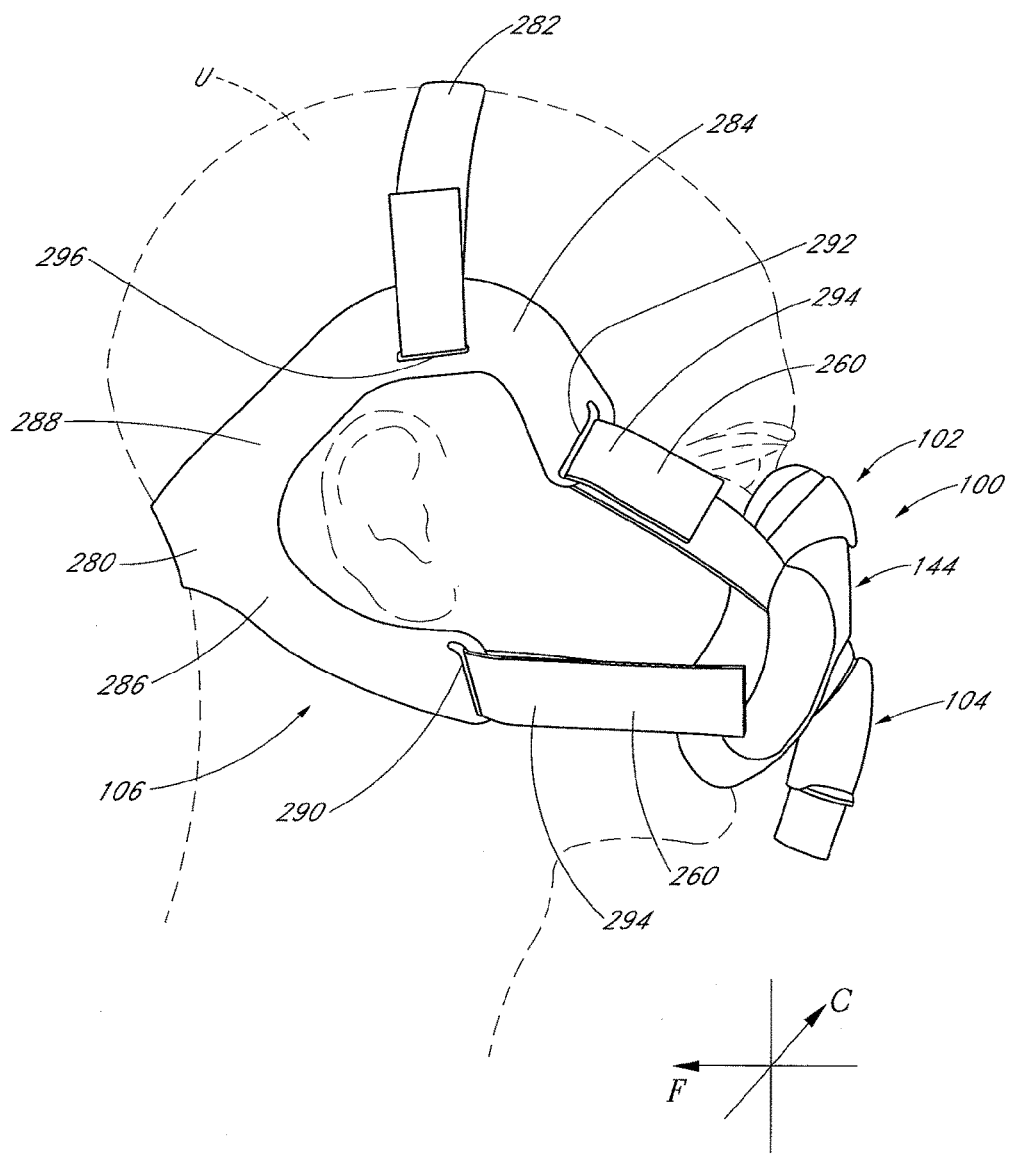
FIG. 2 is a side view of a user wearing the interface of FIG. 1.

With reference initially to FIGS. 1 and 2, an interface 100 is shown in position on a user U. The interface 100 comprises an interface that can be used in the field of respiratory therapy. The interface 100 has particular utility with forms of positive pressure respiratory therapy. For example, the interface 100 can be used for administering continuous positive airway pressure ("CPAP") treatments. In addition, the interface 100 can be used with variable positive airway pressure ("VPAP") treatments and bi-level positive airway pressure ("BiPAP") treatments. The interface can be used with any suitable CPAP system.

The interface 100 can comprise any suitable mask configuration. For example, certain features, aspects and advantages of the present invention can find utility with nasal masks, full face masks, oronasal masks or any other positive pressure mask. The illustrated mask is a full face mask. The illustrated interface 100 generally comprises a mask assembly 102, a connection port assembly 104 and a headgear assembly 106.

Figure 13:
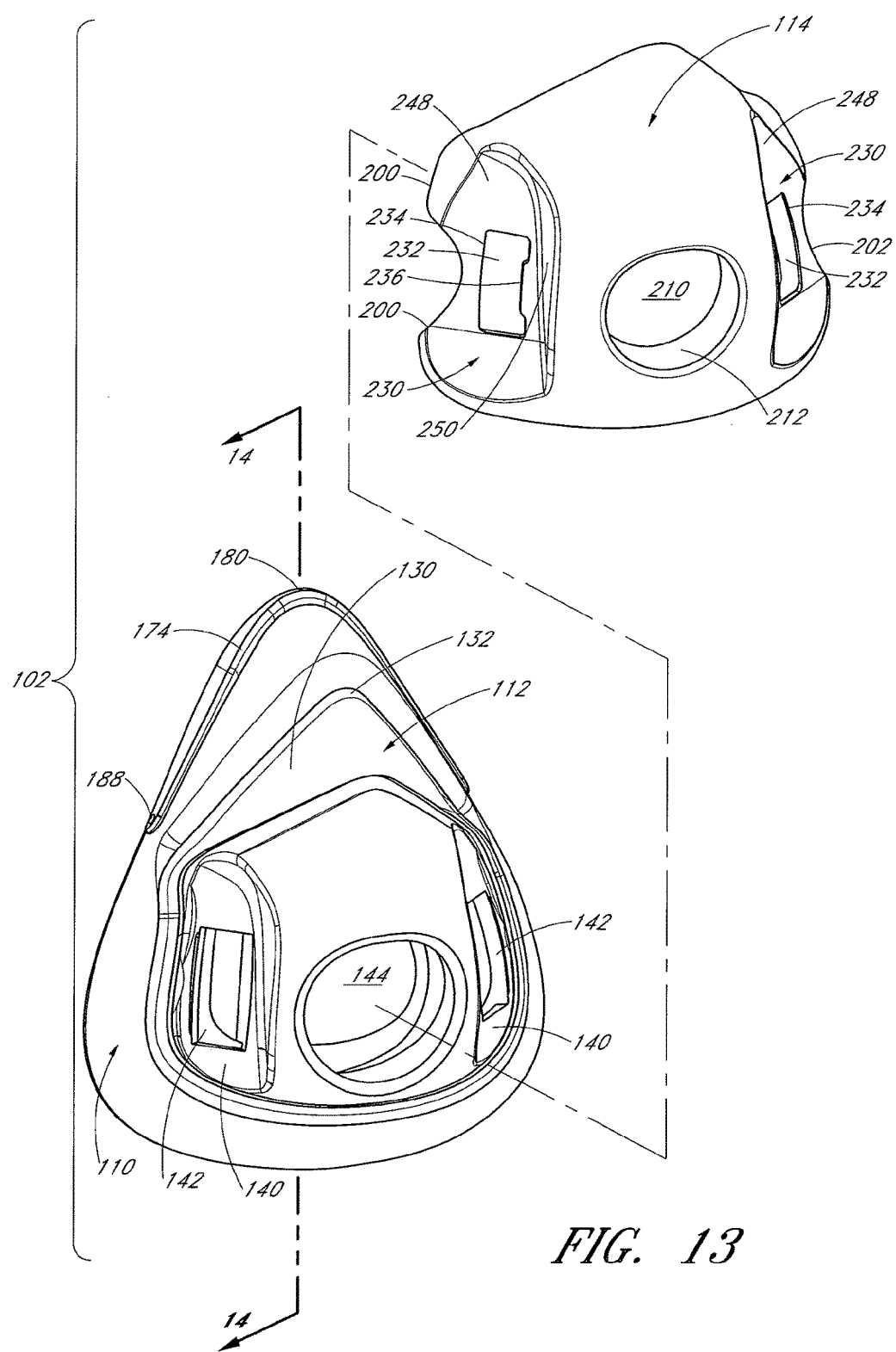
FIG. 13 is a front perspective view of the mask seal, mask seal clip and mask base of the interface of FIG. 1.

With reference to FIG. 13, the mask assembly 102 generally comprises a mask seal 110, which can include a mask seal clip 112, and a mask base 114. As will be described, the mask seal clip 112 preferably connects the mask seal 110 to the mask base 114. While the illustrated mask seal 110 and mask seal clip 112 are formed separately and secured together, in some configurations, the mask seal 110 and the mask seal clip 112 can be integrated into a single component. In some configurations, the mask seal 110 is overmolded onto the mask seal clip 112.

Figure 3:
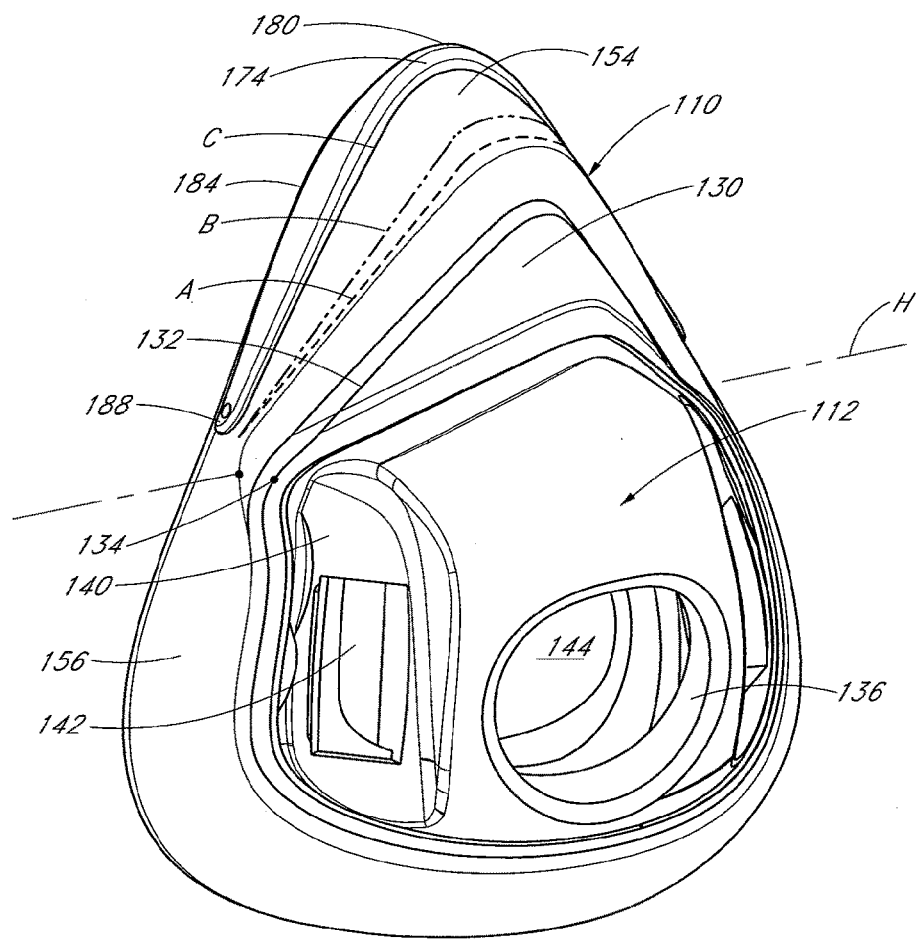
FIG. 3 is a perspective view of a mask seal and mask seal clip of the interface of FIG. 1.

With reference to FIG. 3, the mask seal clip 112 is relatively more rigid, stiffer or more inflexible than the mask seal 110. In some configurations, the mask seal clip 112 is formed of a polycarbonate material. In some configurations, at least a portion of the mask seal clip 112 is formed of a polycarbonate or other rigid or semi-rigid material. In some configurations, the mask seal clip 112 is formed at least partially of silicone or another suitable material. In such configurations, at least the silicone portion of the mask seal clip 112 may be formed to be relatively thicker compared to the more flexible portions of the mask seal 110. The mask seal clip 112 provides structural support to the mask seal 110 in the illustrated configuration.

Figure 14:
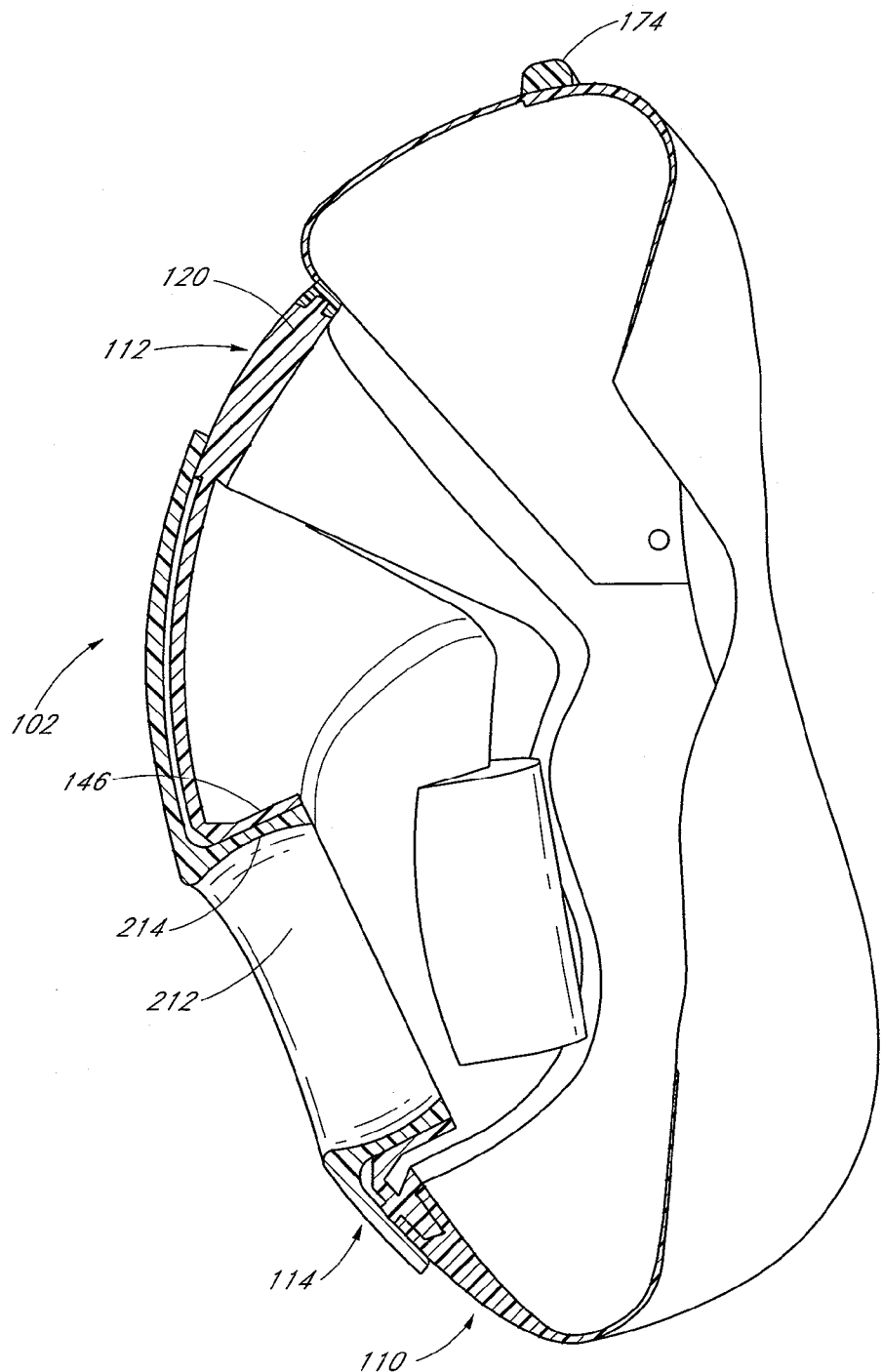
FIG. 14 is a section view of the mask seal, mask seal clip and mask base of FIG. 13.
Figure 25:
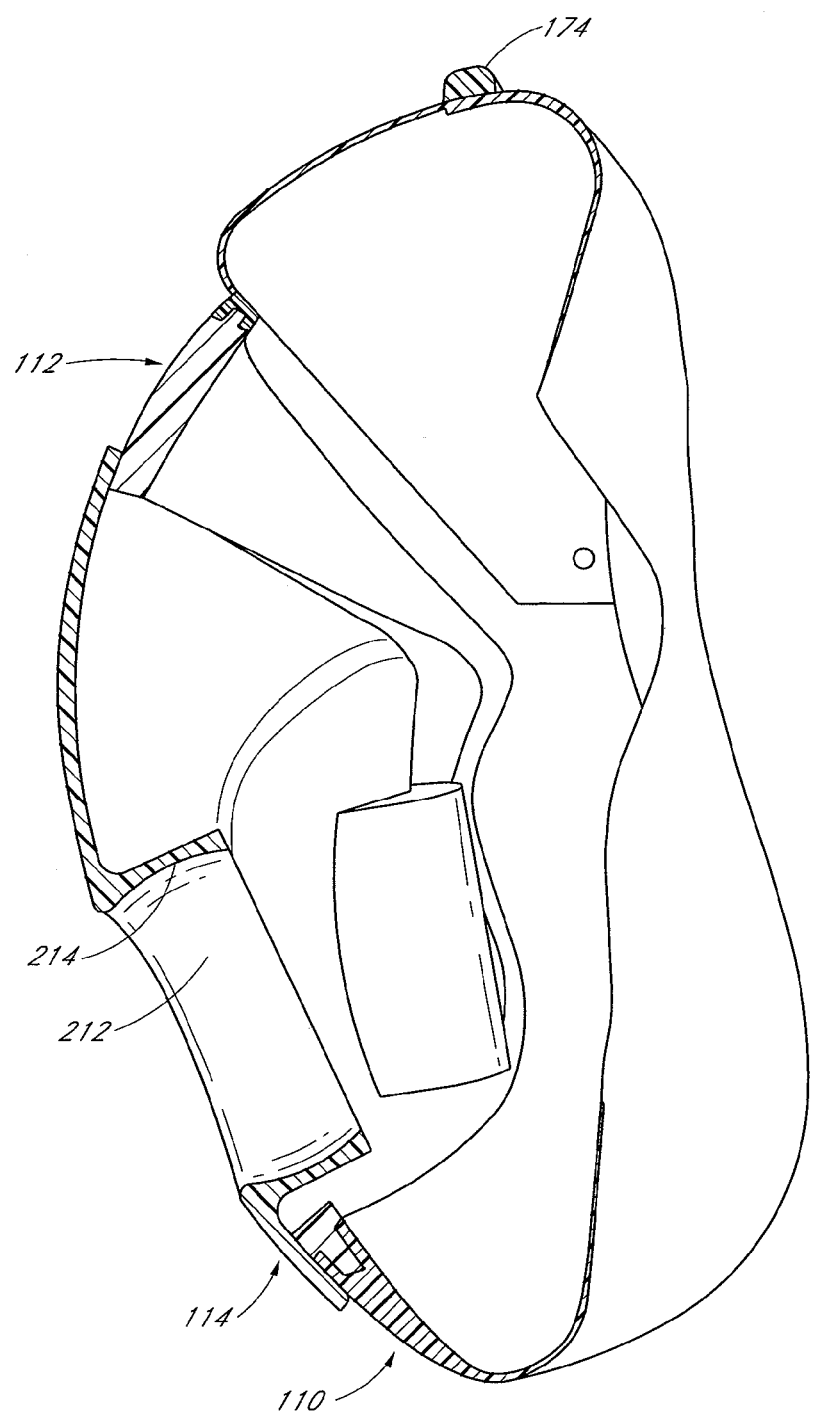
FIG. 25 is a sectioned view similar to the sectioned view of FIG. 14, wherein the mask seal clip has a reduced dimension.
Figure 26:
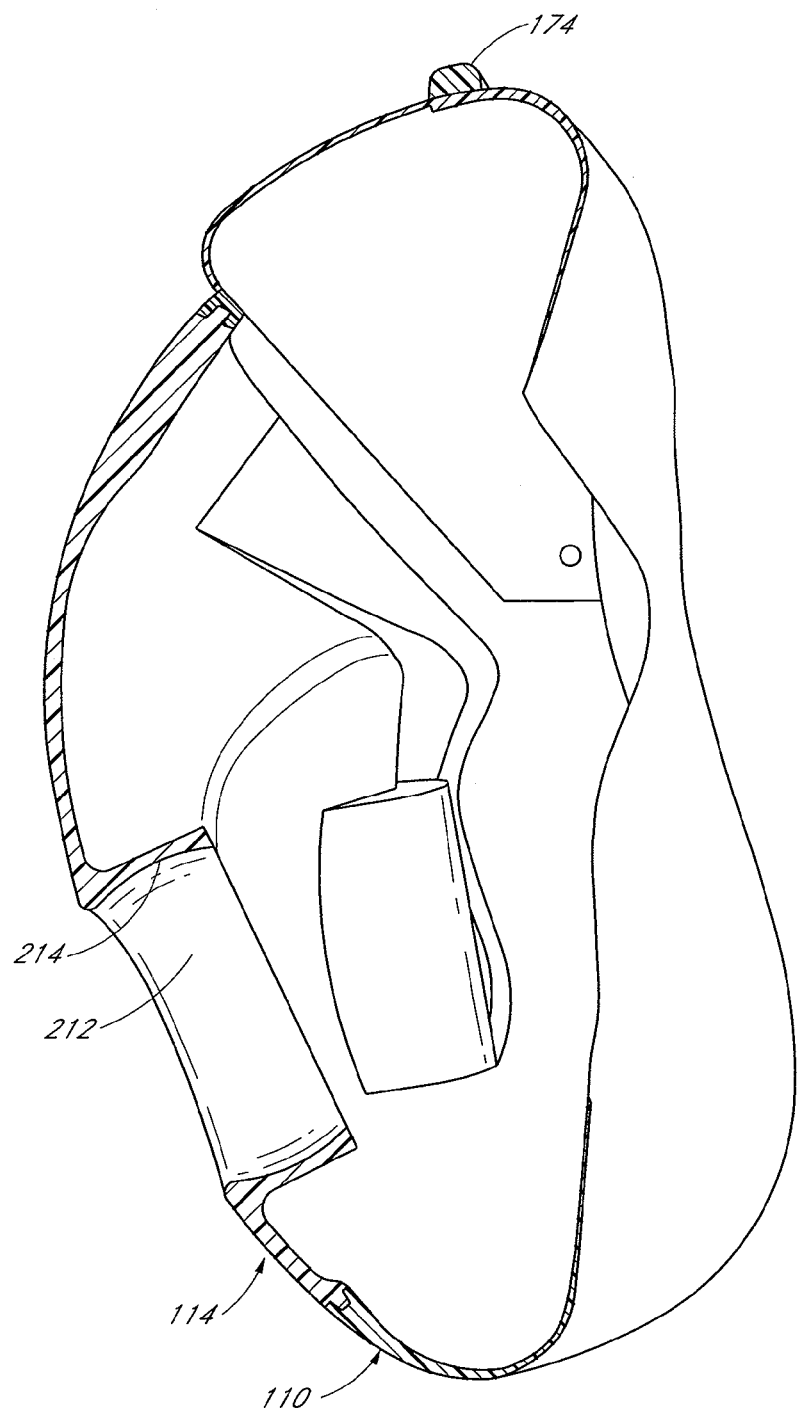
FIG. 26 is a sectioned view similar to the sectioned view of FIG. 14, wherein the mask seal clip is omitted.
Figure 27:
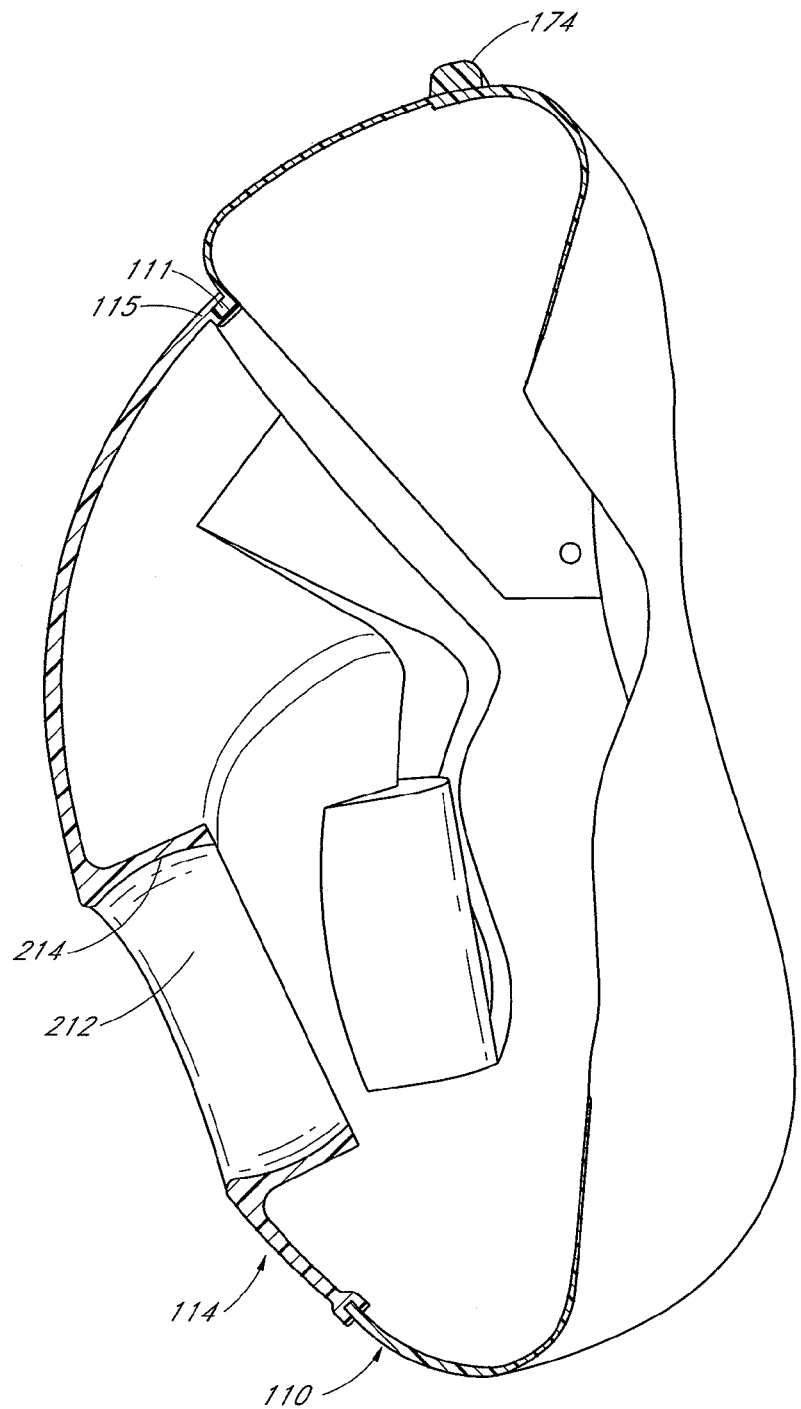
FIG. 27 is a further sectioned view similar to the sectioned view of FIG. 14, wherein the mask seal clip is omitted.

As shown in FIG. 14, the mask seal clip 112 can define a large portion of the mask assembly 102. As shown, the illustrated mask base 114 overlies a significant portion of the mask seal clip 112. With reference to FIGS. 25-27, the mask assembly 102 can be configured with differing constructions, as desired. For example, with reference to FIG. 25, the mask seal clip 112 extends a limited amount from the interface with the mask seal 110. In the configuration illustrated in FIG. 25, the mask base 114 overlies at least a portion of the mask seal clip 112 while the mask seal clip 112 defines a very limited rim-shaped configuration about a portion of the mask seal 110. With reference to FIG. 26, the mask seal clip is omitted in its entirety and the mask seal 110 is overmolded directly onto the mask base 114. In some configurations, however, the mask seal 110 and the mask base 114 can be configured such that the two components can be separated. For example, as shown in FIG. 27, the mask seal 110 can comprise a peripheral flange 111 while the mask base 114 can comprise a peripheral channel 115 that receives the peripheral flange 111 such that the mask seal 110 can be removably secured to the mask base 114. In some configurations, other suitable manners can be used to secure the mask seal 110 to the mask base 114. Moreover, while the illustrated configuration of FIG. 27 shows an embodiment without a mask seal clip 112, the mask seal clip 112 and the mask base 114 have been combined into the mask base 114.

Figure 5:
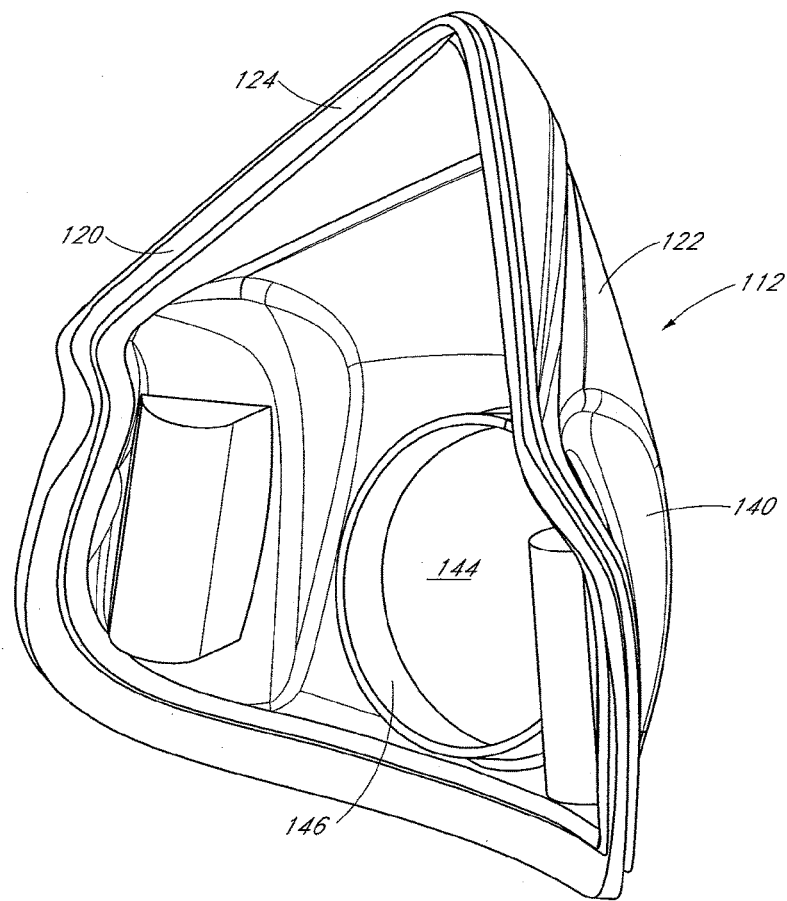
FIG. 5 is a rear perspective view of the mask seal clip of FIG. 3.
Figure 7:
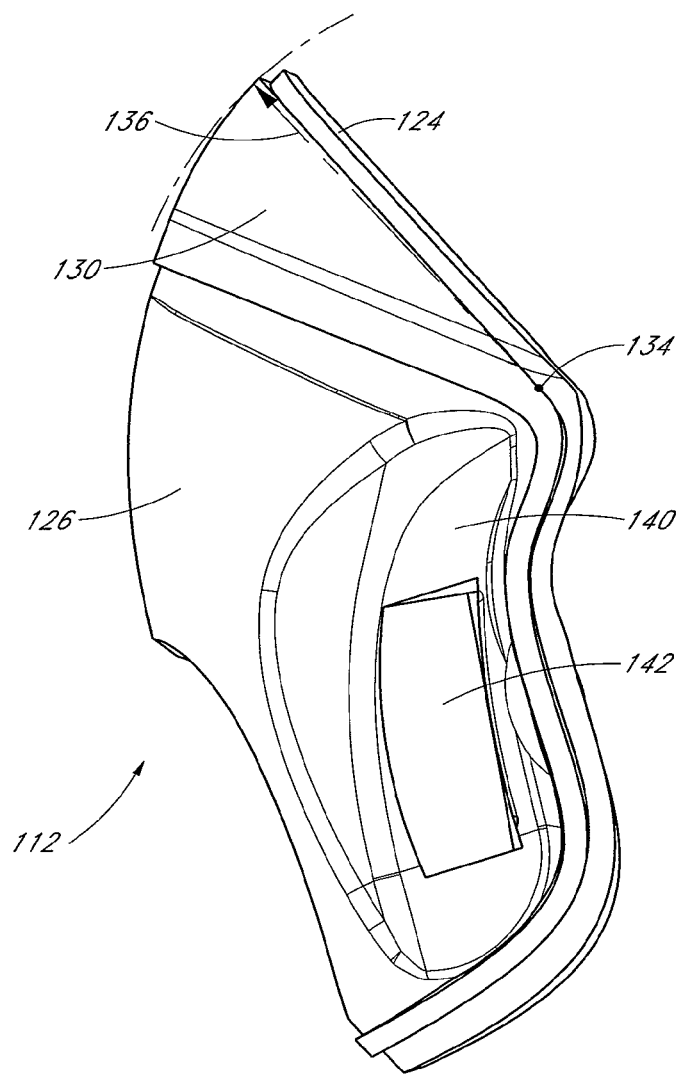
FIG. 7 is a side elevation view of the mask seal clip of FIG. 3.
Figure 8:
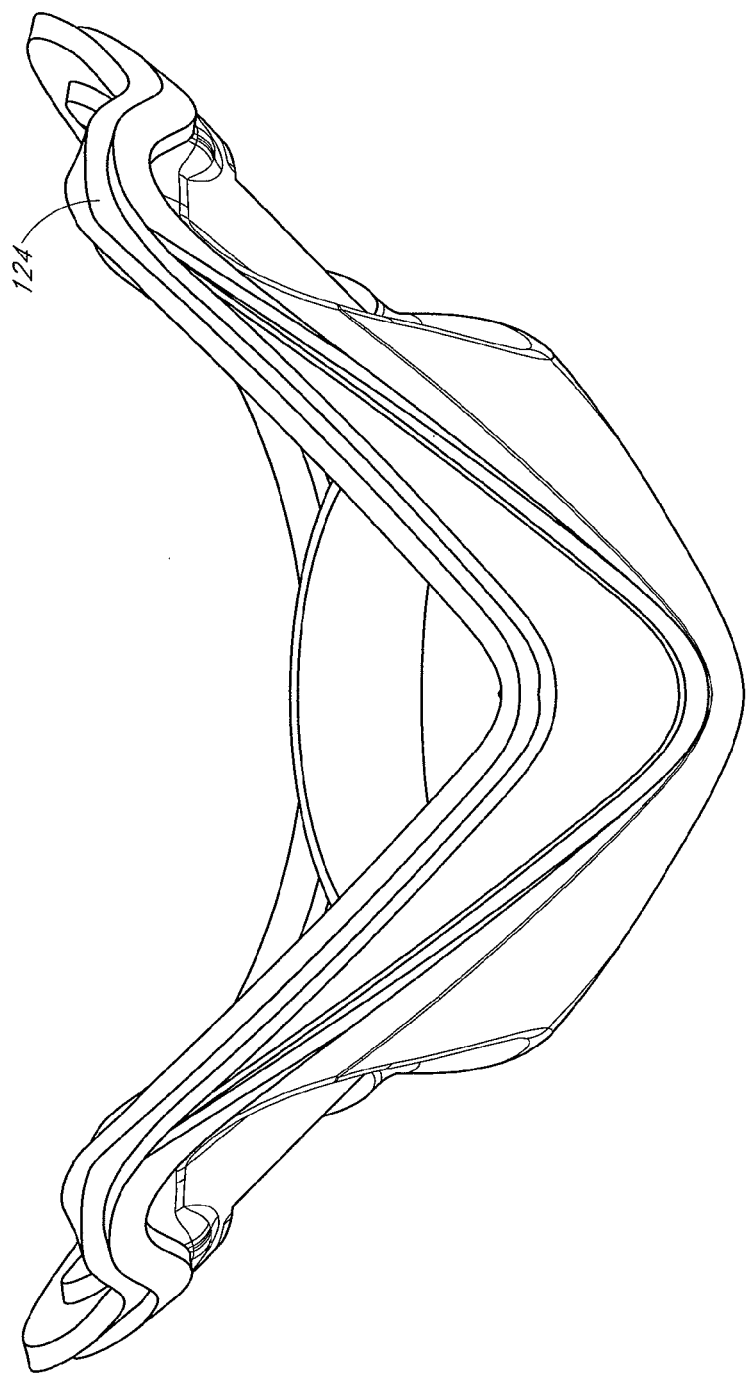
FIG. 8 is a top plan view of the mask seal clip of FIG. 3.

With reference to FIG. 5, the illustrated mask seal clip 112 comprises a substantially cup-shaped configuration. A proximal end 120 defines an open end of the illustrated mask seal clip 112 while a distal end 122 defines a generally closed end of the illustrated mask seal clip 112. In the illustrated configuration, the proximal end 120 is generally circumscribed by a lip 124. The lip 124 is generally pentagonal when viewed from the back (see FIG. 5). As shown in FIG. 7, a wall 126 generally sweeps forward in an arcuate manner. The arcuate shape to the wall 126 provides a three dimensional configuration to the illustrated mask seal clip 112.

With continued reference to FIG. 7, an upper portion 130 of the illustrated mask seal clip 112 is generally arcuate in configuration. In addition, the generally arcuate configuration of the illustrated mask seal clip 112 is configured to accommodate larger noses while not extending upward over the nose to as great an extend as the mask seal 110, as shown in FIGS. 1 and 2.

With initial reference to FIG. 3, the upper portion 130 of the illustrated mask seal clip 112 preferably comprises two arcuate dimensions. First, an arc length 132 can be defined along an upper extremity of the upper portion 130 of the illustrated mask seal clip 112. The arc length 132 can be defined between inflection points 134 found along a perimeter of the illustrated mask seal clip 112.

As shown in FIG. 7, the upper portion 130 of the illustrated mask seal clip 112 also comprises a side profile radius 136. As shown, the upper portion 130 can have a slightly increasing side profile radius 136 such that the radius increases slightly as a distance from the upper end increases. In some configurations, the upper portion 130 can comprise a substantially constant side profile radius 136 or a decreasing side profile radius. Advantageously, the slightly increasing side profile radius 136 provides an increased volume in the mask 100 proximate the user's nose.

Figure 6:
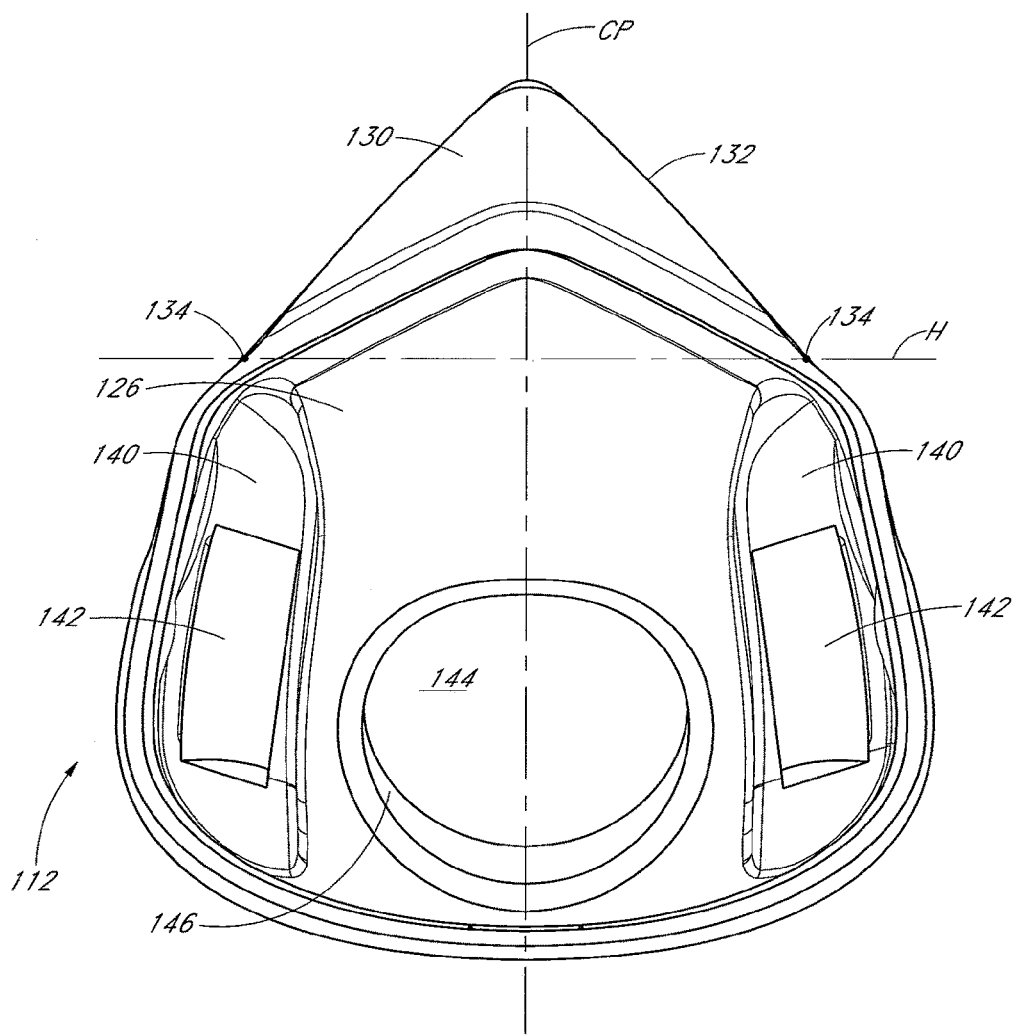
FIG. 6 is a rear elevation view of the mask seal clip of FIG. 3.

With reference to FIG. 3 and FIG. 6, the mask seal clip 112 preferably comprises at least two recesses 140. In the illustrated configuration, the mask seal clip 112 comprises two recesses 140 that are disposed on two lateral sides of a generally vertical center plane CP (see FIG. 6). The generally vertical center plane CP preferably corresponds to a mid-sagittal plane of the user and splits the illustrated mask seal clip 112 into substantially mirror image halves. The two recesses 140 define two generally enclosed pockets in the illustrated mask seal clip 112. The illustrated recesses 140 comprise further recesses 142 that are used to provide adequate clearance for reasons that will be discussed below while limiting an amount of encroachment into a nasal region of a chamber defined by the mask assembly 102.

The illustrated mask seal also comprises a generally central passage 144 that is defined by a wall 146. In the illustrated configuration, the wall 146 generally encloses the passage 144. Preferably, the wall 146 is generally cylindrical in configuration and extends through the wall 126. Other configurations are possible.

With reference to FIG. 14, the mask seal 110 comprises a flexible portion that extends away from the proximal end 120 of the mask seal clip 112. In the illustrated configuration, the mask seal 110 is overmolded onto the mask seal clip 112 such that the mask seal 110 and the mask seal clip 112 combine to form an integrated and preferably non-separable assembly. In some configurations, attempts to separate the mask seal 110 and the mask seal clip 112 result in the destruction of the interface between the components and/or destruction of one or both of the mask seal 110 and the mask seal clip 112. As described above, other assemblies also can be used to connect the mask seal clip 112 to the mask seal 110. The illustrated configuration, however, advantageously results in a construction that is easy to clean and maintain.

Figure 4:
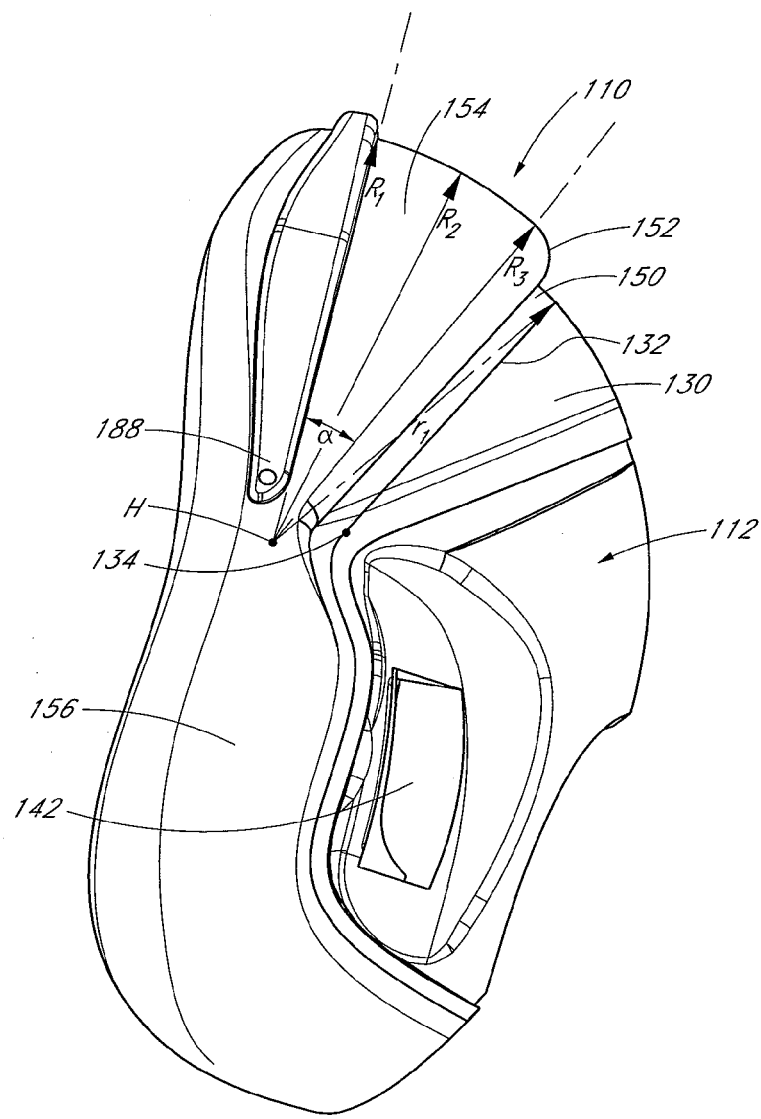
FIG. 4 is a side view of the mask seal and mask seal clip of FIG. 3.

With reference to FIG. 4, the mask seal clip 112 preferably is arranged such that it is generally flush with an inner rim 150 of the mask seal 110. In the illustrated configuration, the mask seal 110 comprises a relatively small radius portion 152 that joins an upper portion 154. The upper portion 154 of the mask seal 110 is configured to extend over a nasal region of the user. In some configurations, the upper portion 154 is configured to extend over a nasal bridge region of the user U.

Figure 9:
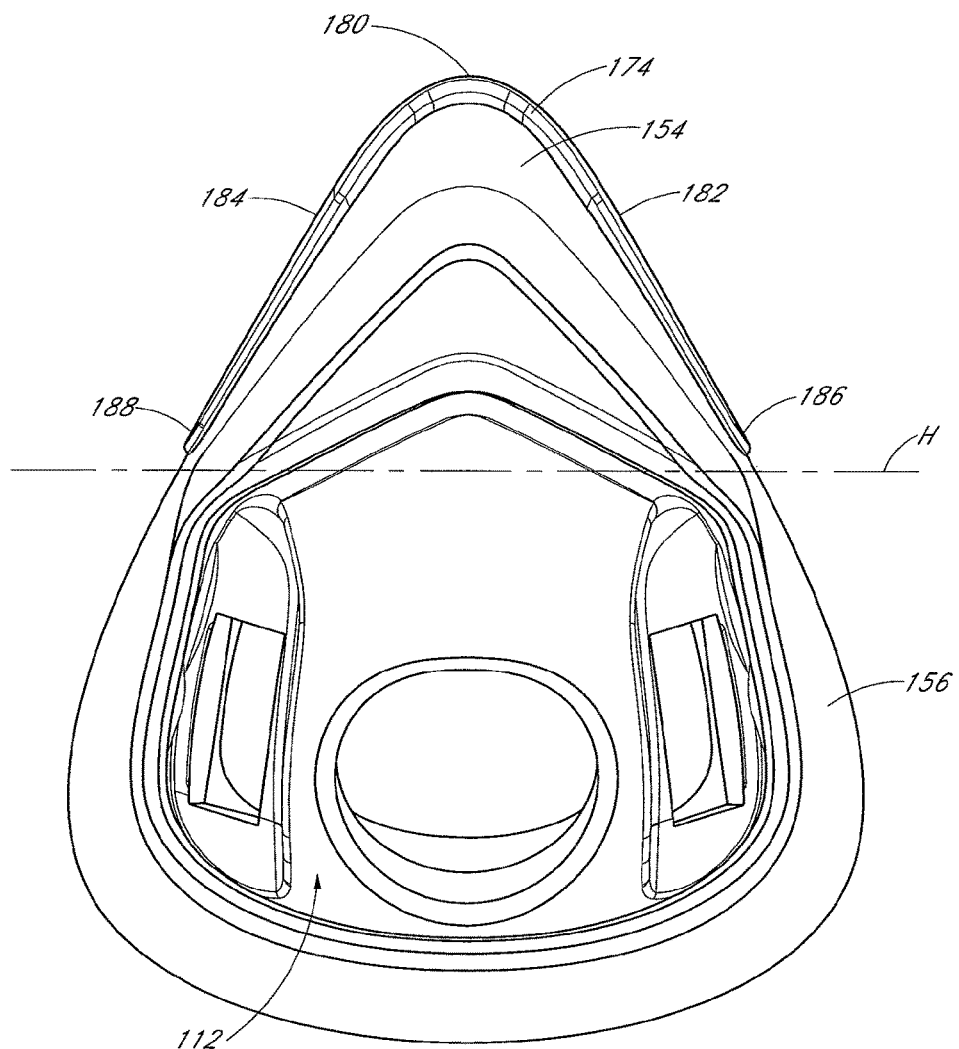
FIG. 9 is a front elevation view of the mask seal and mask seal clip of FIG. 3.
Figure 10:
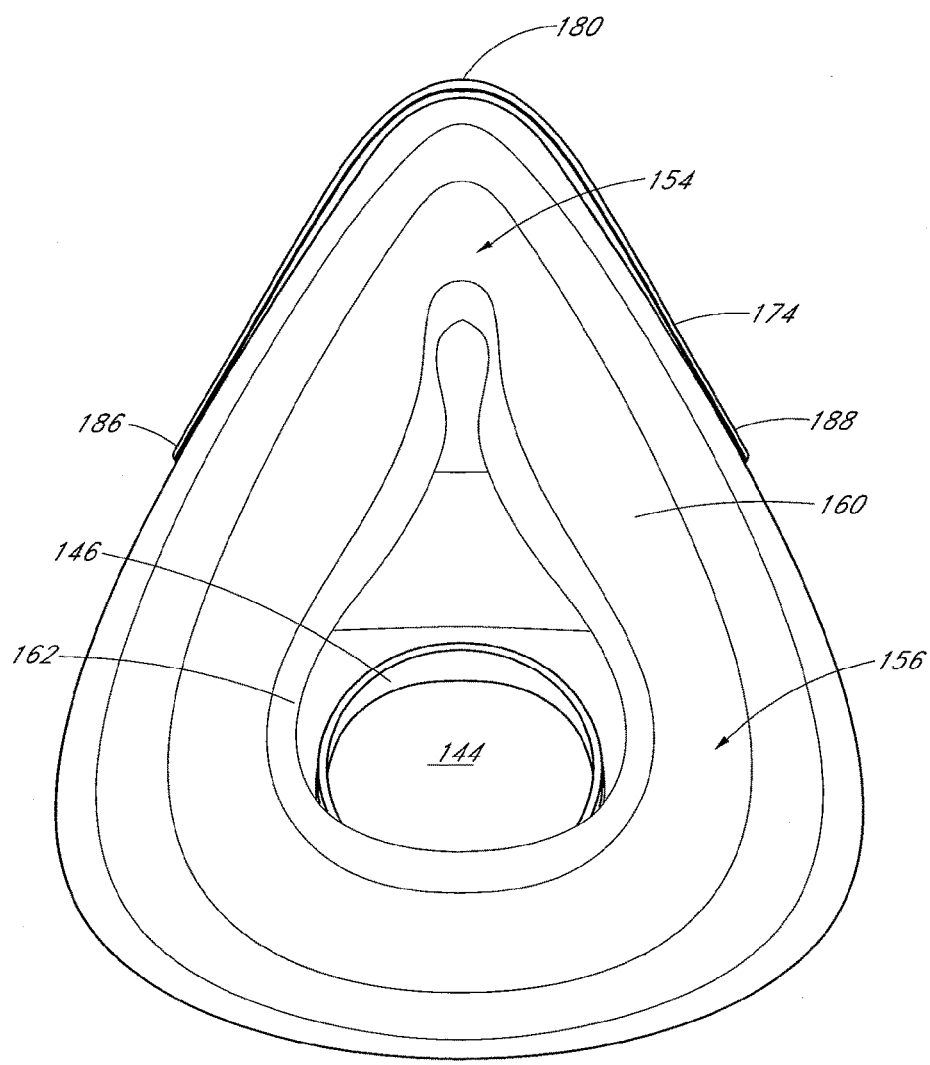
FIG. 10 is a rear elevation view of the mask seal and mask seal clip of FIG. 3.

The upper portion 154 is connected with a lower portion 156 of the seal member 110. The lower portion 156 extends laterally outward from the mask seal clip 112 as shown in FIG. 9. In addition, the lower portion 156 wraps rearward and inward, as shown in FIGS. 4 and 10 respectively. Together, on a proximal side of the full face mask assembly 102, the upper portion 154 and the lower portion 156 combine to define a face contacting flange 160, which is shown in FIG. 10. The face contacting flange 160 is configured to underlie a lower lip of the user, extend along the outside of the mouth, extend upward along the cheekbones and extend across the bridge of the nose of the user. Thus, the illustrated face contacting flange 160 defines a generally tear-drop shaped opening 162. When the mask assembly 102 is seated on the face of the user, the flange 160 will lie flat over the bridge of the nose, the cheekbones, the outside of the mouth and below the lower lip of the user. With a supply of positive pressure air, the mask seal 110 will balloon and seal against the face of the user to reduce or eliminate the likelihood of leakage between the flange 160 and the face of the user.

Figure 11:
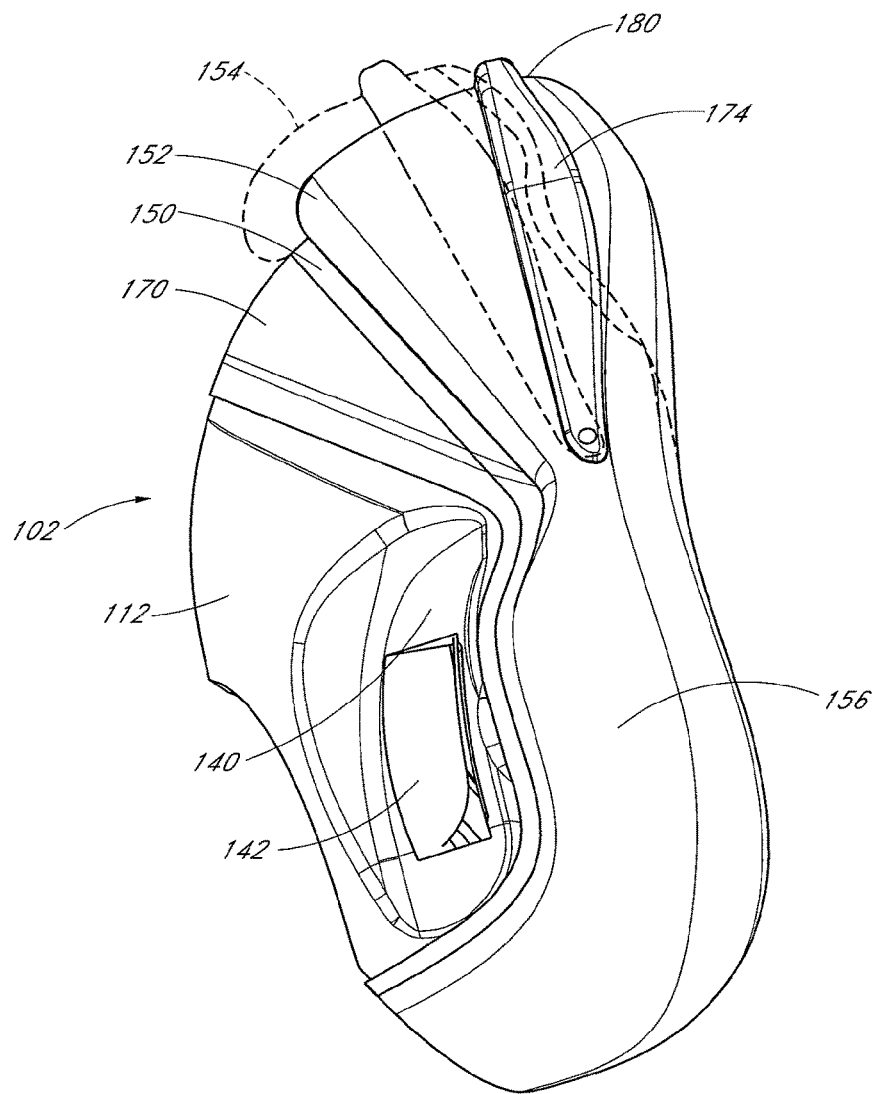
FIG. 11 is a side elevation view of the mask seal and mask seal clip of FIG. 3.
Figure 12A:
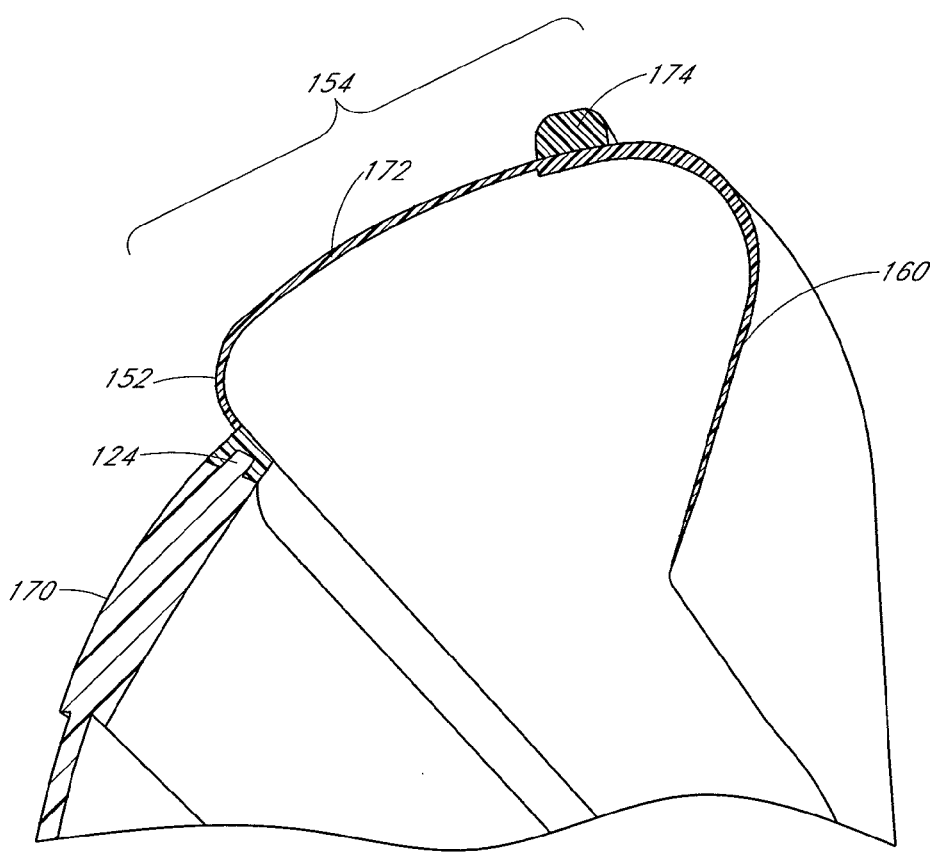
FIG. 12 is an enlarged section view of a portion of the mask seal and mask seal clip of FIG. 3.
Figure 12B:
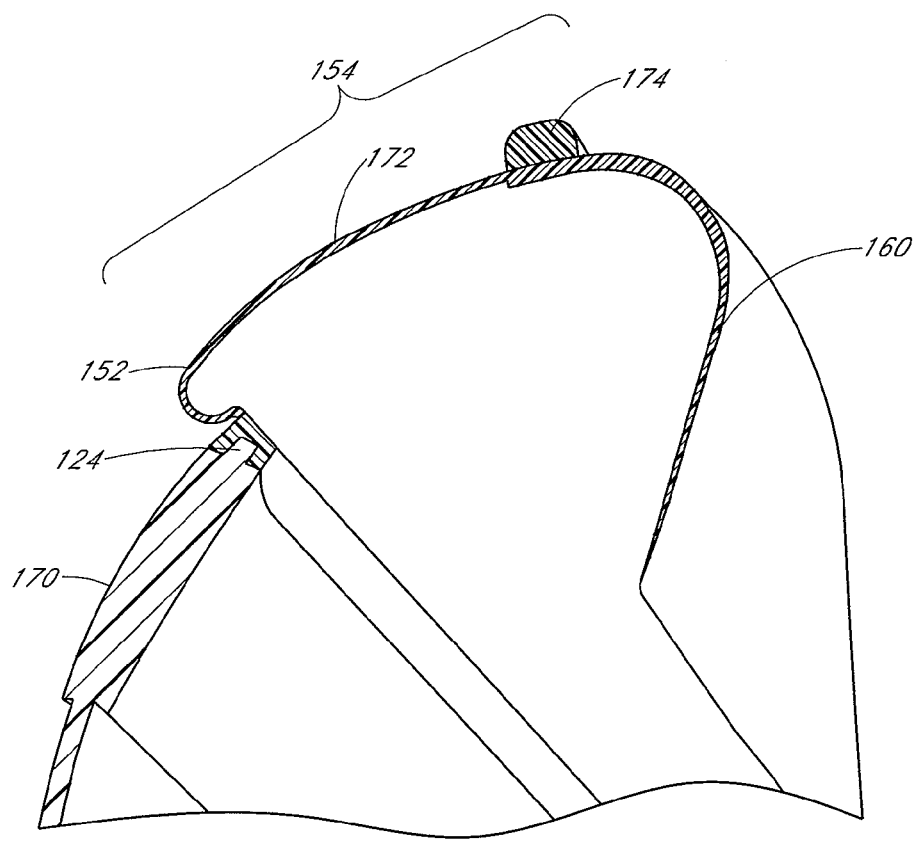
Figure 12C:
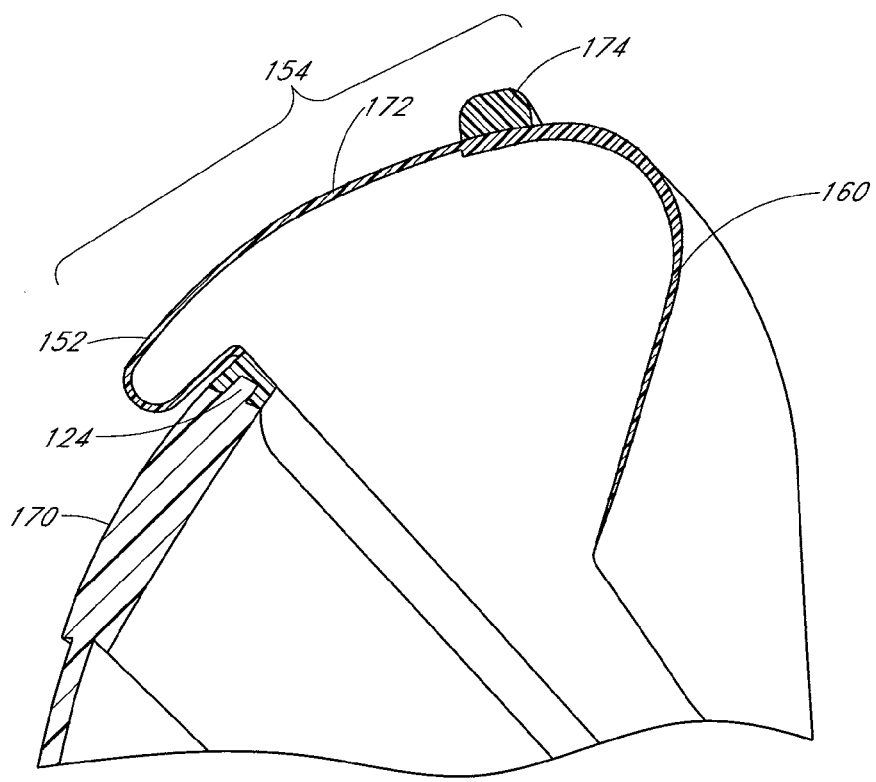
Figure 12D:
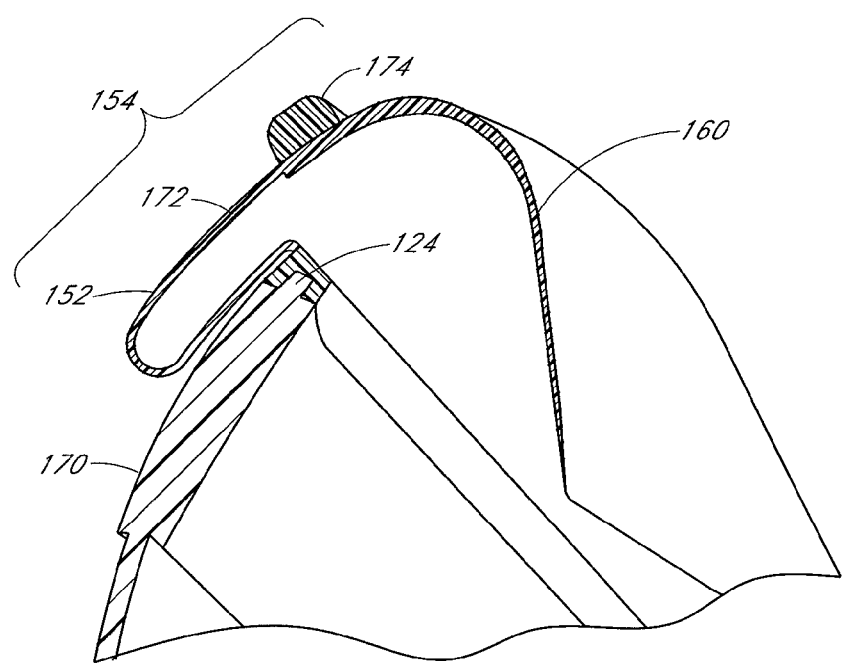

As shown by the dashed lines in FIG. 11, the upper portion 154 of the mask seal 110 is designed to roll over onto an outer surface 170 of the mask assembly 102. In the illustrated configuration, the outer surface of the mask seal 110 smoothly rolls into abutment with the outer surface of the mask seal clip 112 such that the outer surface of the mask seal clip 112 forms a support surface. In some configurations, the outer surface 170 onto which the upper portion 154 rolls comprises at least a portion of the outer surface of the mask seal clip 112. In some configurations, the outer surface 170 onto which the upper portion 154 rolls comprises almost exclusively the outer surface of the mask seal clip 112. In some configurations, the upper portion 154 rolls onto another portion of the mask seal 110. In some configurations, the upper portion 154 rolls onto the mask seal base 114.

With reference to FIG. 12, to assist with the rolling of the upper portion 154, the upper portion 154 can have a varying thickness or a varying stiffness. In the configuration shown in FIG. 12, the upper portion 154 comprises a thick/thin/thick configuration. In other words, to induce the upper portion 154 to roll in a region between the face contacting flange 160 and the small radius 152 proximate the mask seal clip 112, a reduced stiffness region 172 can be incorporated. In the illustrated configuration, the reduced stiffness region 172 is incorporated into the mask seal 110. The reduced stiffness region 172 reduces or eliminates the likelihood of the mask seal 110 buckling or adversely deforming in a region other than the desired region for rolling.

While the illustrated configuration uses a region of reduced thickness, other means for providing the reduced stiffness region 172 also can be used to induce rolling of the seal member 110. For example, the material of the seal member 110 can be configured to have a reduced stiffness through material selection or material properties. In addition, a composite of materials can be used to provide a region of reduced stiffness or rigidity. Moreover, a combination of any suitable techniques can be used. Nevertheless, the illustrated region 172, which is configured with reduced thickness, provides a simple manner of achieving the region of reduced stiffness 172. In addition, by adjusting the stiffness of the reduced stiffness region 172, the force required to induce rolling of the region 172 can be controlled, which controls the force applied against the nose of the user. For example, by varying the stiffness, movement can become increasingly or decreasingly resisted over the range of movement.

When the upper portion 154 comprises the region of reduced stiffness 172, the upper portion 154 of the mask seal 110 tends to balloon outward under internal pressures, such as those encountered during positive pressure therapy regimens, which ballooning is believed to be caused by the region of reduced stiffness 172 that defines a large area of silicone without significant structure. With reference to FIG. 4 and FIG. 12, to reduce the prevalence of ballooning in the upper portion 154 and to provide enhanced structure in the upper portion 154, a reinforcing component or components, such as a band 174, can be positioned along at least a portion of the upper portion 154. The band 174 can be a component formed of a material that is more rigid than, or that features increased stiffness relative to, the silicone or other material forming the mask seal 110. For example, a region of significantly increased thickness relative to the region of reduced stiffness 172, where the region is formed of the same material forming the mask seal 110, can be used to increase the stiffness of the reinforcing component or components.

In some configurations, the band 174 can be a separately formed component that is at least partially encased by the material of the mask seal 110. In the illustrated configuration, the band 174 can be a comolded plastic component or the mask seal 110 can be overmolded onto the band 174. In some configurations, the band 174 can be defined by a portion of the upper portion 154 that has enhanced stiffness relative to surrounding regions. For example, but without limitation, the band 174 can be defined by a portion of increased thickness, a portion of differing materials or material properties that result in increased stiffness or the like.

With reference to FIG. 9, the band 174 extends along at least a portion of the upper portion 154 of the mask seal 110. The upper portion 154 of the mask comprises an apex 180 when viewed from the front. The apex 180 can be defined as a tip, a top and an angular summit of the mask seal 110, which apex 180 is positioned in proximity to the nose of the user when in use. A first wall 182 and a second wall 184 converge at the apex 180 in the illustrated configuration.

In some configurations, at least a portion of the first wall 182 and at least a portion of the second wall 184 are reinforced by one or more components or structures, such as the band 174. In the illustrated configuration, the reinforcing component or components, such as the band 174 for example, reinforces at least a portion of the first wall 182 and at least a portion of the second wall 184. In some configurations, the reinforcing component or components, such as the band 174 for example, reinforces at least a portion of the first wall 182, at least a portion of the second wall 184 and the apex 180.

With continued reference to FIG. 9, the illustrated band 174 has a first end 186 and a second end 188 that is opposite to the first end 186. In some configurations, the band 174 can be formed separate of the mask seal clip 112 and attached to the mask seal clip 112 by one or more flexible components. In some configurations, the band 174 can be connected by a mechanical hinge structure to the mask seal clip 112. In the illustrated configuration, the first end 186 and the second end 188 are positioned on the same side of the hinge axis H as the apex 180. Preferably, the first end 186 and the second end 188 are spaced away from the hinge axis H toward the apex 180.

As shown in FIG. 12, the bend 152 and the stiffer region (e.g., region of thicker cross section) adjacent to the region of reduced stiffness 172 help to initiate rolling of the region of reduced stiffness 172. In other words, a controlled buckling of the region of reduced stiffness 172 occurs with the assistance of the adjacent stiffer portions. In addition, positioning an edge of the relatively more rigid mask seal clip 112 adjacent to the bend 152 further helps to induce rolling in the reduced stiffness region 172. In some configurations, the region of reduced stiffness 172 is bounded by a first boundary and a second boundary, wherein the first boundary and the second boundary have an increased stiffness relative to the region of reduced stiffness. In the illustrated configuration, for example, the first boundary is defined by or alongside the band 174 while the second boundary is defined by or alongside the bend 152. In some configurations, the second boundary can be defined by or alongside an edge of the more rigid mask seal clip 112. In some configurations, the second boundary can be defined along a portion of the mask seal 110 positioned between the mask seal clip 112 and the region of reduced stiffness 172.

As the upper portion 154 of the mask seal 110 is displaced about the hinge axis H, the roll increases in size. In other words, as the first boundary initially moves toward the second boundary, a roll is formed in the mask seal 110. As the first boundary continues to move toward the second boundary, the roll continues to increase in size. Thus, in the illustrated configuration of FIG. 11, the roll defined in the upper portion 154 starts at nothing and progressively increases during displacement of the upper portion 154 as shown in dashed lines. Preferably, the rolling between the first boundary and the second boundary creates a single bend or inflection between the first boundary and the second boundary. The single bend results in legs approaching the bend location that increase in size as the first boundary moves toward the second boundary. In other words, the rolling created by movement of the first boundary toward the second boundary preferably does not result in a fan-folding appearance such as a pleated configuration.

With reference again to FIG. 3, the mask seal 110 can have a geometry that helps facilitate continued rolling of the region of reduced stiffness 172 following the initiation of the rolling. Arc lengths can be defined in general from a first intersection of the hinge axis H with the mask seal 110, up and over the upper portion 154 of the mask seal 110, and back down to a second intersection of the hinge axis H with the mask seal 110.

As shown in FIG. 3, the illustrated mask seal 110 comprises at least a first arc length A (shown in dashed line), a second arc length B (shown in dash-dot chain line) and a third arc length C (shown along a base of the band 174). The first arc length A preferably is longer than the arc length of the mask seal clip 112 directly adjacent to the first mask arc length A. The second arc length B is positioned between the first arc length A and the third arc length C and the second arc length B preferably is shorter than the third arc length C and longer than the first arc length A. In some embodiments, the arc lengths steadily increase from the bend 152, or another region close to the outer surface 170, proximal toward the band 174. In other words, as an angle α (see FIG. 4) increases from the first arc length A, the arc length generally increases. In some configurations, the arc lengths can be substantially constant from front to rear (i.e., as the angle α increases); however, by increasing the arc lengths away from the portion that initiates the roll, further movement of the apex 180 in a distal direction results in continued rolling of the mask seal 110 over itself and over the outer surface 170, as shown in FIG. 11.

With reference again to FIG. 4, the upper portion 154 of the illustrated mask seal 110 also comprises a variable radius when viewed from the side profile. As shown, R1>R2>R3. Thus, in the illustrated mask seal 110, the radius decreases from proximal to distal as the angle increases. In some configurations, the radius need not decrease in this manner; however, the decreasing radius is believed to aid in rolling of the mask seal 110.

Moreover, a radius r1 of the mask seal clip 112 from the hinge point H preferably is smaller than the radius R3 of the mask seal 110. Given the pliant nature of the mask seal 110, however, it is possible for the radius r1 and the radius R3 to be substantially the same while still providing for the mask seal 110 to roll over the mask seal clip 112. In the illustrated configuration, however, the difference between the radius r1 and the radius R3 results in an offset. The offset provides an ability to slightly increase the side profile radius 136, as described above, without significantly impacting the ability of the mask seal 110 to roll over the mask seal clip 112. If the offset were not provided, the ability to increase the side profile radius 136 would be very limited.

As discussed above, the flange 160 encircles the generally tear-drop shaped opening 162. As is known, hoop stress can be defined as circumferential stress in a cylindrically shaped part as a result of internal pressure. Thus, hoop stress increases as a ring attempts to expand. It is believed that hoop stress resulting from seating a respiratory mask can be a source of some discomfort to the user, especially in the region of the bridge of the nose. The lower portion 156 of the illustrated mask assembly 102 generally is secured in position while the nasal or upper portion 154 moves relative to the nose of the user. Because of the rolling action described above, the illustrated full face mask assembly 102 acts to roll away from the nose, which decreases the incidence of increasing hoop stress, especially around the bridge of nose. Thus, the rolling mask configuration provides a means for maintaining or reducing hoop stress during seating of the mask.

As discussed above and as shown in FIG. 11, the upper portion 154 of the illustrated mask seal 110 rolls over the outer surface 170 in the illustrated configuration. The rolling over an external mask surface makes use of the positive pressure present within the full face mask assembly because the increased air pressure enhances the ability of the mask seal to roll on itself (i.e., the air pressure decreases a surface tension between the two surfaces of the mask seal that slide relative to each other during rolling) and the slight ballooning effect helps to reduce the likelihood of buckling, creasing or undesired folding of the mask seal 110. Furthermore, in some configurations, the external roll over can provide a visual cue of the degree or angle of displacement of the upper portion 154 of the mask seal 110 relative to the lower portion 156 of the mask seal 110.

In order to provide an enhanced indication to the user of the extent to which the upper portion 154 of the mask has rolled, it is possible to employ a visual indicator. For example, in some configurations, a scale can be imprinted, embossed or otherwise arranged on or near the reduced stiffness region 172. In some configurations, a scale can be positioned along a portion of the mask 100 over which the reduced stiffness region 172 will roll. For increased fidelity, the scale preferably is positioned in a central location such that the extent to which the reduced stiffness region 172 rolls can be maximized. The scale can be a numerical scale or a color gradient scale, for example but without limitation.

In some configurations, a ratchet or lock mechanism can be integrated with the mask such that the reduced stiffness region 172 can be set at a desired roll point. For example, a ratchet mechanism with a series of teeth that engage a closure member (e.g., ziptie locking ratchets) can be used. When the upper portion 154 of the mask is displaced about the hinge point, the lock mechanism enables the upper portion 154 to be retained in position when the mask 100 is removed from the face of the user U. Preferably, the lock mechanism allows that locked position to be released easily as desired such that, if the mask is moved too far, the upper portion can be relaxed into a better fitting position. Thus, the user can set the extent to which the upper portion 154 rolls once and each subsequent use would result in the same level of roll.

Figure 28:
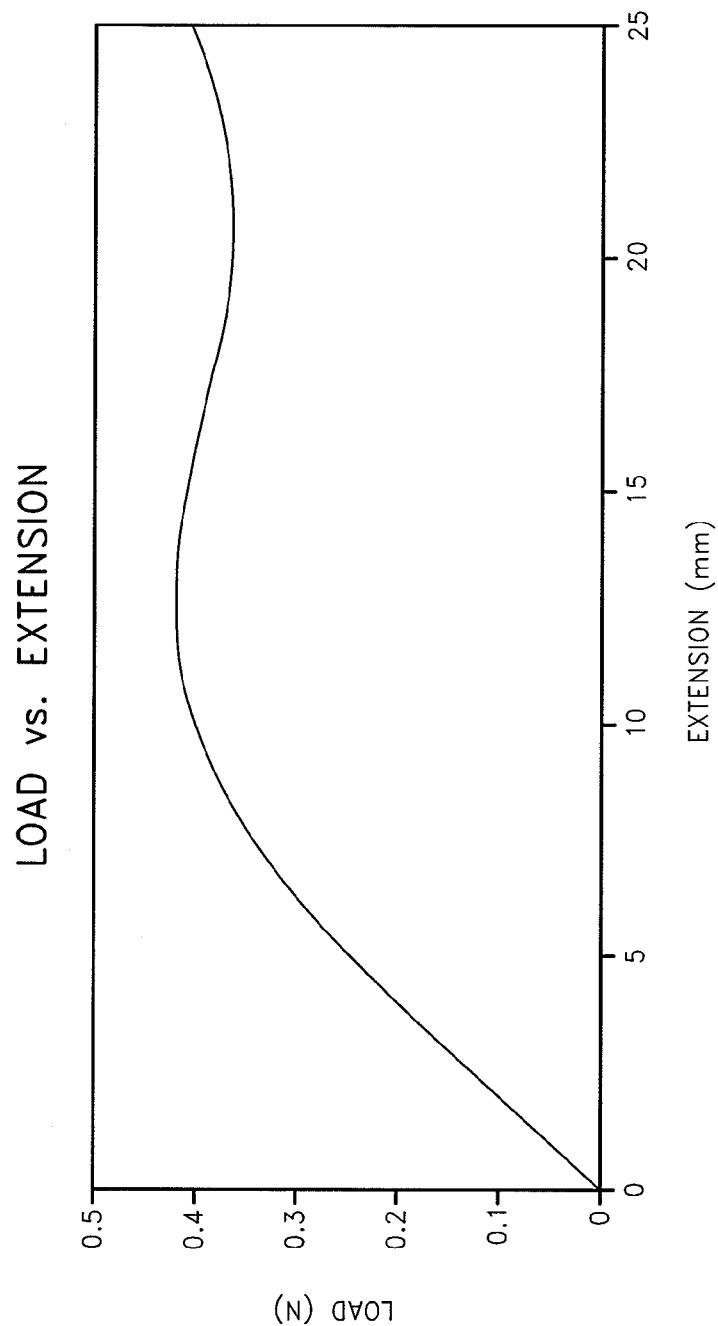
FIG. 28 is a graphical depiction illustrating a relationship between load (or force) on a user's body as a function of mask extension.

By rolling, the upper portion 154 (i.e., the portion of the seal member that contacts the bridge of the nose) moves as increasing pressure is applied by the flange 160 of the mask against the face of the user. As a result of the movement, the force exerted by the upper portion 154 upon the bridge of the nose is substantially constant over a wide range of pressures exerted by the lower portion 156 against the rest of the face of the user. Similarly, the force required to cause the upper portion 154 to move is substantially constant. As shown in FIG. 28, the illustrated configuration results in a full 25 mm change in position of the upper portion with an increase of less than about 0.5 N of force associated with that range of movement. Because the force applied to the nose is generally constant over a range of angles and associated upper portion displacement, the force applied to the bridge of the nose does not vary significantly at various headgear tension levels. Again, such a result is shown in FIG. 28, wherein the total change in force over the range of 5 mm to 25 mm of movement at the apex 180 results in a force change of about 0.2 N. In addition, because the force applied to the nose is generally constant over a range of angles, the mask can be adjusted to improve fitting to a variety of facial geometries while limiting the pressure exerted against the sensitive bridge of the nose region.

When compared to constructions featuring pleated geometries, the use of a rolling configuration provides marked improvement. First, external rolling rather than pleating reduced or eliminates the likelihood of the material of the mask seal encroaching into the chamber designed to contain the nose of the user. Thus, external rolling reduces the likelihood of contact with the nose of the user inside the chamber during movement of the upper portion 154 relative to the lower portion 156. Second, external rolling instead of pleating provides a clean appearance and decreases the number of external cavities, which is believe to improve the user's perception of the full face mask assembly when compared to pleated assemblies.

Figure 24:
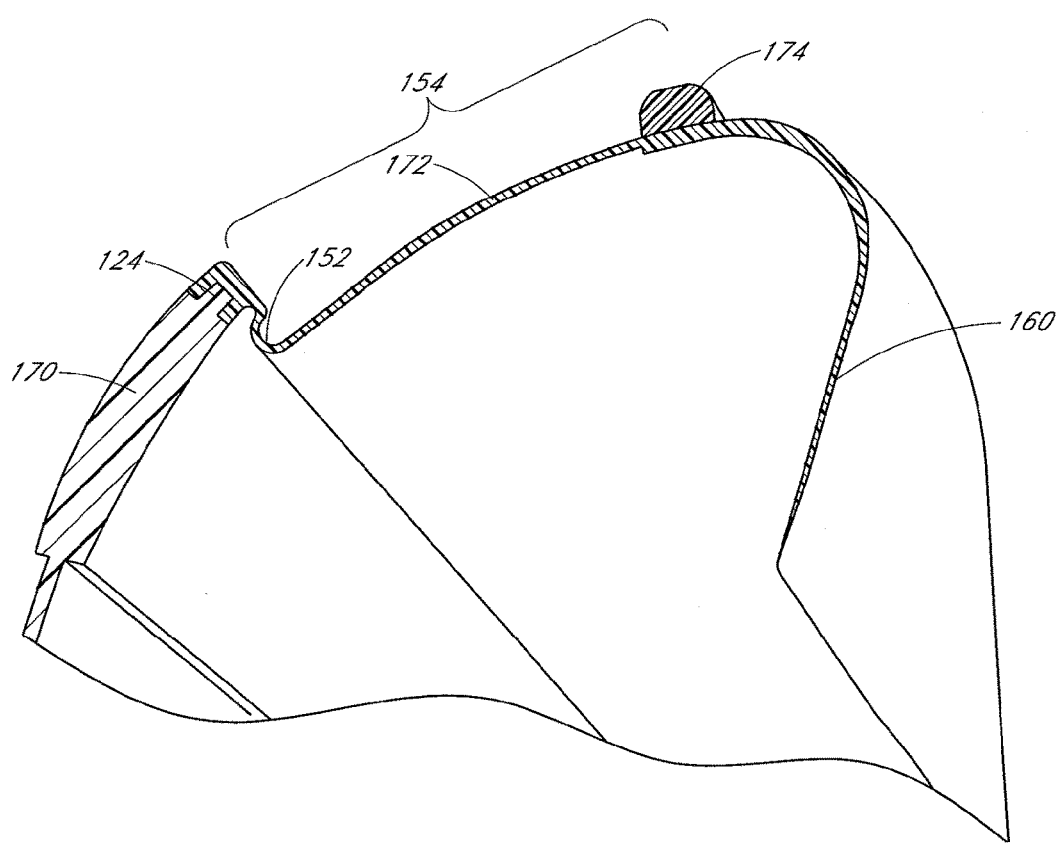
FIG. 24 is a sectioned view similar to the sectioned view of FIG. 12 showing a mask seal configured to roll under a portion of a mask seal clip 112.

With reference to FIG. 24, while the illustrated mask seal 110 rolls over the outer surface 170, the mask seal can be configured to roll inside the mask assembly. In other words, an internal roll over can be used in some configurations. The internal roll over is less desirable relative to the external roll over because the positive pressure tends to hinder rolling and because the rolling action tends to encroach into the chamber that receives the nose. On the other hand, the internal roll over provides a cleaner appearance relative to the external roll over because any ballooning of the seal member is contained within the mask seal clip.

With reference now to FIGS. 1 and 2, the mask assembly 102 includes the mask base 114, which is more rigid than the mask seal 110. The mask base 114 can be formed of any suitable material. In some configurations, the mask base is formed of a polycarbonate material such that it is capable of flexing for connection with the mask seal 110 and/or the mask seal clip 112.

With reference now to FIG. 14, the mask assembly 102 is shown with the mask base 114 secured to the mask seal 110. More particularly, in the illustrated configuration, the mask base 114 is secured to the mask seal clip 112 that is attached to the mask seal 110 in any suitable manner. In some configurations, the mask base 114 and the mask seal 110 or mask seal clip 112 are removably connected. In some configurations, the mask base 114 snaps together with one or both of the mask seal 110 and the mask seal clip 112. Preferably, the mask seal 110 and the mask seal clip 112 can be removed from the mask base 114 and a snap connection secures the mask seal clip 112 to the mask base 114.

Figure 15:
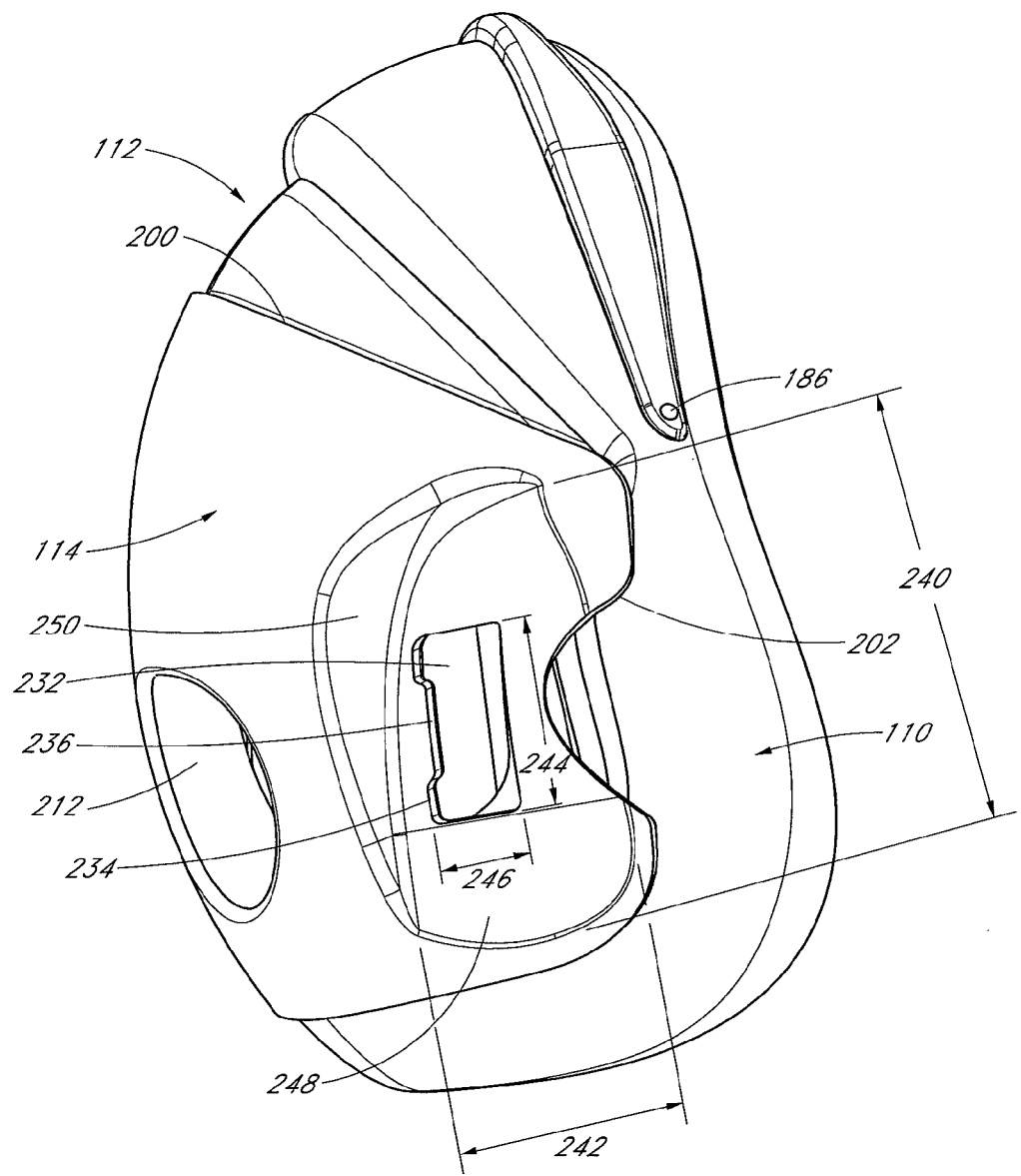
FIG. 15 is a side elevation view of the mask seal, mask seal clip and mask base of FIG. 13.
Figure 16:
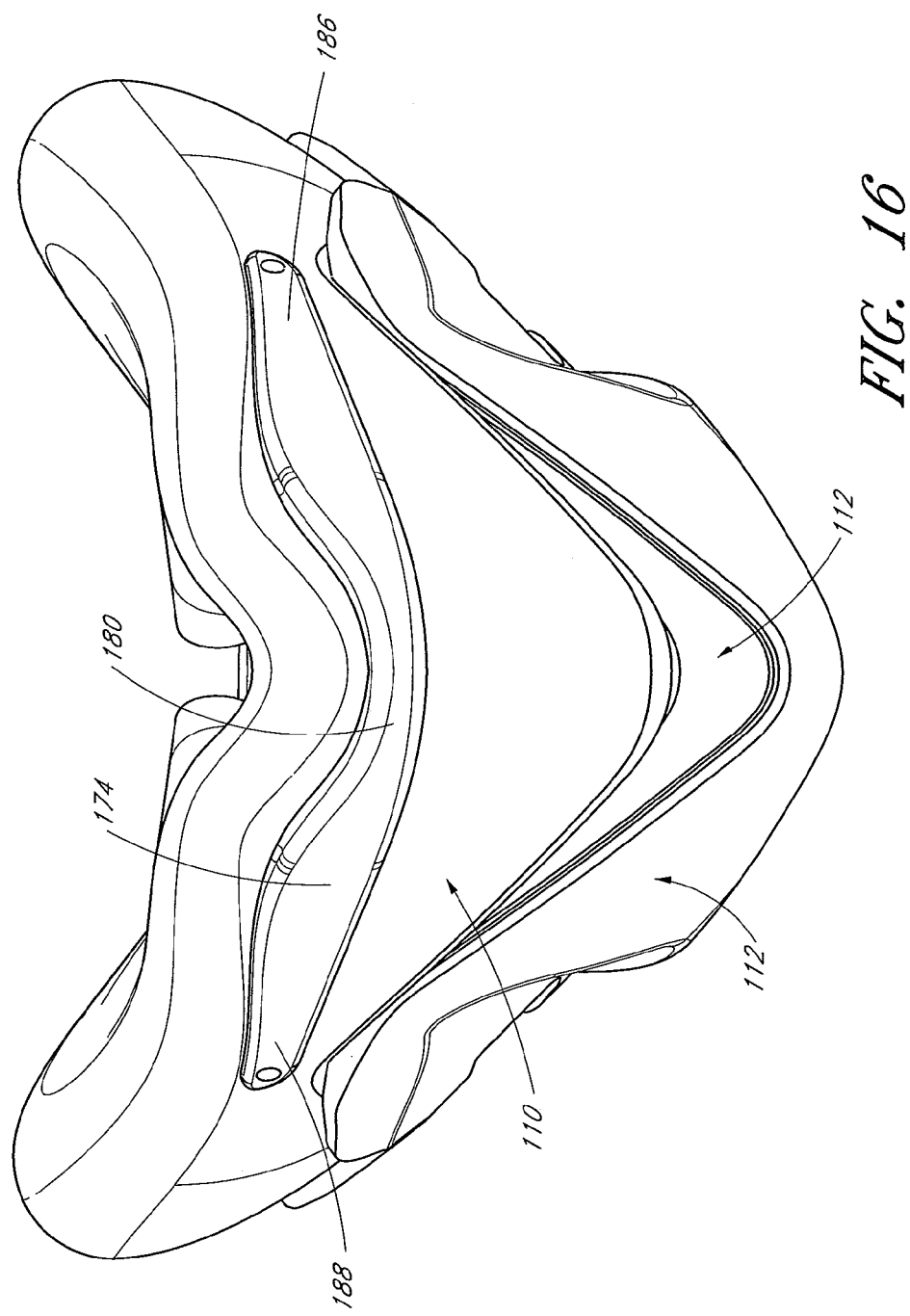
FIG. 16 is a top plan view of the mask seal, mask seal clip and mask base of FIG. 13.

With reference to FIGS. 14 and 15, the illustrated mask base 114 overlies at least a portion of the mask seal clip 112. In some configurations, the mask base 114 almost entirely covers the mask seal clip 112. In some configurations, the mask base 114 extends over more than half of the mask seal clip 112. When the mask base 114 overlies a substantial portion of the mask seal clip 112 or the mask seal 110, a double layer effect is created (e.g., the mask seal clip 112 and the mask base 114). The double layer effect provides increased insulation when a significant portion of the mask base 114 overlaps a significant portion of the mask seal clip 112 or the mask seal 110. The increased insulation provides a warmer inner portion (e.g., mask seal 110 and/or mask seal clip 112), which results in less rain out of humidity during use. Preferably, at least a portion of the mask seal clip 112 is exposed from under the mask base 114 such that the mask base 114 can be more easily separated from the mask seal clip 112. As shown in FIG. 15, to aid in the separation of the mask base 114 from the underlying mask seal 110 and/or mask seal clip 112, the illustrated mask base 114 comprises a peripheral surface 200 on the proximal end. The mask base 114 is concave on the inside to accommodate the underlying components. In other words, the mask base 114 is bowl shaped in a distal direction relative to the proximal peripheral surface 200.

The peripheral surface 200 comprises one or more recessed portions 202. Preferably, the recessed portions 202 comprise at least two recessed portions 202 that are positioned on opposite sides of the mask base 114 from each other. The recessed portions 202 are configured to receive a thumb and a finger such that the mask base 114 can be more easily removed from the front of the underlying mask seal clip 112. While the recessed portions 202 can define means for grasping the assembly underlying the mask base 114 for removal of the mask base, other configurations can be used, such as outwardly extending tabs, protruding portions and the like, for example but without limitation. In addition, while the illustrated recessed portions 202 are disposed on opposing lateral sides of the mask base 114, the recessed portions 202 can be positioned on the top and bottom or on other regions as desired.

As shown in FIG. 13, the mask base 114 preferably comprises an opening 210 that is defined by a wall 212. With reference to FIG. 14 (which is a section through the mask seal 110, the mask seal clip 112, and the mask base 114), the wall 212 that defines the opening 210 through the mask base 114 preferably fits within the wall 146 that defines the passage 144 through the mask seal clip 112. As shown in FIG. 14, the wall 212 can be axially coextensive with the wall 146. In addition, the dimensions and shapes of the walls 146, 212 can be such that the walls interact with each other to reduce relative slippage between the walls 146, 212 and to reduce the likelihood of the mask seal base 114 inadvertently separating from the mask seal clip 112. In some configurations, the walls 146, 212 fit together and reduce the likelihood of leakage through the interface between the walls. Preferably, a taper lock secures the walls 146, 212 together.

Figure 17:
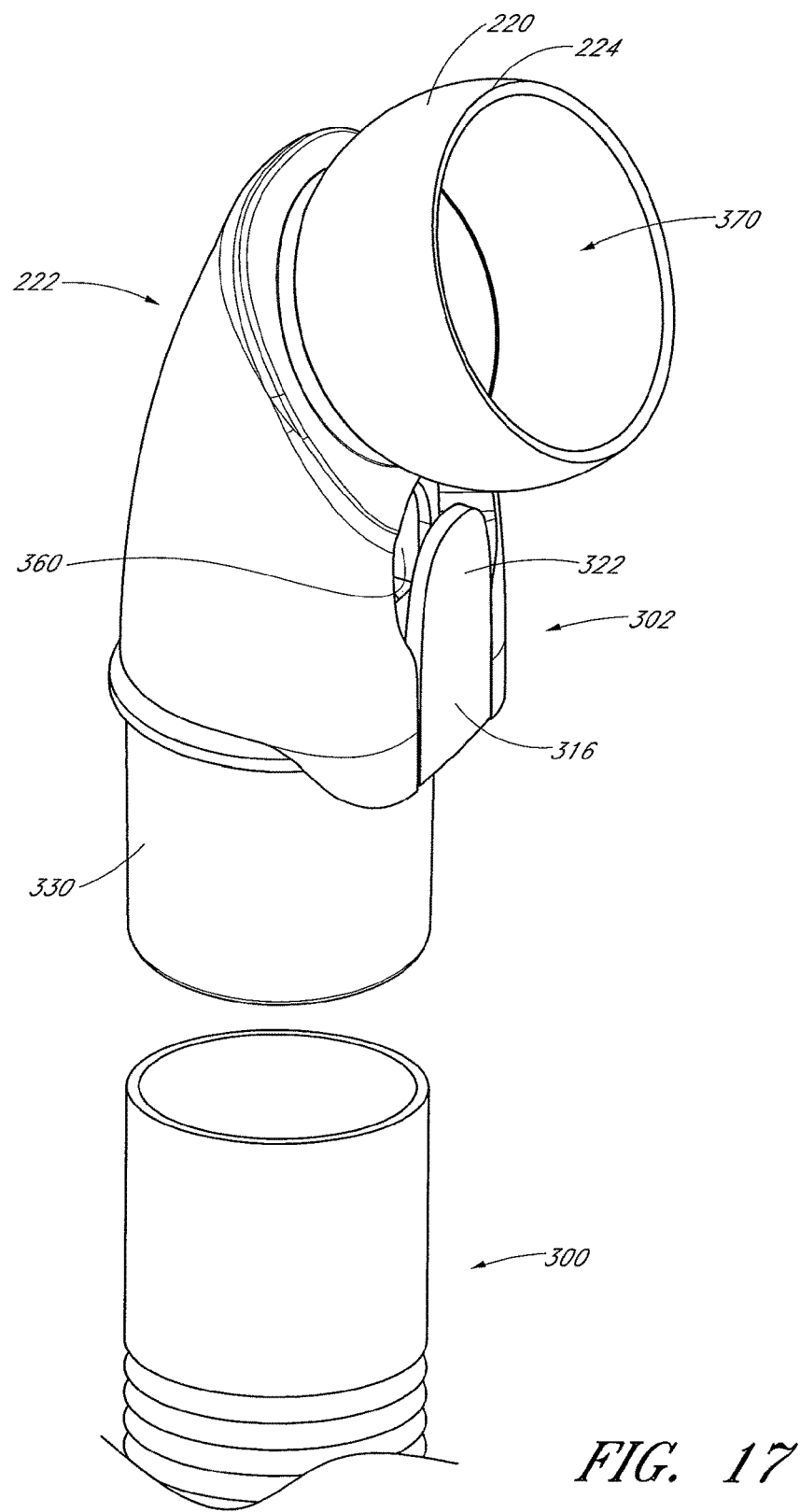
FIG. 17 is a perspective view of the connection port assembly of FIG. 1.
Figure 18:
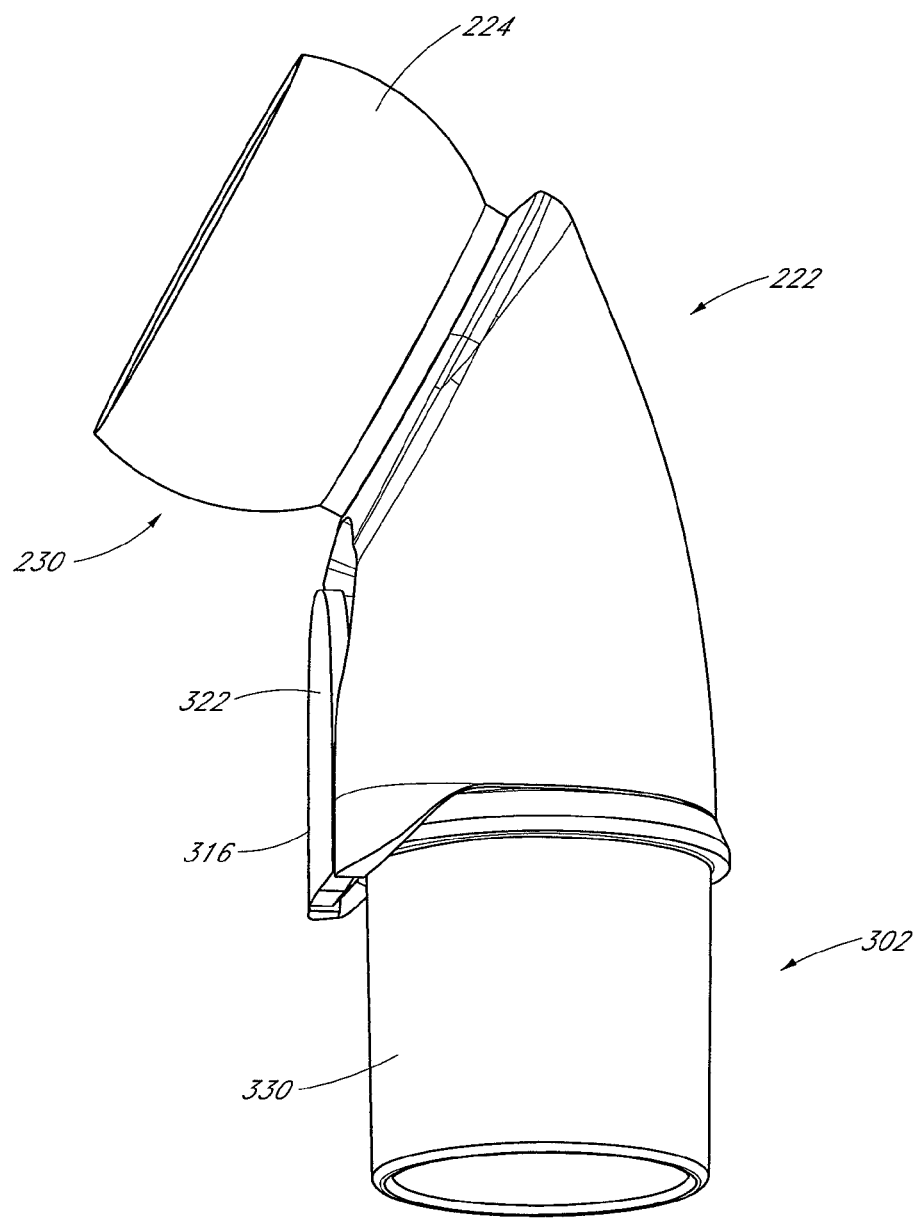
FIG. 18 is a side elevation view of the connection port assembly of FIG. 17.

With reference still to FIG. 14, the wall 212 comprises a contoured inner surface 214. The contoured surface 214 can be radiused to receive a ball end 220 of a swiveling elbow 222, such as that shown in FIG. 17. As better shown in FIG. 18, the ball end 220 has a contoured surface 224 that can be snap fit into the contoured surface 214 formed in the mask base 114. The connection between the two contoured surfaces 214, 224 allows the surfaces to slide relatively freely with each other such that the position of the swiveling elbow 222 can be easily changed. In some configurations, the elbow 222 could be configured for rotation or swiveling without having a ball-joint configuration.

With reference again to FIG. 13, the mask base 114 also comprises at least two pockets 230. The illustrated mask base 114 comprises two pockets 230. The pockets 230 recede into the mask base 114 and protrude rearward from the mask base 114. The pockets 230 are received within the recesses 140 of the mask seal clip 112. Overlying the further recesses 142 formed in the mask seal clip 112 are openings 232 that are defined by a surrounding wall 234.

The illustrated pockets 230 are formed such that one pocket 230 is formed on each lateral side of the mask base 114. The pockets 230 can be positioned to be symmetrical relative to the central plane CP, which plane substantially bisects the mask base 114. In some configurations, as shown in FIG. 15, the pockets 230 have an enlarged vertical dimension 240 relative to a transverse dimension 242. Similarly, as shown in FIG. 15, the openings 232 have an enlarged vertical dimension 244 relative to a transverse dimension 246.

In the illustrated mask base 114, the laterally inward portion of each pocket 230 comprises a support wall 250. The support wall 250 is positioned toward the center plane CP relative to normal to a base surface 248 of the pocket 230. Each of the pockets 230 is configured to receive a clip 252 (see FIG. 22). Once the clip 252 is installed within the pocket 230, the support wall 250 helps to limit rotation of the clip 252 relative to the pocket 230. Moreover, the large vertical dimension helps users to locate the pocket 230 with the clip 252 during installation.

Figure 22:
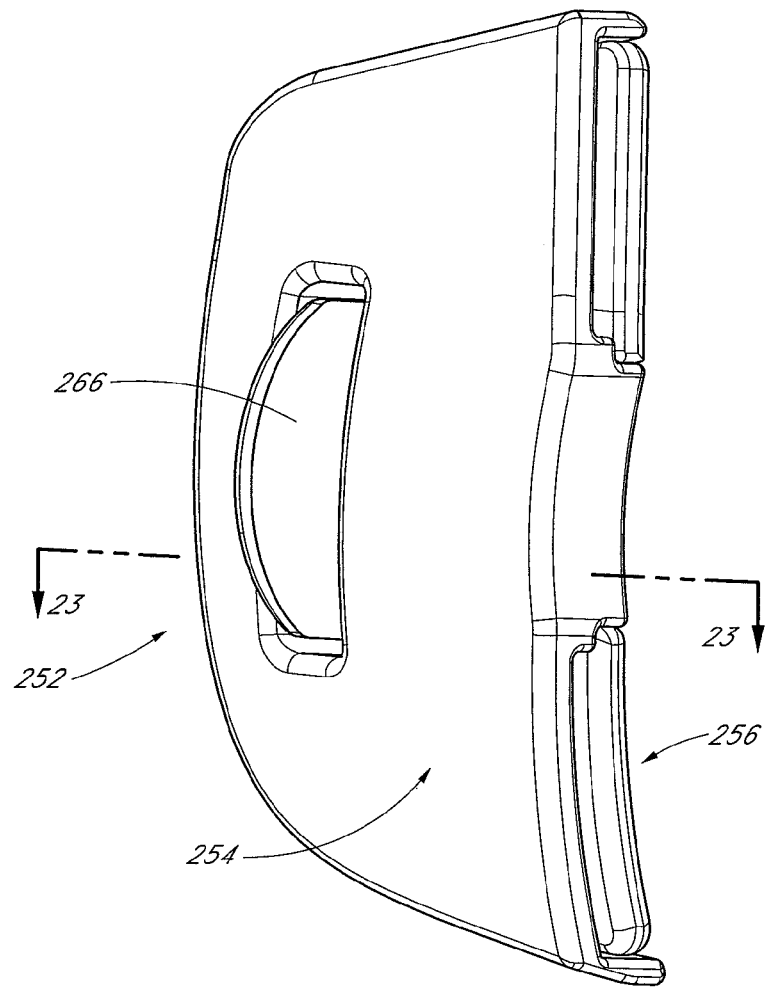
FIG. 22 is a perspective view of the clip assembly of FIG. 1.

With reference to FIG. 22, the clip 252 can have a two part construction: an outer cover 254 and an inner catch 256. Straps 260 can be secured to each clip 252 in any suitable manner. One suitable configuration is illustrated in FIG. 2. In some configurations, the straps 260 can be sandwiched between the outer cover 254 and the inner catch 256. In some configurations, loops or openings or holes could be provided on the clips 252 through which the straps 260 are threaded. Preferably, one clip 252 can be connected to both an upper strap and a lower strap of the headgear assembly 106. Such a configuration facilitates easy connection of the headgear assembly 106 to the full face mask assembly 102 and easy disconnection of the headgear assembly 106 from the full face mask assembly 102.

Figure 23:
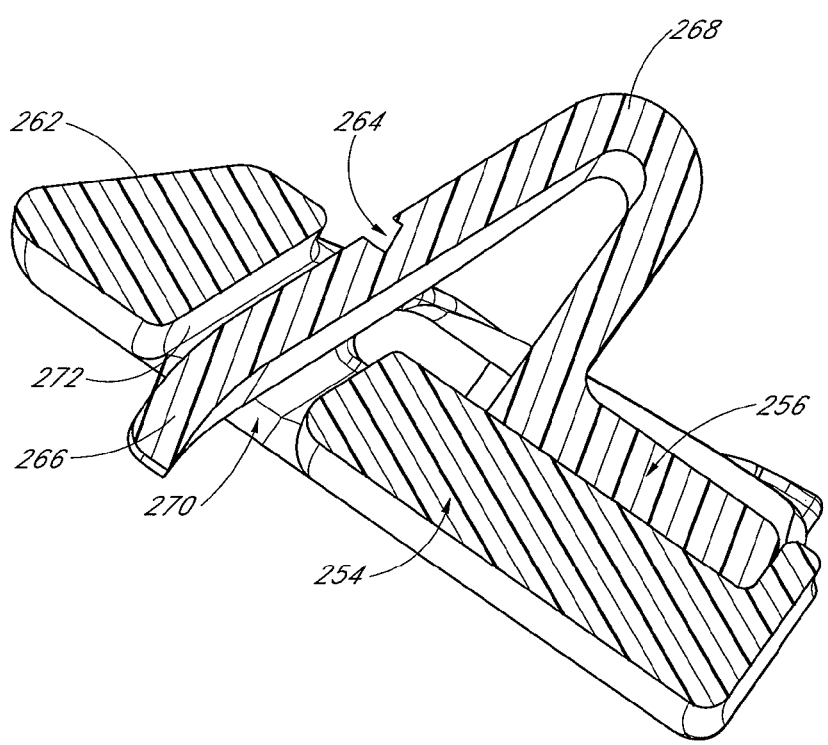
FIG. 23 is a sectioned view of the clip assembly of FIG. 22.

As shown in FIG. 23, the clip 252 comprises a sloping surface 262. The sloping surface 262 can be positioned on the outer cover 254. The sloping surface 262 cooperates with the support wall 250 to help orient the clip 252 relative to the pocket 203 of the mask base 114.

The clip 252 includes an interlock feature 264. The interlock feature 264 is configured for insertion into the opening 232 defined in the pocket 230 of the mask base 114. The interlock feature 264 can engage in a snap-fit manner with a tab 236 defined along the wall 234 that defines the opening 232 in the mask base 114, as shown in FIG. 13. Other manners of interlocking the clip 252 with the pocket 230 also can be used.

Referring to FIG. 23, the interlock feature 264 of the illustrated clip 252 comprises a U-shaped component 268 that terminates in a release lever 266. The U-shaped end 268 protrudes a sufficient distance to allow the connection with the tab 236 but does not protrude so far as to allow the bottom of the further recess 142 in the mask seal clip 112 to stop proper insertion of the interlock feature 264 into the opening 232. The U-shaped end 268 initially makes contact with a wall of the opening 232 during connection of the clip 252 to the mask base 114. In the illustrated configuration, the U-shaped end 268 contacts the wall 234 of the opening 232 during insertion and the wall 234 guides the clip 252 into position within the pocket 230. The opening 232, or one or more surfaces that define the opening 232, generally align the clip 252 relative to the mask base 114 during connection of the clip 252 to the mask base 114.

The end of the release lever 266 protrudes through an opening 270 defined by a wall 272. Preferably, the end of the release lever 266 protrudes through the opening 270 a sufficient distance to allow easy manipulation of the release lever 266. Moving the release lever 266 in manner that closes the U-shape of the interlock feature 264 allows the interlock feature 264 to be removed from engagement with the tab 236 in the wall 234 that defines the opening 232 in the mask base 112.

FIGS. 32-39 illustrate additional configurations of clip assemblies 252 that are configured to secure a mask assembly 102 to a user's head. The clip 252 of FIGS. 32 and 33, for example has a raised edge 400 (sometimes referred to as a finger tab 400) that enables the user to easily detach the headgear 106 from the mask assembly 102. The raised edges 400 are oriented such that the user may merely pull them rearwardly to pop the clips 252 off the mask base 114. Removing one or more clips 252 from the mask base 114 allows the mask assembly 102 to be easily removed from the user's head. The raised edge 400 provides a grasping point during attachment and removal of the headgear 106 with respect to the mask assembly 102. For example, the user's thumb and index finger may be placed on opposite sides of the raised edge 400 during removal of the clip 252 from the mask assembly 102. In addition, the user may grip the clip 252 and maintain the grip throughout the mask fitting process. This eliminates the need to grasp blindly for straps 260 during assembly. It also allows the user to attach the clip 252, remove it, and re-attach it while maintaining a grip on the raised edge 400.

Figure 32:
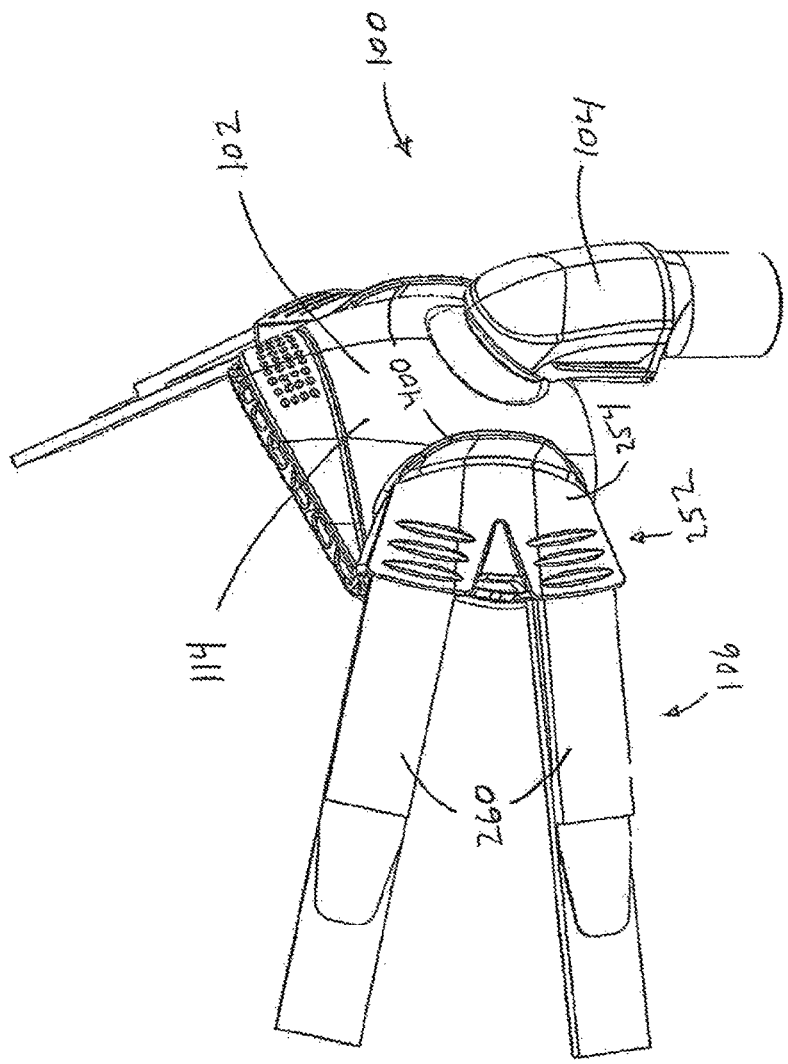
FIG. 32 is a perspective view of a mask assembly comprising a mask, clips, and straps.
Figure 33:
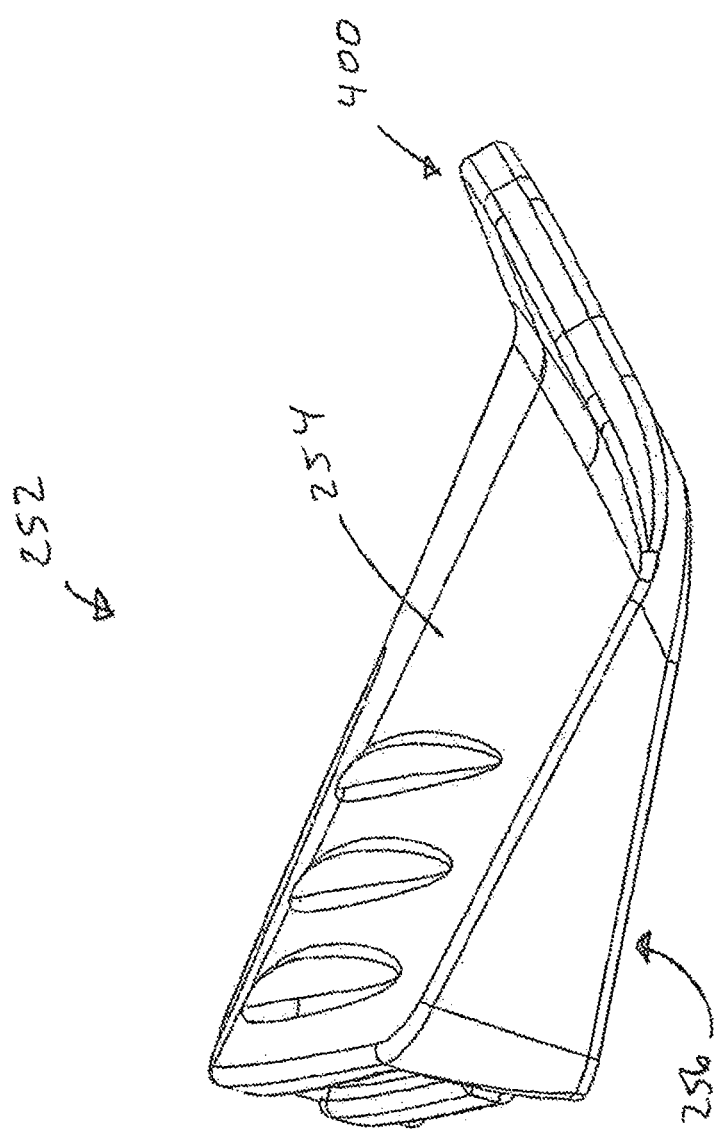
FIG. 33 is a side view of one of the two clips of FIG. 32.
Figure 34:
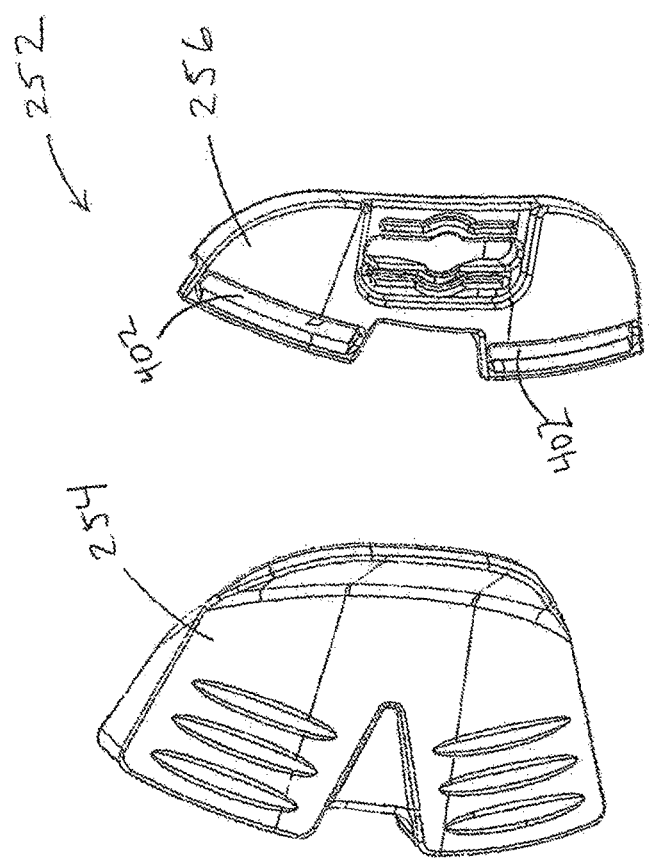
FIG. 34 is an exploded view of the clip of FIG. 33.
Figure 35:
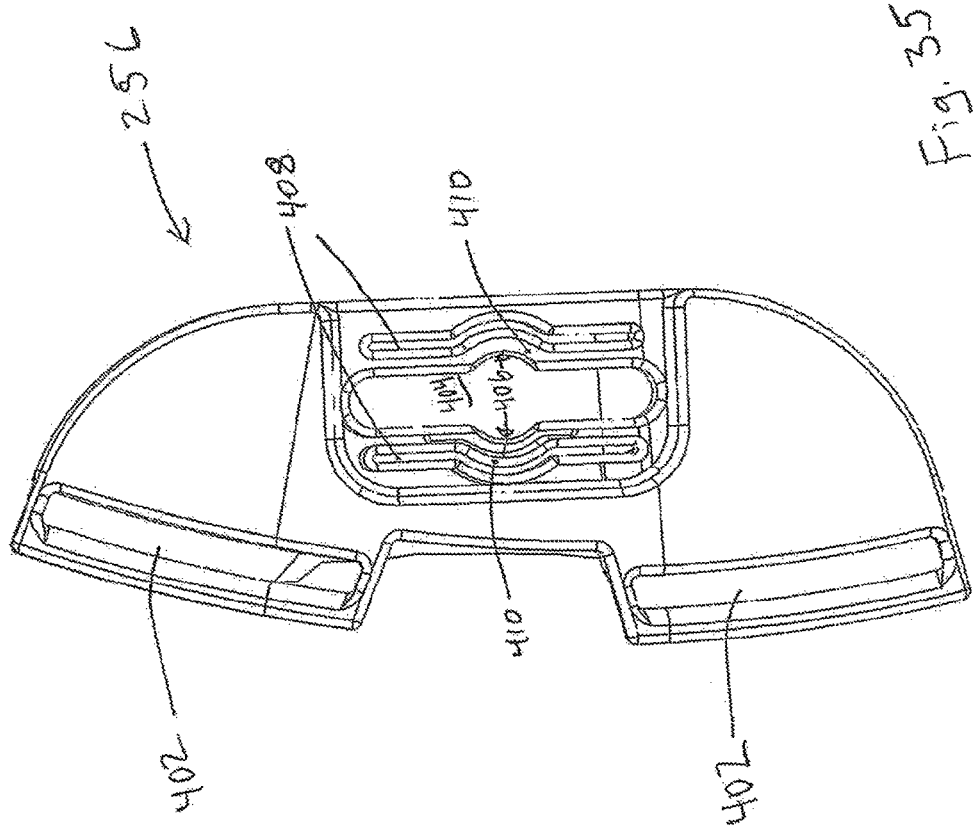
FIG. 35 is a top view of the inner catch of the clip of FIG. 33.

FIG. 34 shows an exploded view of the clip 252 of FIGS. 32 and 33. The clip 252 includes an outer cover 254 and an inner catch 256. The inner catch 256 includes one or more slots 402 to receive the distal end of the headgear straps 260. The inner catch 256 can also include several pressure bumps, such as those shown in connection with the configuration of FIGS. 38 and 39. The pressure bumps provide additional pressure against the outer cover 254 and inner catch 256, so that they are secured to one another. In one configuration, the headgear straps 260 are removable from the assembled clip 252.

Figure 38:
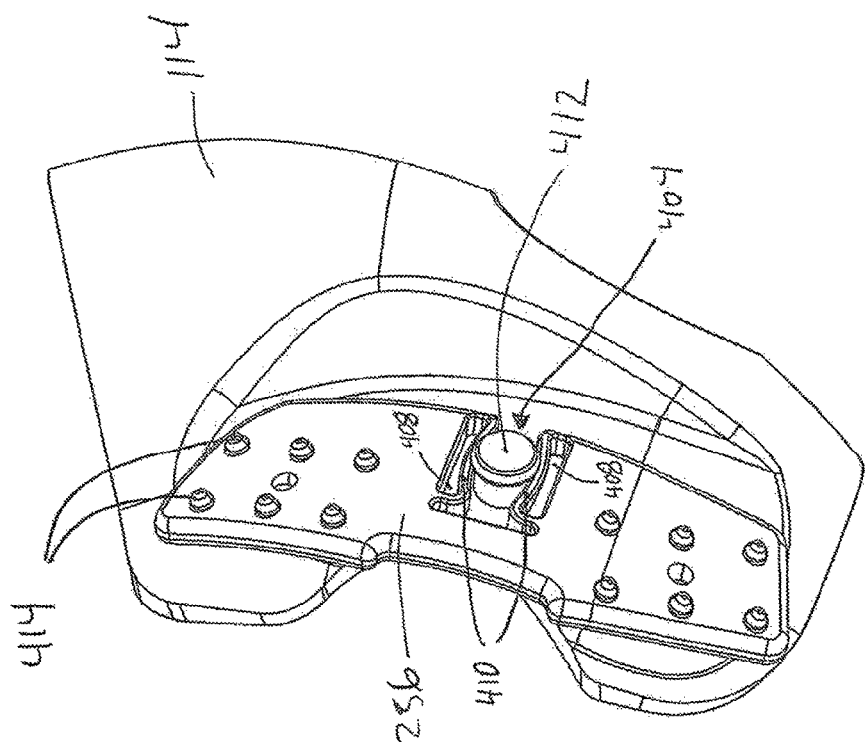
FIGS. 38-47 are additional configurations of clips and associated masks and mounting posts.

The inner catch 256 includes an elongated slot 404, as shown in FIG. 38. The slot 404 includes a circular opening 406 having a diameter larger than the width of the slot 404. The slot 404 and circular opening 406 can include chamfered recesses to help align the clip 252 to the mask assembly 102. The circular opening 406 facilitates attachment and removal of the clip 252 to the mask assembly 102, as will be discussed in greater detail below. Two channels 408 extend parallel to the sides of the slot 404, thereby defining slot walls 410 (sometimes referred to as clip levers) on either side of the slot 404. The channels 408 are sized to permit adequate flexing of the slot walls 410 during attachment and removal of the clip 252 from the mask assembly 102. In addition, the slot walls 410 extend along the longest dimension of the inner catch 256, towards top and bottom, which allows longer slot walls 410 to be employed. Longer slot walls 410 reduce the level of stress on the slot walls when fitting the clip over the mounting post.

Figure 36:
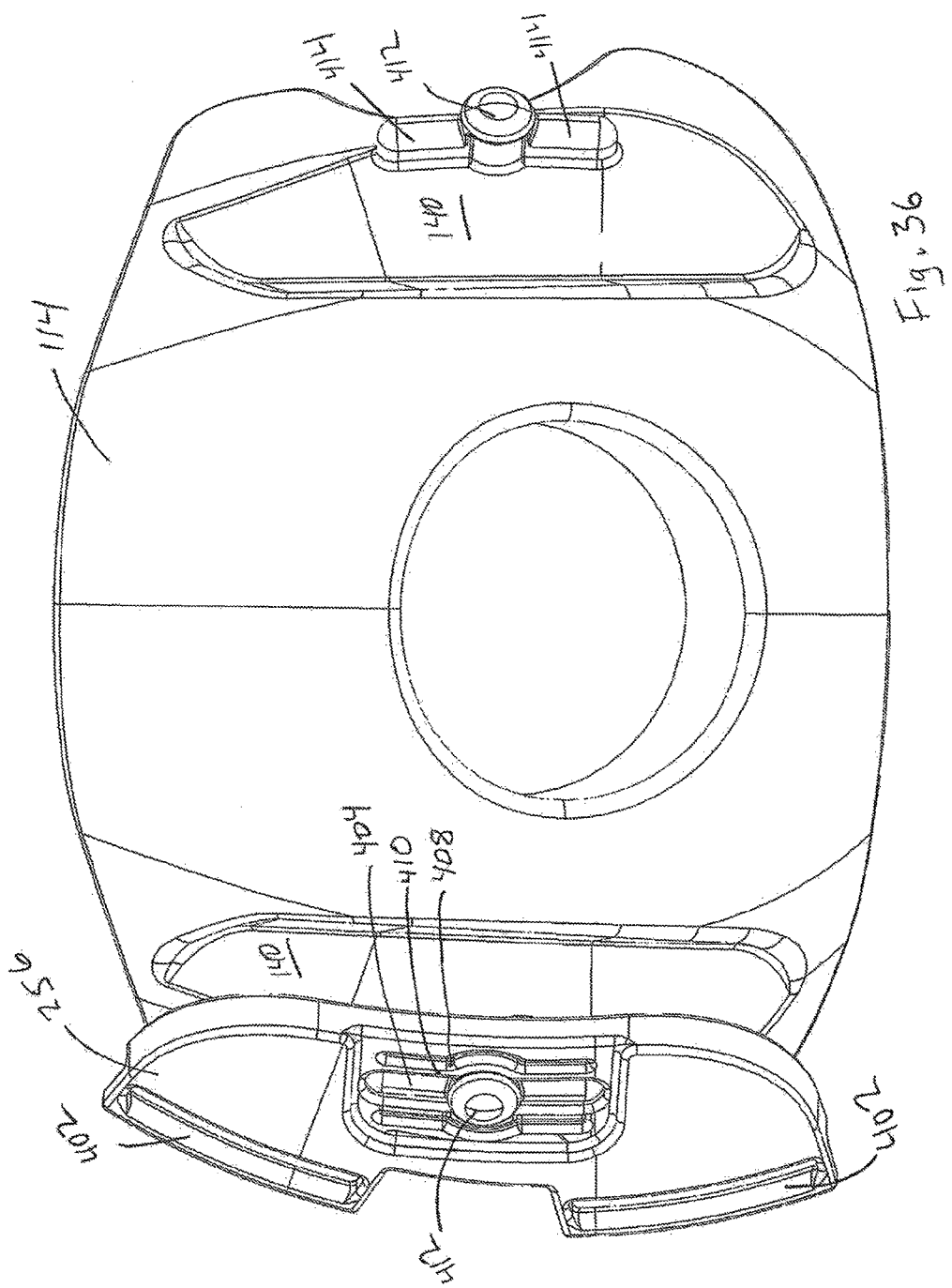
FIG. 36 is a front view of a mask base having two mounting posts, and one inner catch of a clip mounted to the left mounting post.

One configuration of a mask base 114 suitable for use with the clip 252 of FIGS. 32-35 is illustrated in FIG. 36. The mask base 114 includes two recesses 140 symmetrically positioned on opposite sides of the mask base 114. A mounting post 412 extends from the body of the mask base 114 within each recess 140. The mounting post 412 may be integrally formed with the mask base 114, or separately formed and secured to the mask base 114. The mounting post 412 can have a mushroom-shaped configuration to secure the clip 256 to the mask base 114 once the user snaps the clip 256 in place. The rounded top of the bulbous mushrooms-shaped post 412 helps locate and orient the central hole 406. As the clip 252 is pressed onto the post 412, the slot walls 410 deflect outwardly, away from the post 412. Once the head of the post 412 clears the edge of the slot wall 410, the slot walls 410 snap back to their original position, thereby providing tactile and sometimes audible feedback that the clip 252 is properly attached to the mask assembly 102.

The mounting post 412 can also comprise an elongated, elliptical, elevated portion 414 (sometimes referred to as a lug or wing) that is sized to mate with the elongated slot 404 of the inner catch 256. The elongated, elevated portion 414 comprises a chamfered edge to help properly align the head gear 106 with respect to the mask assembly 102. The portion 414 also prevents the clip 252 from rotating with respect to the mask assembly 102. This helps assure constant tension on the headgear straps 260 while the user sleeps.

Figure 37:
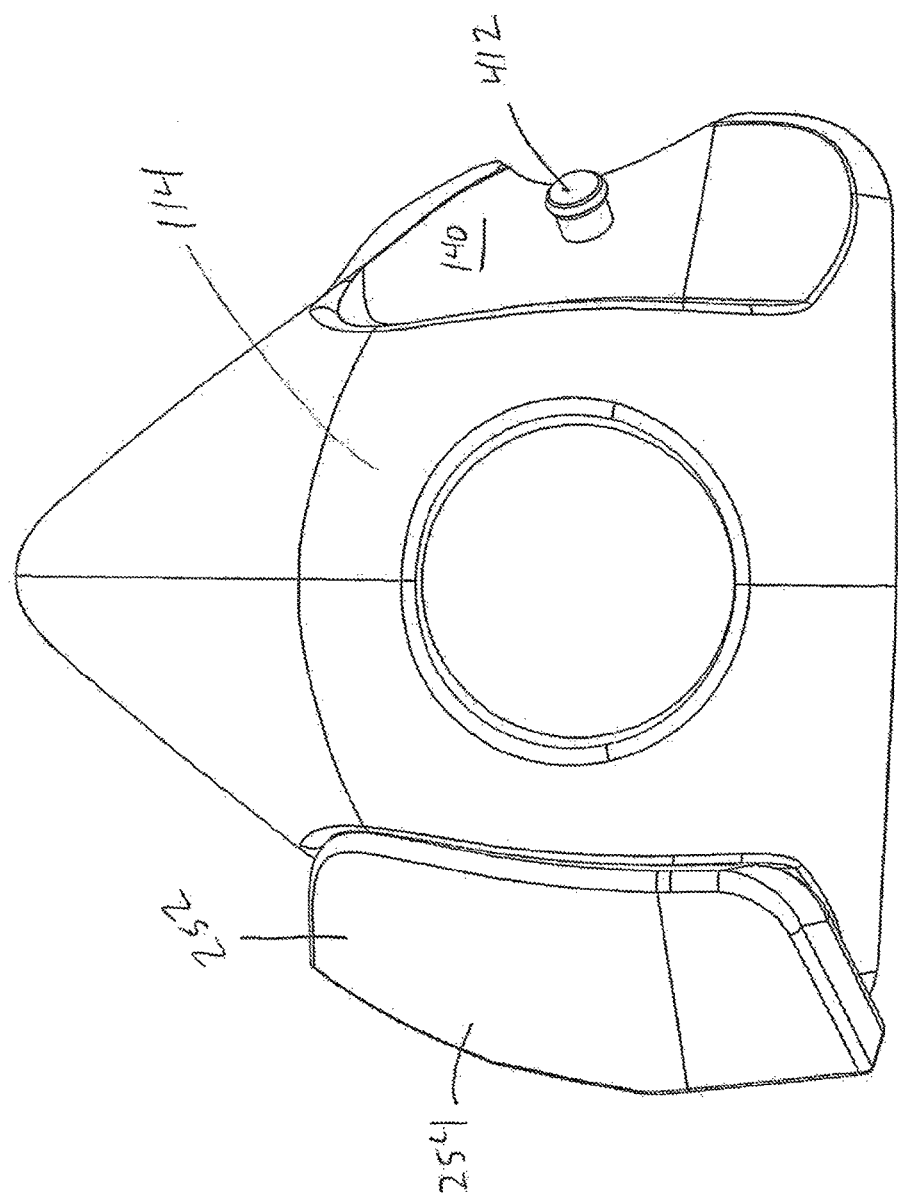
FIG. 37 is a front view of another configuration of a mask base having two mounting posts, and another configuration of a clip mounted to the mask base's left mounting post.
Figure 39:
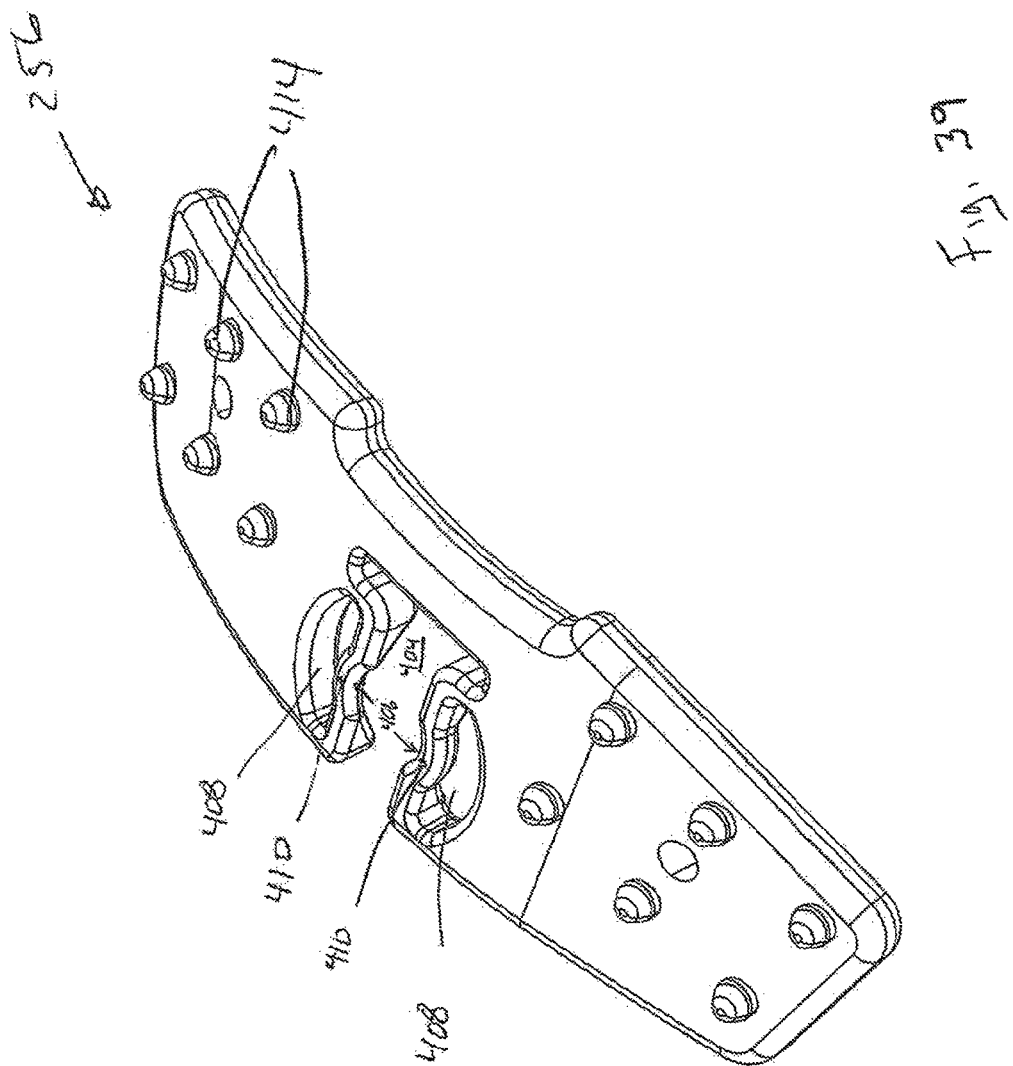

FIG. 37 illustrates a partial assembly of yet another configuration to secure a clip 252 to a mask base 114 of a mask assembly. The clip 252 sits within a recess 140 of the mask base 114. A cylindrical, button-head post 412 extends from the surface of the mask base 114 within the recess 140. The post 412 allows slight rotation of the clip 252 when attached thereto due to its cylindrical configuration. However, as shown in FIGS. 38 and 39, the slot 404, channels 408 and slot walls 410 extend along the shorter planar direction of the inner catch 256, towards its front and back ends.

The inner catch 256 also includes several pressure bumps 414. As discussed above, the pressure bumps provide additional pressure against the outer cover 254 and inner catch 256, so that they are secured to one another.

Figure 43:
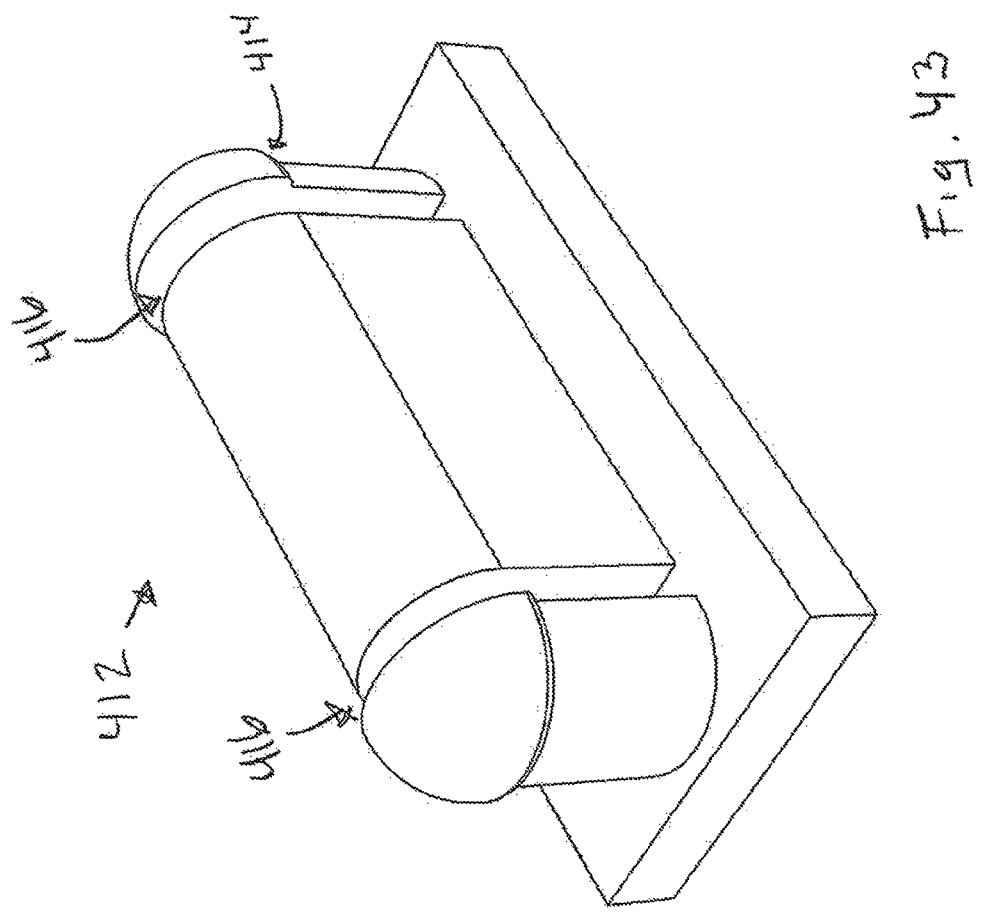
Figure 44:
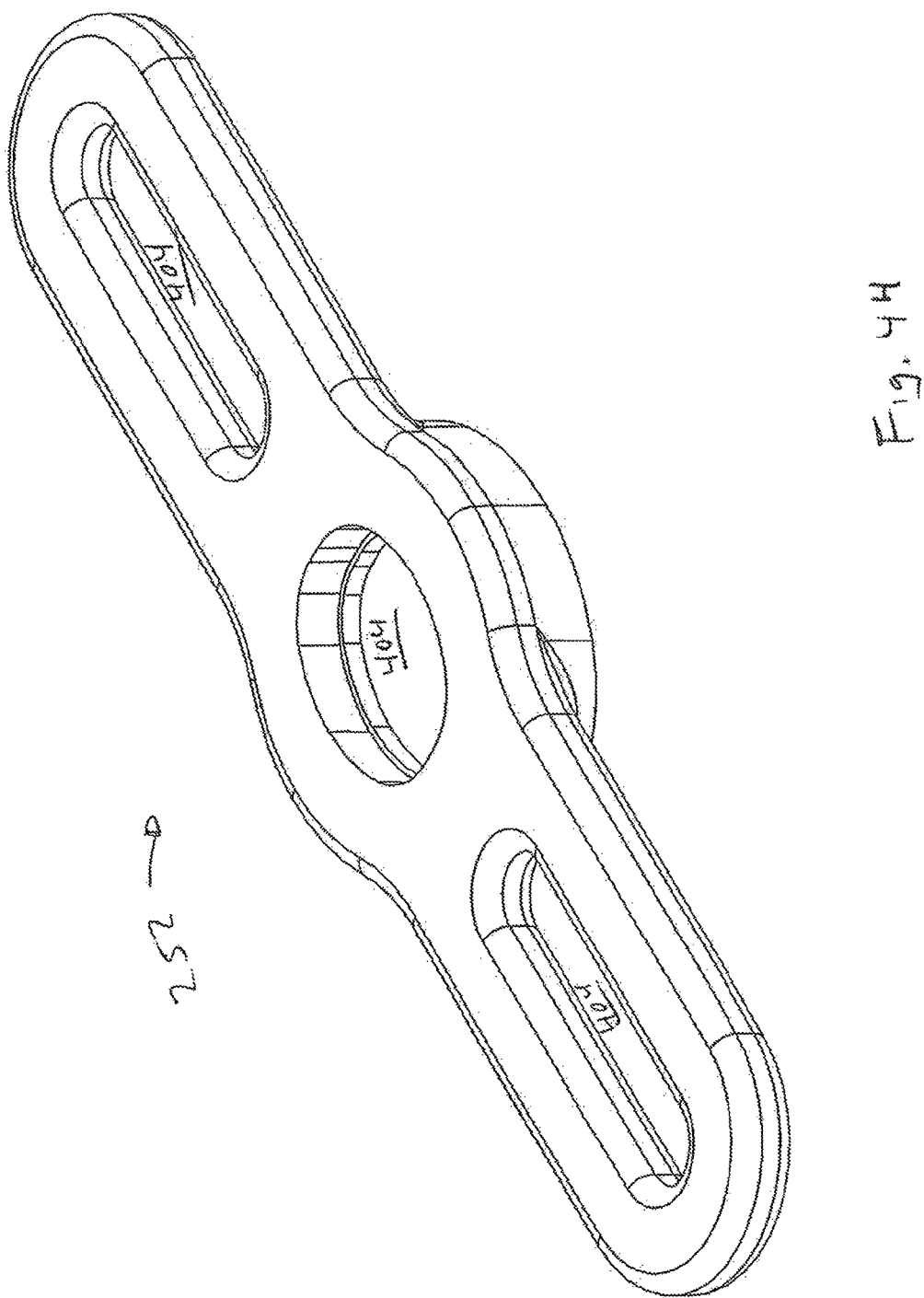
Figure 45:
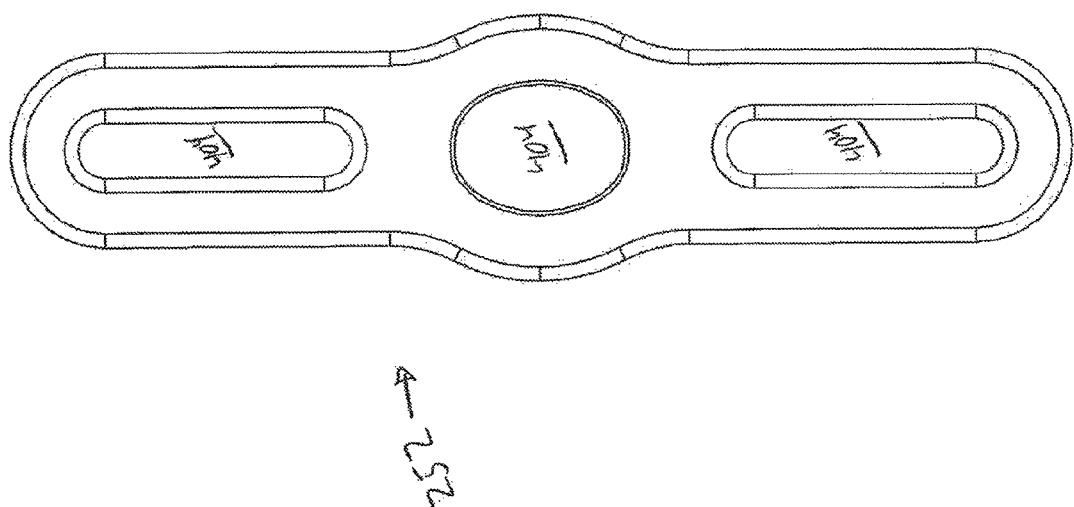
Figure 46:
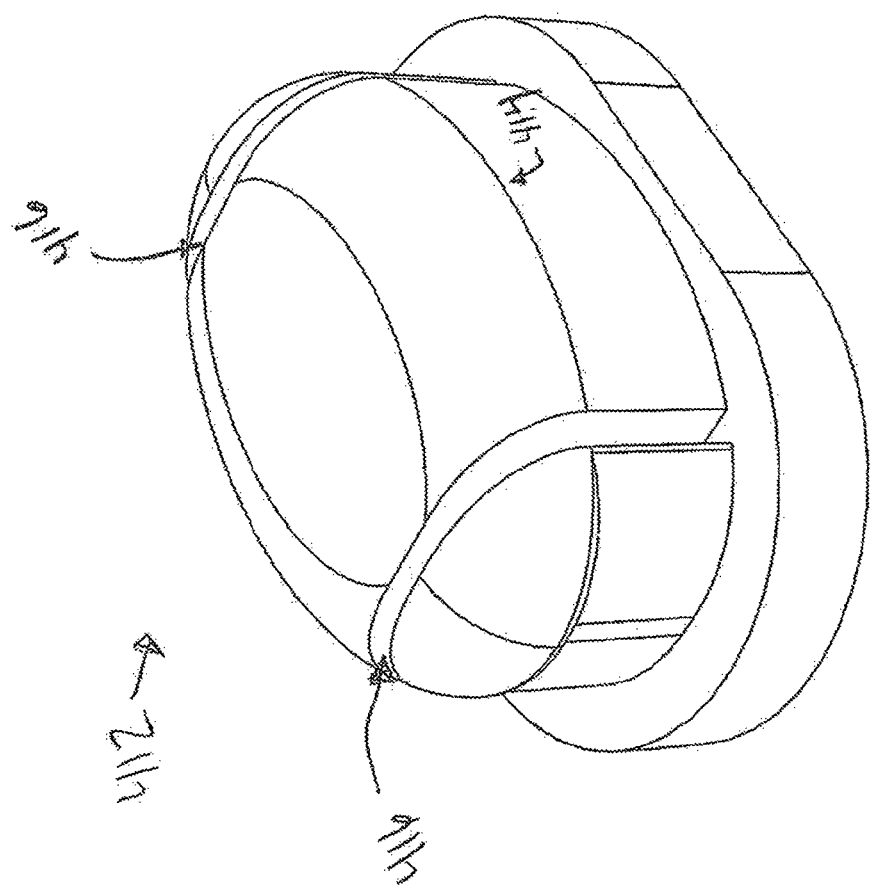
Figure 47:
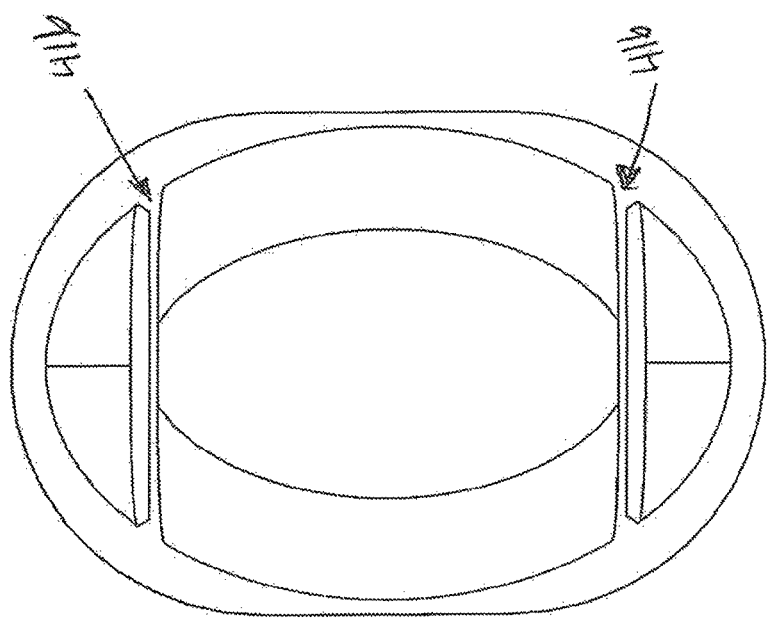
Figure 48:
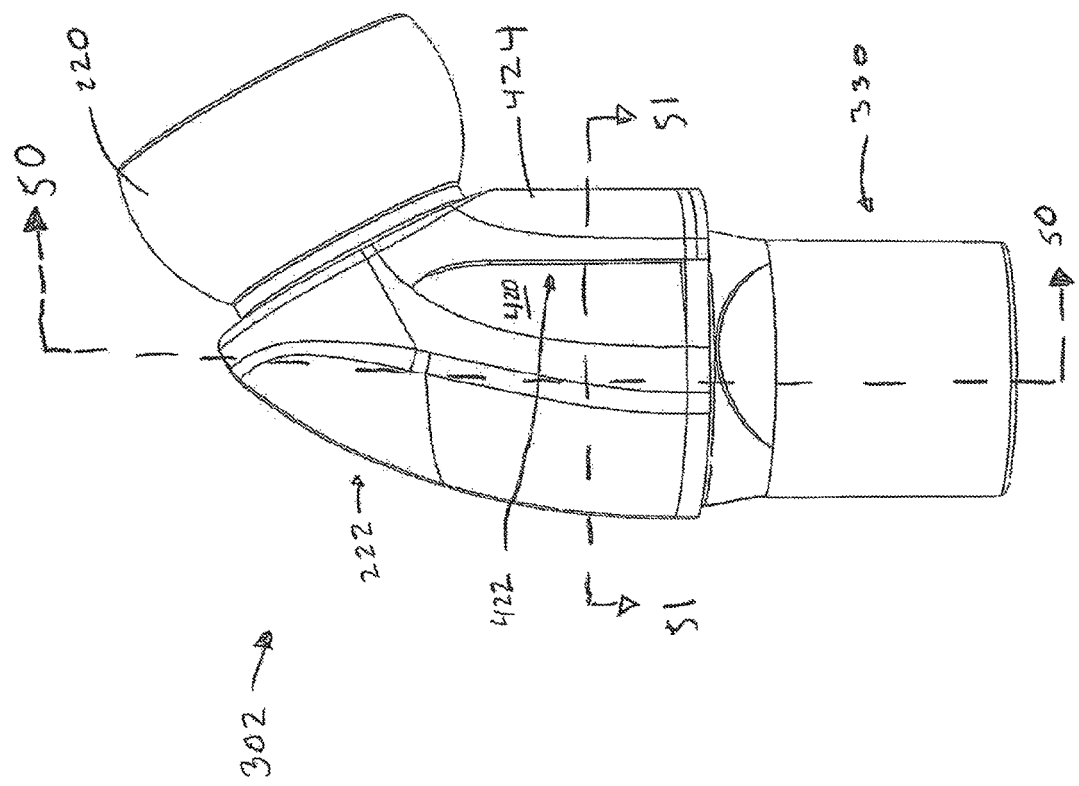
FIG. 48 is a side view of another configuration of a swivel assembly.

Additional configurations of a clip 252 are illustrated in FIGS. 40-47. The clip 252 of FIG. 40 includes three elongated, elliptical slots 404 and a finger tab 400. The finger tab 400 is used to create a lever to release the clip 252 from a mask assembly 102. The central slot 404 is sized to receive a mounting post 412 that extends from the outside surface of the mask body. One such suitable mounting post 412 is illustrated in FIG. 43. The mounting post 412 includes a ridge 414 and two slots 416. As the clip 252 is pressed onto the mounting post 412, the outer portions of the post 412 flex towards each other due to the spacing provided by the slots 416. Once the ridge 414 clears the upper surface of the clip 252, the mounting post 412 snaps back to its original position, and the ridge 414 locks the clip 252 in place.

A similar configuration is shown in FIGS. 44-47. The clip 252 of FIG. 45 does not include a finger tab and its central opening 404 has a rounder, more elliptical shape than the elongated slots of FIGS. 40-44.

All of the foregoing configurations simplify the procedure for securing the mask assembly 102 to the user's head. For example, the clips 252 allow the headgear 106 to open up so that it is not a closed loop. By opening up, the headgear 106 may be swung around the head rather than forcing the user to pull his head through it.

With reference to FIG. 2, in addition to the straps 260, the headgear assembly 106 also comprises a back strap 280 and a top strap 282. Other head gear assemblies also can be used. The back strap 280 extends around the back of the head of the user U at a location generally above a nape of the neck but generally below the occipital protuberance. At a location rearward of the ear of the user, the back strap 280 forks into an upper arm 284 and a lower arm 286. The upper arm 284 arcs upward to a location above the ear of the user and then arcs downward to a location generally forward of the ear of the user. The lower arm 286 arcs downward to a location generally below the ear of the user and extends slightly forward of the ear.

The straps 260 can be connected to the back strap 280 in any suitable manner. In the illustrated configuration, the straps 260 connect to the upper arm 284 and the lower arm 286 respectively. Preferably, the upper arm 284 and the lower arm 286 are more rigid than the straps 260 such that the arms 284, 286 generally maintain shape as the headgear assembly 106 is being donned. In some configurations, each of the upper arm 284 and the lower arm 286 supports its own weight. In some configurations, each of the upper arm 284 and the lower arm 286 is structured to be tangle-free during donning. For example, the arms 284, 286 have sufficient torsion stiffness to reduce the likelihood of twisting when being put on.

Preferably, the straps 260 connect to at least one of the upper arm 284 and the lower arm 286 at a location forward of the ear. Such a configuration helps the user to locate the straps 260 without much difficulty. In addition, because the straps 260 in the illustrated configuration are embedded into the clips 252, the ends of the upper arms 284 and the lower arms 286 can comprise slots 290, 292 such that the straps 260 can be threaded through the slots 290, 292. In addition, the straps 260 can comprise an adjustment mechanism 294, such as a Velcro or buckle configuration. The adjustment mechanism 294 allows a force between the mask seal 110 and the face of the user U to be adjusted. Any suitable adjustment mechanism 294 can be used.

As shown in FIG. 2, the top strap 282 preferably is flexible and has an adjustable length. The top strap 282 connects to the upper arms 284 through a slot 296 and reduces the likelihood of the upper arms 284 sliding down the head of the user and contacting the ears of the user. Preferably, the top strap 282 connects to the upper arms 284 at a location generally above the ears of the user.

Advantageously, as shown in FIGS. 1 and 2, the straps 260 exert a force in the direction of the arrow F while they connect to the mask base 114 by movement in the direction C, which direction is generally normal to the direction of the force F. In other words, the straps 360 are tensioned by pulling forward and the clips 252 are connected to the mask base 114 by movement in a direction normal to the forward pull. Such a configuration eases securement of the interface 100 on the face of the user.

Figure 29:
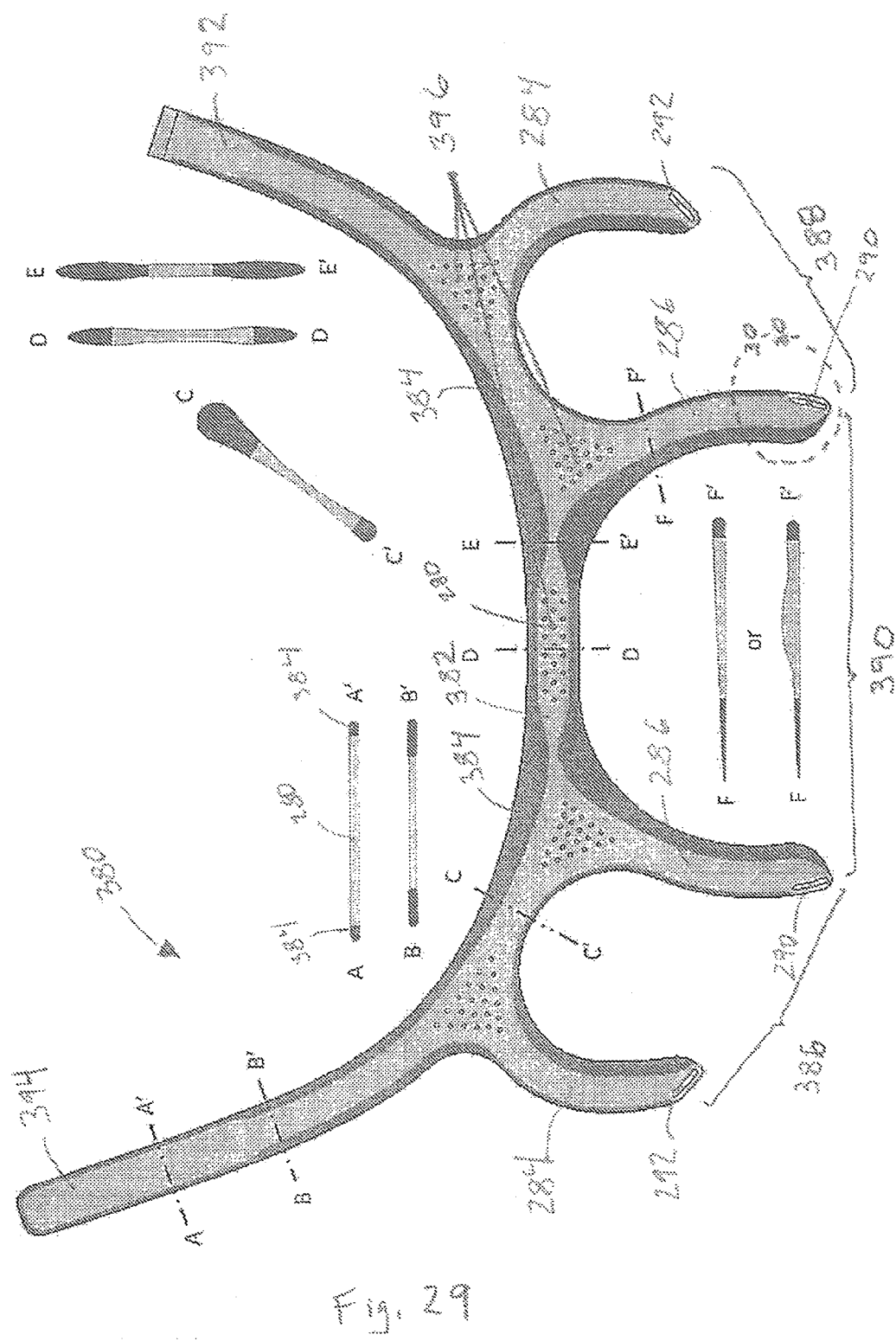
FIG. 29 is a perspective view a backbone compatible with the headgear assembly of FIGS. 1 and 2.

In another configuration, the headgear assembly 106 includes a semi-rigid headgear 380 (as shown in FIG. 29) to secure the mask assembly 102 to the user's head. The semi-rigid headgear 380 is formed as a composite structure comprising a semi-rigid strap 382 that is joined to a soft edging 384. For example, the soft edging 384 can be bonded to the semi-rigid strap 382 by plastic overmolding or by use of an adhesive. As shown in FIG. 29, the soft edging 384 can be butt-joined to the semi-rigid strap 382, without the soft edging 384 overlapping the semi-rigid strap 382, to maintain the continuous profile of the semi-rigid headgear 380. The semi-rigid strap 382 defines and maintains the semi-rigid headgear shape as tension is applied from the straps 260 to pull the mask assembly 102 towards the user's head. In other words, the semi-rigid strap 382 is sufficiently rigid along its planar axis to prevent its upper and lower arms 284, 286 from overly deforming under tension. The semi-rigid strap 382 can be made from a variety of rigid or semi-rigid materials, including plastic or metal. In some configurations, the semi-rigid strap 382 is made from PVC.

Especially in connection with a semi-rigid headgear assembly, it has been found that the shape holding, or self-supporting nature, can result in an overall assembly that is intuitive to fit. In particular, where the connection and/or headgear members are self-supporting such that they maintain a three-dimensional form, the headgear can be fitted in the correct orientation with very little if any instruction. In a self-supporting arrangement, the tendency of the straps to not tangle also reduces the time taken to fit the overall assembly.

As used herein, the term "semi-rigid" is used to denote that the headgear assembly is sufficiently stiff such that the headgear assembly 380 can assume a three-dimensional shape with dimensions approximating the head of the patient for which the headgear is designed to fit while also being sufficiently flexible to generally conform to the anatomy of the patient. For example, some of the other components (e.g., arms or straps) of the headgear assembly 380 may also be partially or wholly "semi-rigid" such that the components are capable of holding a three-dimensional form that is substantially self-supporting. A "semi-rigid" headgear assembly is not intended to mean that each and every component of the headgear assembly is necessarily semi-rigid. For example, the substantially three-dimensional form that the self-supporting headgear assembly 380 may assume may relate primarily to the rear and top portions of the headgear assembly 380. In addition, the semi-rigid headgear assembly 380 may include semi-rigid regions that extend forward of the ears and above the ears when placed on the head of the patient.

The left and right upper and lower arms 284, 286 may be formed of a semi-rigid material, as well. Where used herein, the semi-rigid materials may include molded plastic or sheet materials that include but are not limited to homogeneous plastic materials and bonded non-woven fiber materials.

In some configurations, one or more of arms or straps are formed of a substantially inelastic material. The arms or straps can be formed of a semi-rigid, self-supporting material such that the semi-rigid headgear assembly 380 can assume a substantially three-dimensional shape and generally does not tangle. In some configurations, the material can comprise a laminate structure of both conformable and semi-rigid portions, for example but without limitation. The semi-rigid strap 382 may be of a self-supporting, resilient, substantially inelastic material, such as Santoprene, polyolefin, polypropylene, polyethylene, foamed polyolefin, nylon or non-woven polymer material for example but without limitation. In some configurations, the semi-rigid strap 382 is formed from the polyethylene or polypropylene families. The material can be a low density polyethylene such as Dowlex 2517, which is a linear low density polyethylene that has a yield tensile strength of 9.65 MPa, a break tensile strength of 8.96 MPa, and a flexural modulus—2% secant of 234 MPa. The semi-rigid strap 382 preferably is formed of a material such that the semi-rigid headgear 380 is substantially shape-sustaining under its own weight regardless of its orientation. In some configurations, the semi-rigid strap 382 does not stretch more than approximately 6 mm under a 30 N tensile load. In some configurations, the semi-rigid strap 382 does not stretch more than approximately 3 mm under a 30 N tensile load.

In some configurations, the semi-rigid strap 382 is formed from non woven polyolefin (NWP), which is bonded (e.g., overmolded or laminated) with a polyolefin. In such configurations, the overmolded polyolefin material provides the principle shape sustaining properties. In addition, the softer NWP material is adapted to contact the skin and provide a desired comfort level. Furthermore, the NWP material may assist in providing the desired load bearing properties, such as the desired tensile load bearing properties.

The semi-rigid headgear 380 is generally formed of a semi-rigid material. Where used herein, the semi-rigid materials may include molded plastic or sheet materials that include but are not limited to homogeneous plastic materials and bonded non-woven fiber materials. The upper and lower arms 284, 286 also include such semi-rigid materials, as the arms 284, 286 are formed integrally with and are portions of the semi-rigid headgear 380. Preferably, the right and left lower arms 286 are formed as an integrated component that, in use, will extend around the back of the head and above the neck of the patient.

A soft edging 384 covers or attaches to at least a portion of the periphery of the semi-rigid strap 382. In one configuration, the soft edging 384 does not cover the front or rear faces of the semi-rigid strap 382. For example, the thicknesses of the soft edging 384 and semi-rigid strap 382 can be the same at the location where they are joined together.

The soft edging 384 provides a soft, comfortable interface between the periphery of the semi-rigid strap 382 and the user's skin. The soft edging 384 can be made from a variety of soft materials, including but not limited to a plastic, an elastomer, silicone or thermoplastic polyurethane (TPU) plastic. The soft edging 384 can have a Shore hardness in the range of 10-80 Shore A.

As used herein with respect to headgear and straps, "soft" is used to describe a hand of the material, which means the quality of the material assessed by the reaction obtained from the sense touch. In addition, as used herein with respect to headgear and straps, "conformable" is used to describe the ability of the material to conform to the anatomical features of the patient (e.g., around a facial feature). In particular, a strap including at least an element of "soft" and/or "conformable" material also may be "semi-rigid" and/or axially inelastic.

The soft edging 384 can have a uniform thickness, or in some configurations, an uneven thickness. For example, in some configurations the soft edging 384 is the same thickness as the semi-rigid strap 382. In other configurations, the soft edging 384 is thinner than the semi-rigid strap 382, forms a bulbous end to the semi-rigid strap 382, or is simply thicker than the semi-rigid strap 382. A variety of cross-sectional views of the semi-rigid headgear 380 are shown in FIG. 29. Each cross-sectional view (A-A' through F-F') shows one possible configuration of semi-rigid strap 382 and soft edging 384 thicknesses, which may be combined as desired. For example, any one particular soft edging 384 thickness and shape could apply to a portion or the entire semi-rigid strap 382, or may be combined with any other particular covering thickness and shape shown in FIG. 29.

Many other thickness configurations may be provided, as well. In addition, material thickness may be symmetrically or asymmetrically applied to the semi-rigid strap 382. For example, cross-sectional views C-C' and F-F' are shown as asymmetric; however, in other configurations the thickness of either end the soft edging 384 is symmetrically applied to the semi-rigid strap 382. In some configurations the semi-rigid strap 382 is selectively thickened to provide extra rigidity and support. For example, the second of the two configurations illustrated as cross-sectional view F-F' has such a thickening. Finally, in some configurations, venting through-holes 396 are provided throughout the semi-rigid headgear 380 (such as on the semi-rigid strap 382, as shown in FIG. 29, or on soft edging 384) to provide ventilation and sweat management.

When laid flat, as shown in FIG. 29, the semi-rigid headgear 380 defines three C-shaped, arcuate regions 386, 388, 390. Two ear-surrounding regions 386, 388 are defined by upper and lower arms 284, 286, and a rear region 390 is defined by lower arms 286 and the back strap portion 280. The semi-rigid headgear 380 is flexible enough to bend to adapt to the shape of the user's head, such that the ear-surrounding regions 386, 388 at least partially surround or encircle the user's ears, and the rear region 390 at least partially surrounds or encircles the back of the user's head, above the neck.

The curvature of each arm 280, 284, 286 can be selected to provide a comfortable fit and to facilitate application and removal of the semi-rigid headgear 380 from the user's head. For example, in the illustrated configuration, the upper arms 284 have a concave curvature and the lower arms 286 have a convex curvature with respect to the opening in the upper ear surrounding arcuate regions 386, 388. The back strap portion 280 and the lower arms 286 all have a concave curvature with respect to opening in the neck surrounding arcuate region 390. These curvatures facilitate application and removal of the semi-rigid headgear 380 from the user's head by, for example, providing openings to the arcuate regions sized and oriented to easily fit over a user's neck and ears.

The configuration of FIG. 29 utilizes integrated crown straps comprising first and second crown arms 392, 394 to secure the semi-rigid headgear 380 to the user's head. Once the semi-rigid headgear 380 is positioned to partially surround the user's head, the first and second crown arms 392, 394 are brought into contact with one another to secure the semi-rigid headgear 380 in place. Any of a variety of mechanisms can be provided with the first and second crown arms 392, 394 to enable them to attach to one another. For example, in some configurations, a hook-and-loop fabric (e.g., Velcro), or one or more snaps or clips can be used to attach the first and second crown arms 392, 394 to one another.

The crown straps extend laterally over the top of the skull in line with the ears. When the crown straps extend in this manner and the arcuate regions 386, 388 are positioned to partially encircle the user's ears, the back strap 280 of the semi-rigid headgear 380 should locate on or below the inion. The user's inion is the most prominent projection of the occipital bone at the posteroinferior portion of the skull. In other words, the inion is the highest point of the external occipital protuberance. The semi-rigid headgear 380 can be positioned on the user's head according to any of the configurations described in the attached Appendix, which forms an integral part of the present disclosure and is bodily incorporated, herein.

For example, the back strap portion 280 is adapted to engage with the rear of head of the user. Preferably, the back strap portion 280 is adapted to engage with the head at a location on or below the external occipital protuberance. The back strap portion 280 spans the distance around the back of the head and extends to each side of the head. In some configurations, the back strap portion 280 comprises a longitudinal center that is adapted to be located about 25 degrees below a horizontal plane that extends through the ear canal of the patient.

On either side of the head, the semi-rigid headgear 380 extends upward and downward into left and right side regions that form arcuate regions 386, 388. The side regions are adapted to extend behind the ears of the patient. Preferably, the side regions also are adapted to extend behind the mastoid processes of the patient. Each of the left and right side regions of the semi-rigid headgear 380 extends into or comprises an arched portion 386, 388. The arched portions 386, 388 bend forward. The arched portions 386, 388 are adapted to extend around the respective ears of the patient. Preferably, each of the arched portions 386, 388 terminates at a respective termination portion. The termination portions preferably are adapted to be located forward of the ears of the patient. In some configurations, the side regions and the arched portions 386, 388 of the semi-rigid headgear 380 do not include a soft inner padding portion but may comprise a self-supporting, resilient material that is in direct contact with the head/hair of the patient.

The top portion of the semi-rigid headgear 380 connects the arched portions 386, 388 together. The top portion can be positioned forward of the ears in some configurations. Preferably, the top portion is positioned generally vertical from the ears. More preferably, a longitudinal center of the top portion is adapted to be spaced more than 13 mm, preferably between 13-100 mm, rearward of a vertical plane that intersects the ear canals. In some configurations, the top portion comprises a first segment 392 and a second segment 394 with the first segment 392 and the second segment 394 combining to form the top portion. The first segment 394 extends upward from an apex of the left arched portion 386 while the second segment 392 extends upward from an apex of the right arched portion 388. Preferably, the top portion is formed of a self-supporting and semi-rigid material. In some configurations, the top portion does not include any backing, including a soft padded backing layer.

Figure 30:
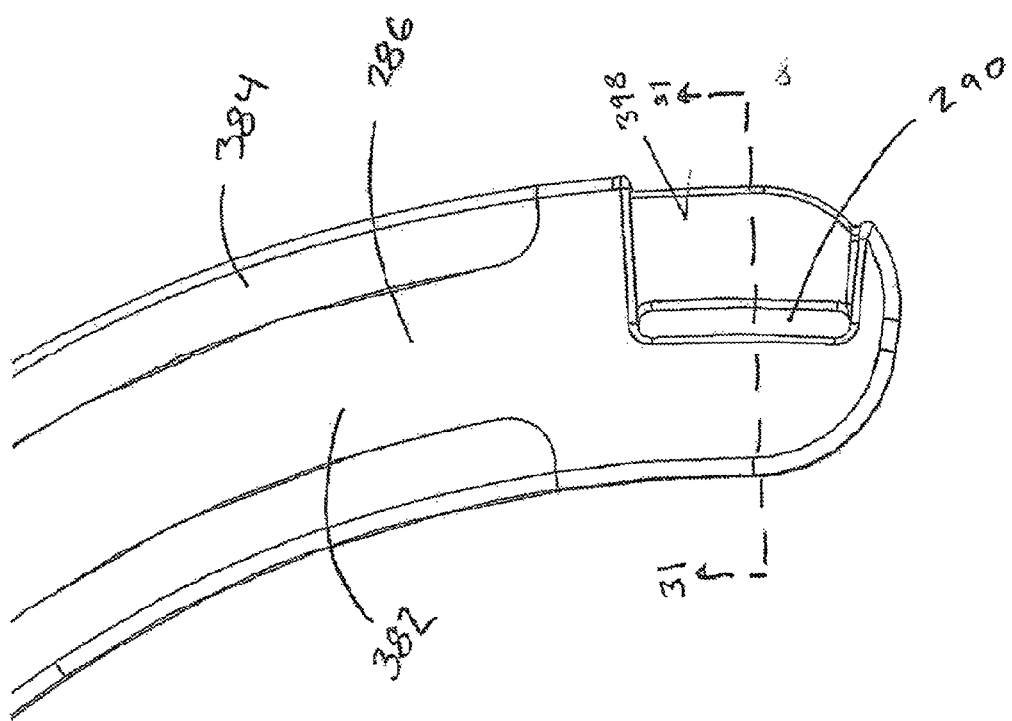
FIG. 30 is an enlarged view of the end region of a lower arm of FIG. 29.
Figure 31:
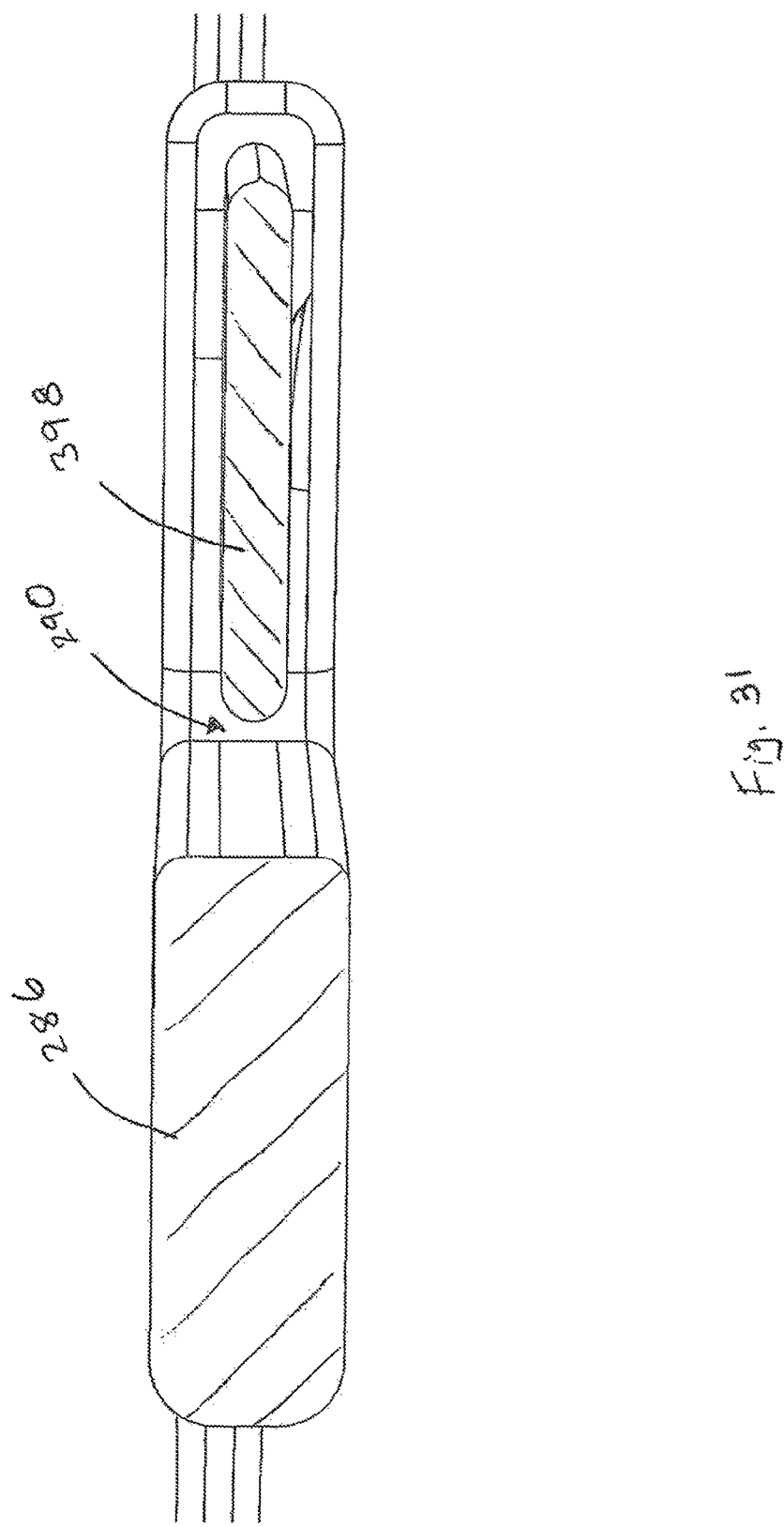
FIG. 31 is an enlarged cross-sectional view of the end region of FIG. 30.

Each of the upper and lower arms 284, 286 comprises a slot 292, 290 near each arm end. Each slot is configured to receive straps 260 from the mask assembly 102, as shown in FIG. 2. In addition, the portion 398 of the semi-rigid headgear 380 covered by straps 260 is thinner than the corresponding arm 284, 286 in order to accommodate the thickness of the strap 260. For example, as shown in FIGS. 30 and 31, the semi-rigid headgear portion 398 is thinner than the arm 286. The portion 398 is dimensioned such that when the strap 260 is inserted into the slot 290 and tensioned, its thickness will not extend beyond the arm 286. By maintaining the thickness of the strap 260 and the portion 398 less than the thickness of the arm 286, the strap 260 does not irritate the user when worn.

Figure 52:
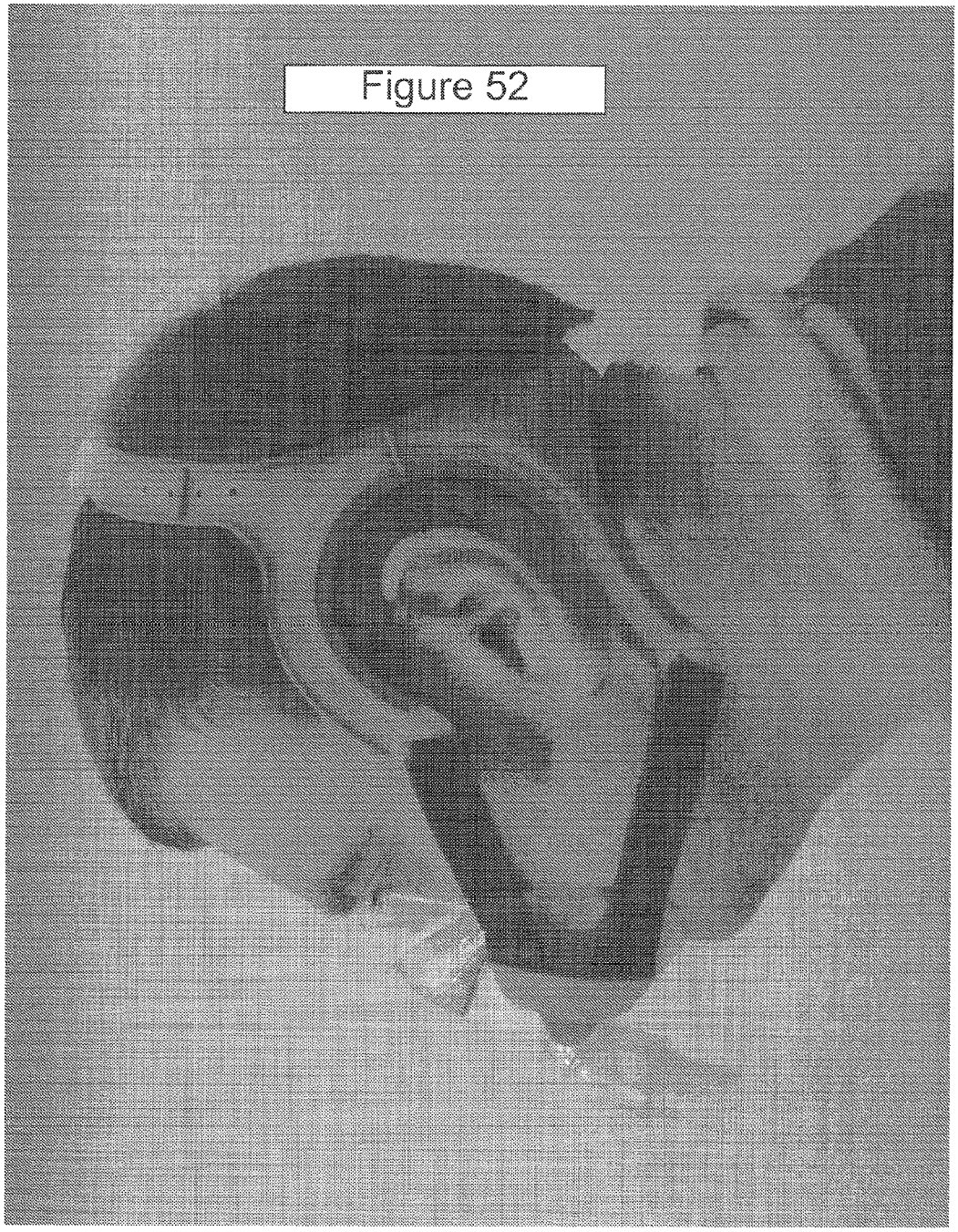
FIG. 52 is a side view of the backbone of FIG. 29 attached to a user's head.
Figure 53:
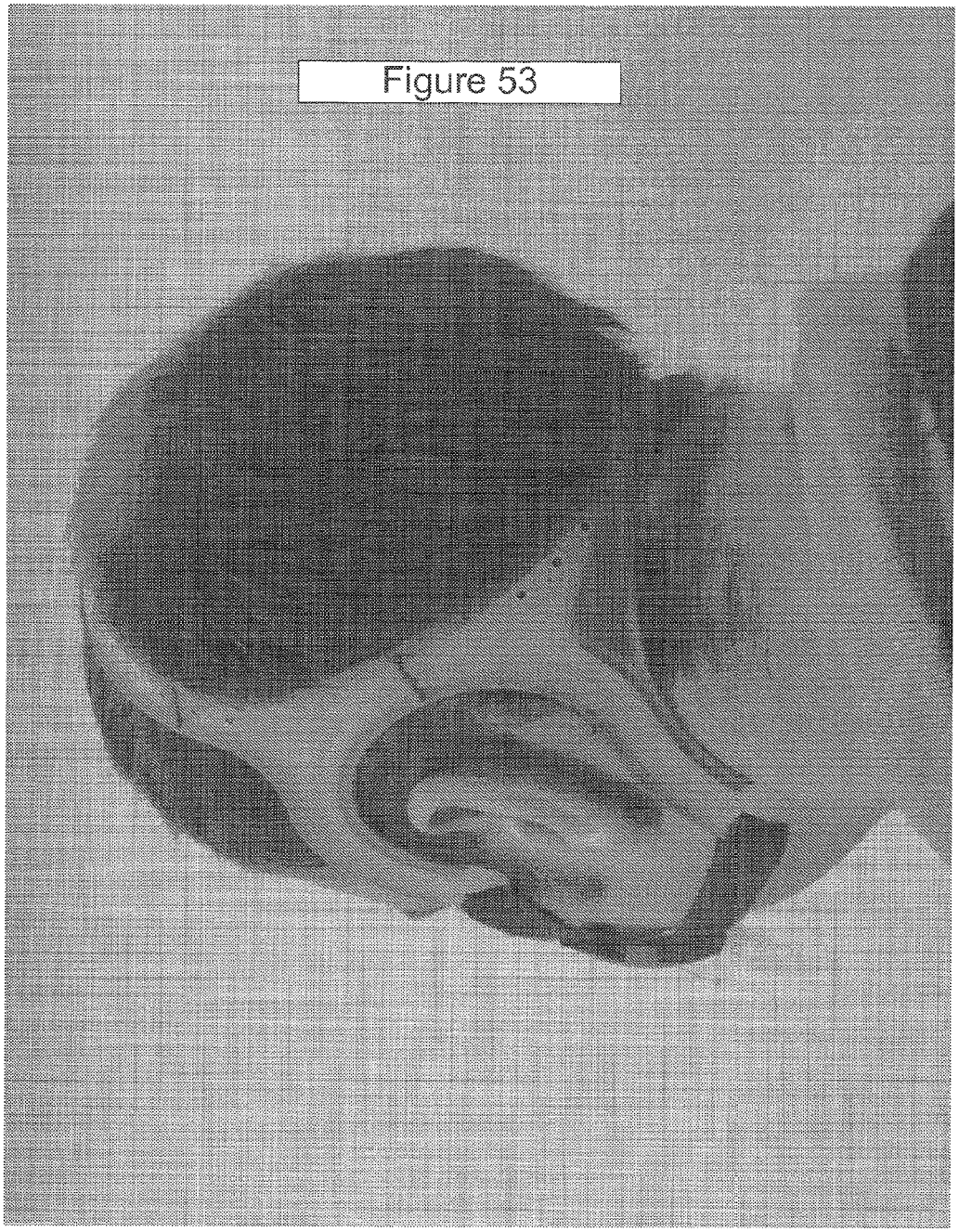
FIG. 53 is a rear perspective view of the backbone of FIG. 29 attached to a user's head.

In addition, the upper arms 284 are configured to extend downward from a location above the user's ear such that the adjustable top straps 260 extend no closer than about 10 mm to the user's eye when worn. The lower arm 286 is configured to be located off of the user's neck when the head is tilted up and down, and the termination point of the lower arm 286 is located generally below the user's ears so that the lower strap as attached to the lower arm 286 angles upwards from the termination point 290 to the mask assembly 120. In such a configuration, as illustrated in FIGS. 52 and 53, the lower straps and the upper straps form a triangle, and the space between the lower straps and the upper straps on the mask is smaller than the space between the lower straps and the upper straps on the headgear, thereby stabilizing the mask assembly 120 against upward and downward movements.

With reference again to FIG. 17, the elbow 222 connects to a conduit 300 through a disconnectable swivel assembly 302. As shown in the section view of FIG. 20, the elbow 222 comprises a stem 304 that comprises an inner wall 306 at the base. The inner wall 306 comprises a recess 308.

Figure 21:
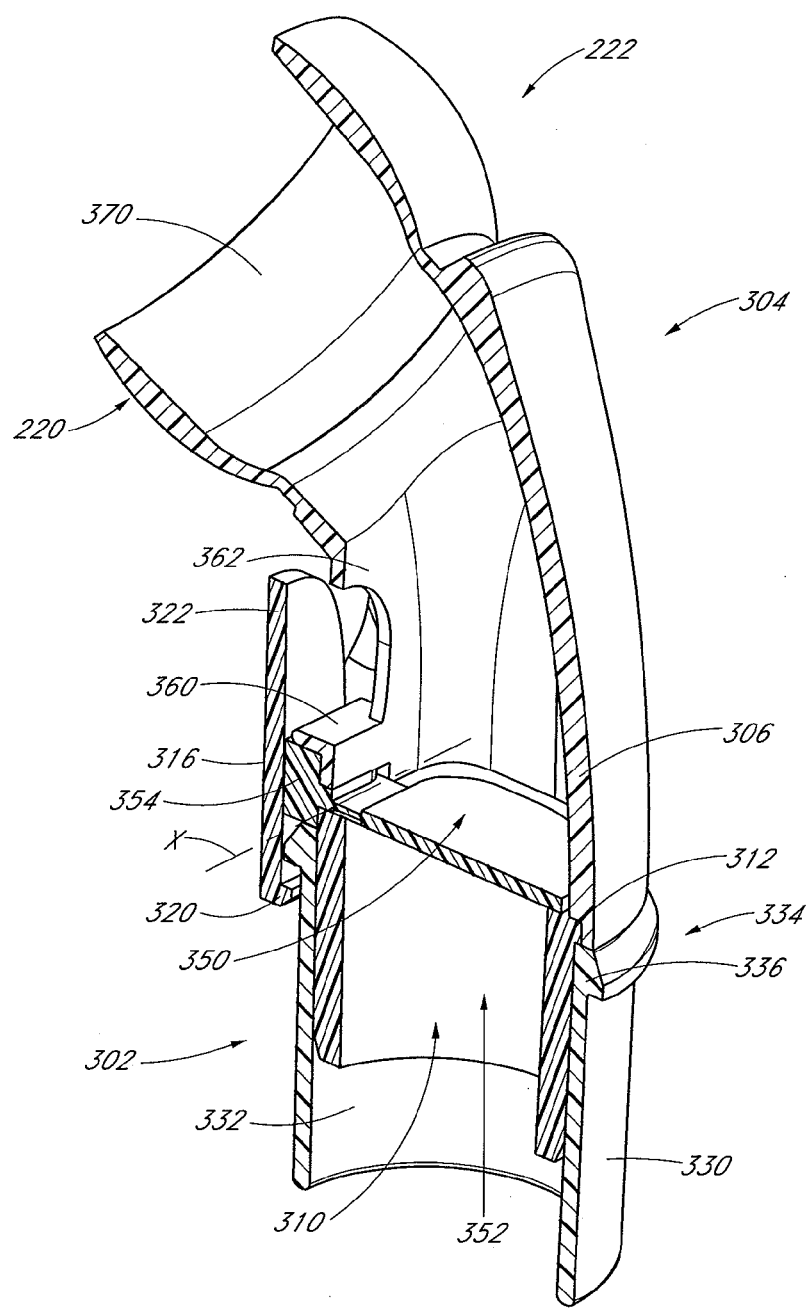
FIG. 21 is a sectioned perspective view of the connection port assembly of FIG. 17.

A sleeve 310 comprises a flange 312 that is received within the recess 308. The sleeve 310 can be secured into position within the elbow 222 using any suitable technique. The sleeve 310 comprises a generally cylindrical outer wall 314. The flange 312 comprises a section that extends outward to connect to a lever 316. Preferably, the flange 312 and the lever 316 are integrally formed. With reference to FIG. 21, the lever 316 includes a lower inwardly extending catch 320 and is capable of pivoting about the section that connects the lever 316 to the flange 312. Thus, pressing inward on an upper portion 322 of the lever 316 results in the catch 320 moving away from the generally cylindrical outer wall 314 of the sleeve 310.

A swivel 330 comprises a generally cylindrical inner wall 332. The inner wall 332 slides over the outer wall 314 of the sleeve 310 such that a sliding fit results between the swivel 330 and the sleeve 310. An upper portion 334 comprises a shoulder 336. The catch 320 of the lever 316 can secure the swivel 330 in axial position on the sleeve 310 by engaging with the shoulder 336. When the upper portion 322 of the lever 316 is depressed, the catch 320 moves away from the shoulder 336, which allows the swivel 330 to be removed from the sleeve 310.

Figure 20:
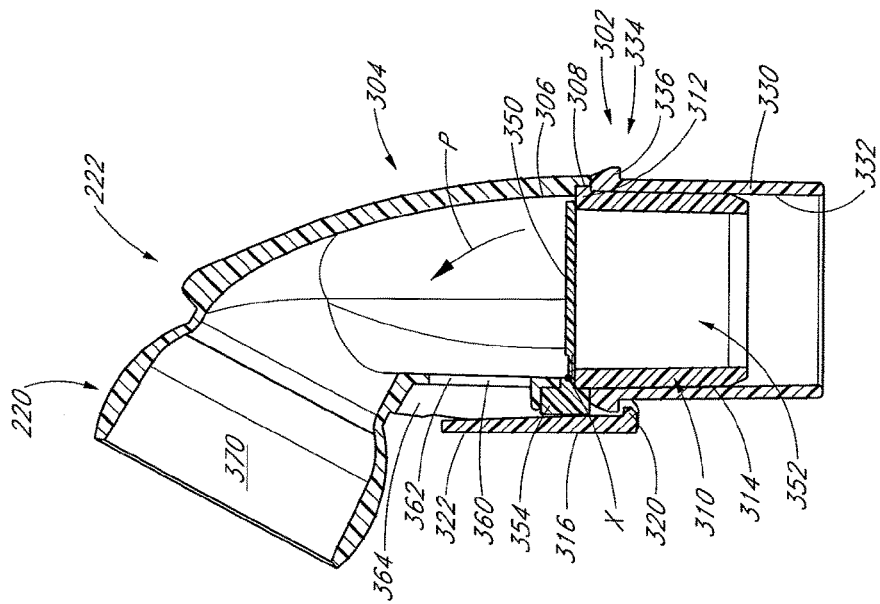
FIG. 20 is a sectioned side elevation view of the connection port assembly of FIG. 17.
Figure 19:
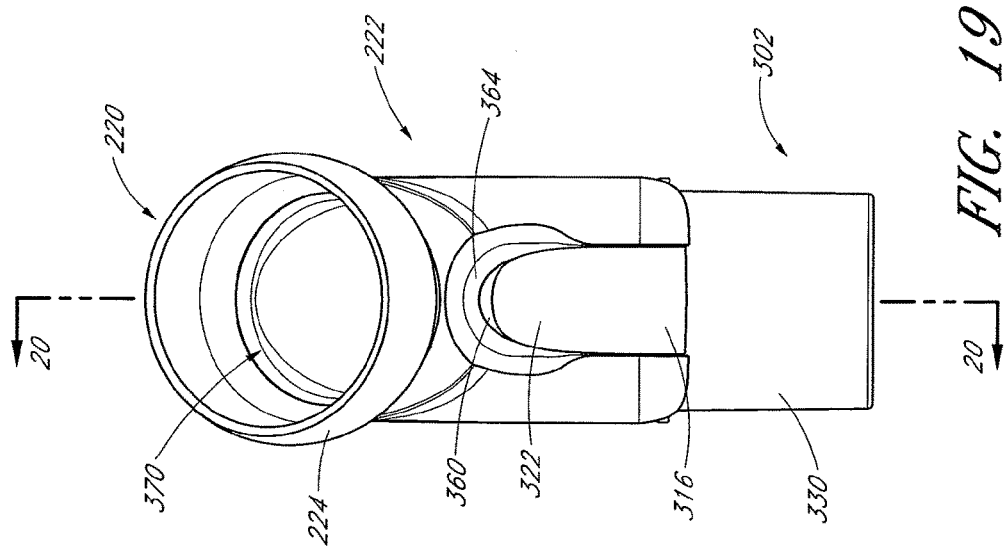
FIG. 19 is a rear elevation view of the connection port assembly of FIG. 17.

A flap 350 can be mounted between the stem 304 and the sleeve 310. In the illustrated configuration, the flap 350 extends into a flow channel 352 from a base 354 that is sandwiched between the stem 304 and the sleeve 310. The flap 350 can pivot upward (as shown in FIG. 20, see arrow P) about an axis X (see FIG. 21) away from the sleeve 310 such that flow from a positive pressure generator can continue generally unobstructed to the user through the interface 100. The flap 350 pivots downward into contact with the sleeve 310 to seal the flow channel 352 in the event that the positive pressure source stops providing a pressurized flow of air. In some configurations, the flap 350 will not fully contact the sleeve 310. In some configurations, the flap 350 will not seal the channel 352 when in the down position.

With reference to FIG. 21, a port 360 is defined through the elbow 222 at a location above the flap 350. The port 360 preferably is positioned along a portion of the elbow 222 that is in the vicinity of the axis X. In some configurations, the port 360 is positioned to be substantially shielded by the flap 350 from an inspiratory flow of air. In other words, as the air pivots the flap 350 away from the sleeve 310, the flap 350 is moved into a position that at least partially or completely covers the port 360.

In some configurations, the port 360 extends through a wall of the elbow 222 that comprises a generally planar inner wall 362. The generally planar inner wall 362 helps the flap 350 to generally seal the port 360 when the flap is moved upward away from the flange 312 of the sleeve 310.

In some configurations, the lever 316 overlies a majority of the port 360 such that the port 360 is generally obscured from view. As shown in FIG. 20, however, a gap 364 preferably surrounds at least a portion of the lever 316 such that a relatively free flow of air can pass through the port 360 when the flap 350 does not overly the port 360. In addition, in some configurations, the port 360 and the lever 316 are positioned on a same side of the elbow 222 as an opening 370 defined within the ball end 220, which opening is positioned within the mask assembly 102 when the connection port assembly 104 is assembled to the mask assembly 102. Advantageously, such a positioning places the port 360 in a position on the elbow 222 that faces the user. Such a location further obscures the port 360 from view during use, which results in a more aesthetically pleasing configuration. Moreover, because flow through the port 360 will be very infrequent, having the port 360 disposed toward the user will not cause any significant discomfort for the user.

While not shown, the elbow 222 also can comprise one or more bias flow vent holes. The bias flow vent holes preferably are positioned in a forwardly directed orientation such that any bias flow does not directly impinge upon the user.

Figure 49:
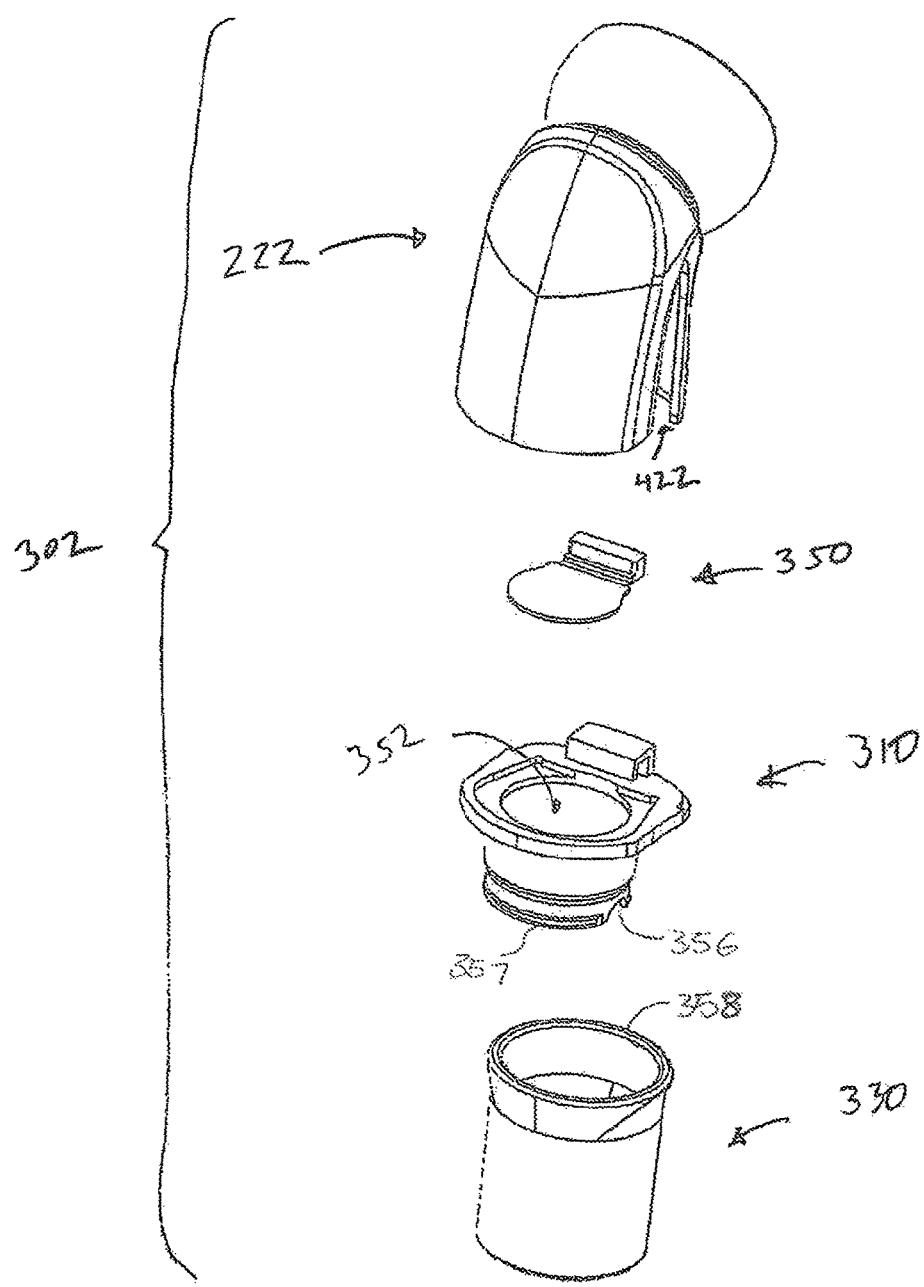
FIG. 49 is an exploded view of the swivel assembly of FIG. 48.
Figure 50:
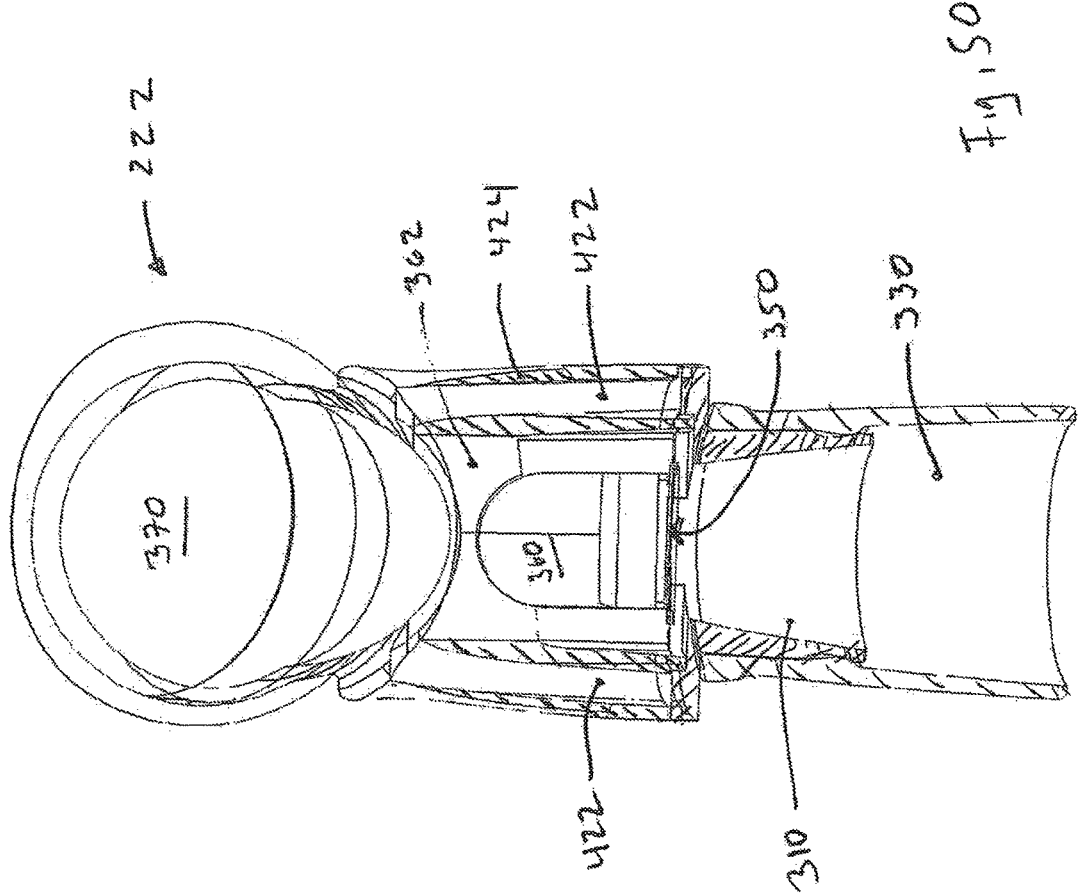
FIG. 50 is a cross-sectional view taken along line 50-50 of FIG. 48.
Figure 51:
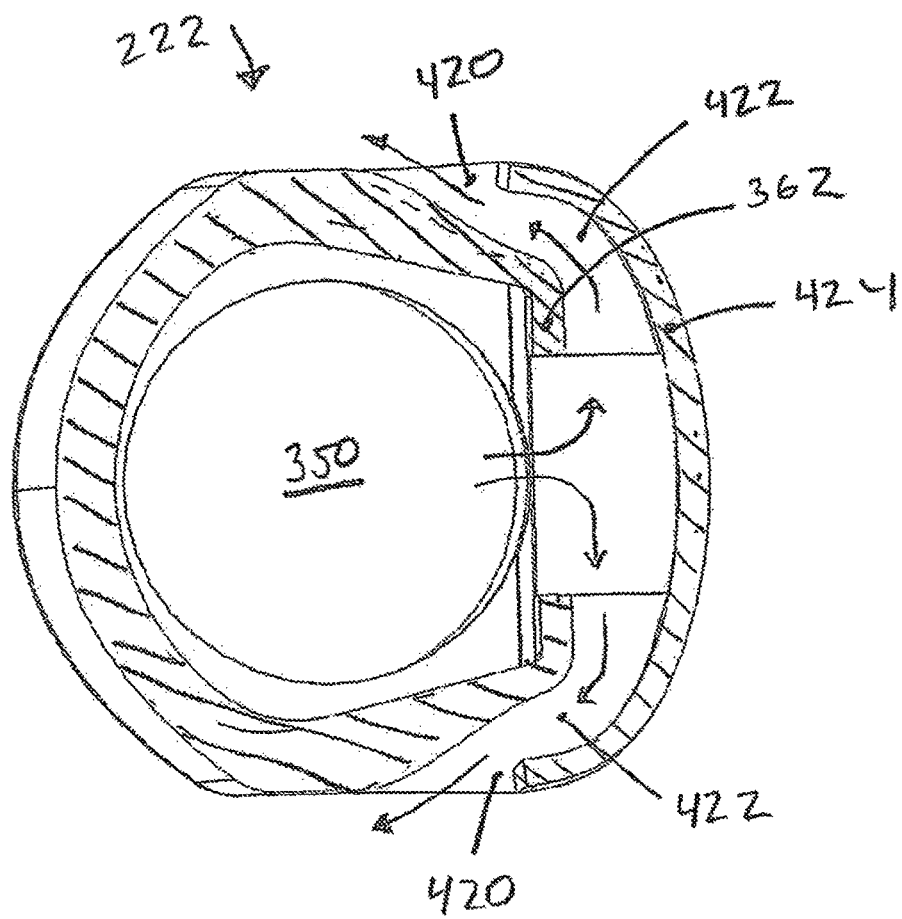
FIG. 51 is a cross-sectional view taken along line 51-51 of FIG. 48.

Another configuration of an elbow assembly 302 is illustrated in FIGS. 48-51. The elbow assembly 302 comprises an elbow 222, a sleeve, 310, and/or a swivel 330, as shown in FIG. 49. In some configurations, the elbow assembly 302 only includes the elbow 222 and sleeve and omits the swivel 330. The swivel may be permanently or removably attached to the sleeve 310 and elbow 222; in some configuration, the swivel 330 is integrally formed with the end of the delivery conduit. A flap 350 is positioned over the sleeve 310 such that it at least partially obstructs the sleeve's flow channel 352. The elbow assembly 302 functions similarly to the elbow assembly 302 of FIGS. 17-21; however, the elbow assembly 302 of FIGS. 48-51 provides the additional benefit of directing gases away from the patient when the flap 350 drops to its closed position (as shown in FIGS. 50 and 51).

With reference to FIG. 49, the sleeve 310 preferably comprises two or more cut out regions or recesses 356. The recesses 356 can have any suitable shape and, in the illustrated configuration, the recesses 356 comprise a semicircular configuration that extends upward into the sleeve 310. The sleeve 310 also comprises at least one bump 357, and preferably two or more bumps 357. Preferably, each of the bumps 357 extends around an arc of about 70 degrees. More preferably, each of the bumps 357 is generally centered between two recesses 356 and each of the bumps 357 extends about 70 degrees around an outer surface of the sleeve 310.

The swivel 330 preferably is generally cylindrical in configuration. As shown in FIG. 49, the swivel 330 has an inwardly extending ridge 358. The ridge 358 preferably encircles the entire inner surface. In some configurations, the ridge 358 can be interrupted. Preferably, however, the ridge 358 does not have any interruptions large enough to accommodate the entire bump 357 such that the ridge 358 and the bump 357 can cooperate to keep the swivel 330 mounted over the sleeve 310. When assembling the swivel 330 to the sleeve 310, the recesses 216 allow the bumps 220 to deflect inward such that the bumps 357 can slide over the ridge 358 and then snap back outward to secure the bumps 357 under the ridge 358.

The elbow 222 comprises openings 420 at its sides that are in fluid communication with an air venting channel 422. The air venting channel 422 is formed by the spacing between the elbow's inner and outer walls 362, 424, as shown in FIGS. 50 and 51.

When the flap 350 drops to its closed position, as shown in FIGS. 50 and 51, air exhaled from the user enters opening 370 of the elbow 222. The exhalation flows through the port 360 in the elbow's inner wall 362, and through the venting channel 422 until it exits the elbow 222 via the opening 420.

The configuration of FIGS. 48-51 provides a reduced overall length and improves product aesthetic by eliminating an unsightly hole positioned at the front of the elbow 222. In addition, the configuration of FIGS. 48-51 and improves patient comfort by preventing air from being directed towards the user. Instead, openings 420 direct air flow out of the sides of the elbow 222 and away from the patient.

Figure 54:
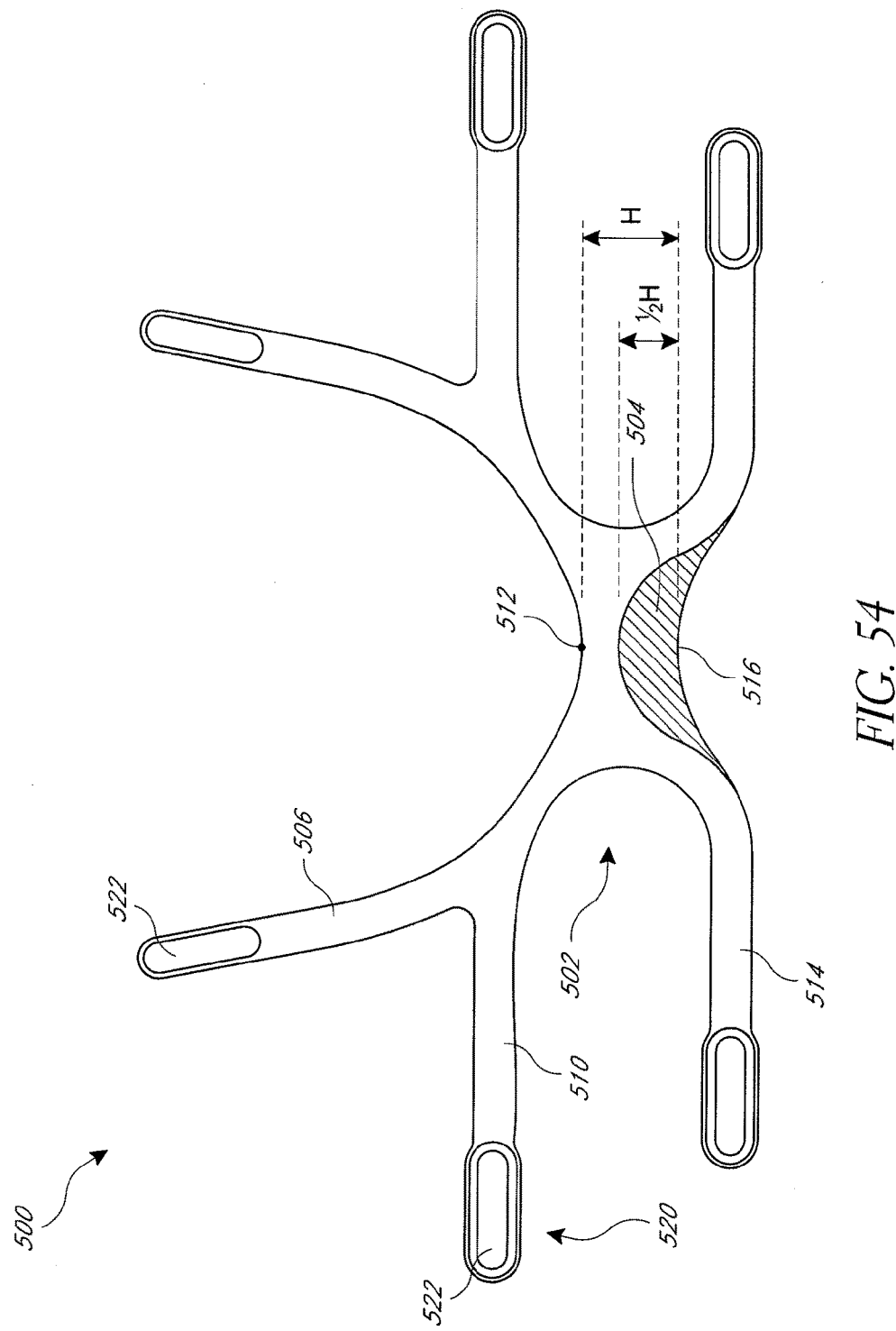
FIG. 54 is a perspective view of a flexible headgear with a panel for use with a mask assembly in the field of respiratory therapy.

With reference to FIG. 54, a flexible headgear assembly 500 can be used to secure a mask assembly to a user's head for respiratory therapy, for example but without limitation. The illustrated flexible headgear assembly 500 can be used with any suitable mask assembly, including but not limited to any of the mask configurations disclosed herein.

The illustrated flexible headgear assembly 500 comprises a back strap portion 502. At least a portion of the back strap portion 502 is joined with a panel 504. In the illustrated configuration, the back strap portion 502 is configured to span a distance around the back of the user's head and is configured to extend toward each lateral side of the user's head.

With continued reference to FIG. 54, a pair of upper arms 506 and a pair of middle arms 510 can extend generally transversely from a top edge 512 of the back strap portion 502. A pair of lower arms 514 can extend generally transversely from a lower edge 516 of the back strap portion 502. In some configurations, the pair of lower arms 514 extend down and away from the back strap portion 502 such that a lower edge of the lower arms 514 will be positioned lower than the bottom edge of the back strap portion 502. In some configurations, the pair of middle arms extend upward and away from the back strap portion 502 such that the middle arms 510 have an upper edge that is positioned higher than the upper edge of the back strap portion.

The lower arms 514 and the middle arms 510 terminate with ends 520 in the illustrated configuration. The ends 520 can comprise securing portions 522, which can be formed of hook or loop components for a hook-and-loop style fastening arrangement. Preferably, and as will be described in more detail below, the securing portions 522 comprise at least hook portions that can engage with the material of another portion of the headgear assembly 500. Each of the upper arms 506 also can terminate with regions comprising a securing portion 524.

When positioned on the head of a user, the back strap portion 502 is located on or below the external occipital protuberance and above the nape of the neck of the user. The upper straps 506 can be connected together in any suitable manner. In some configurations, a clip secures the upper straps 506 together with the securing portion 524 doubled back and secured to another portion of the upper straps 506. Thus, the upper straps 506 can extend generally over a top of the head of the user to limit downward movement of the balance of the headgear assembly 500.

Figure 40:
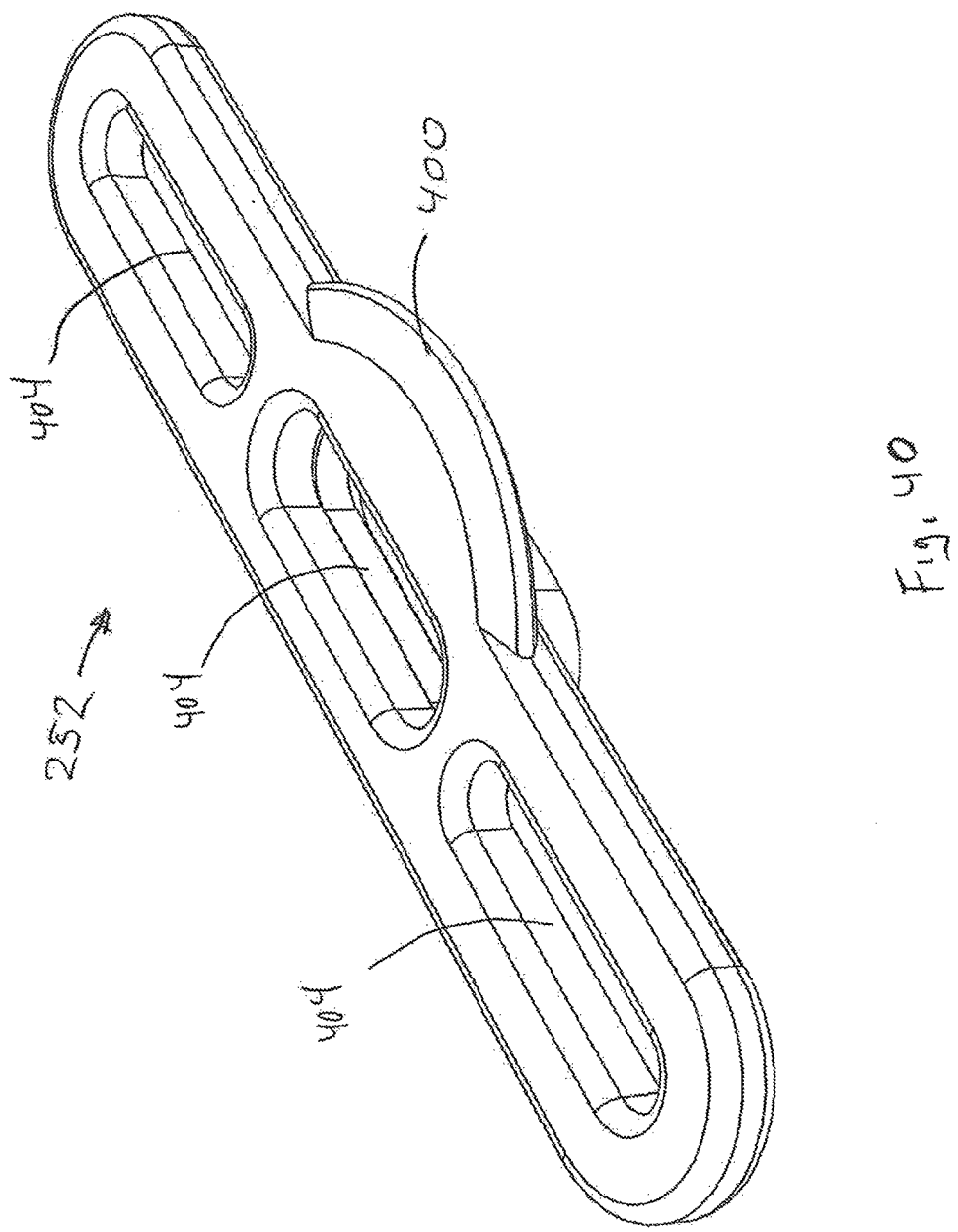
Figure 41:
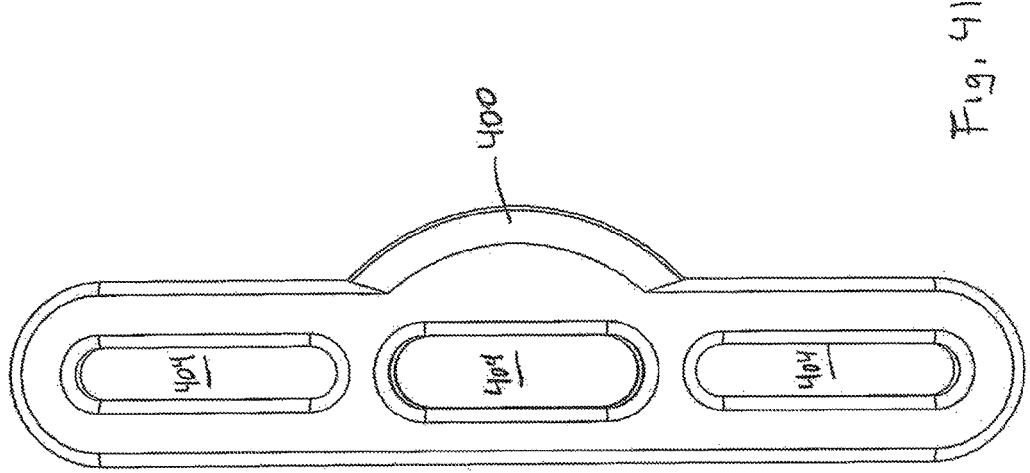
Figure 42:
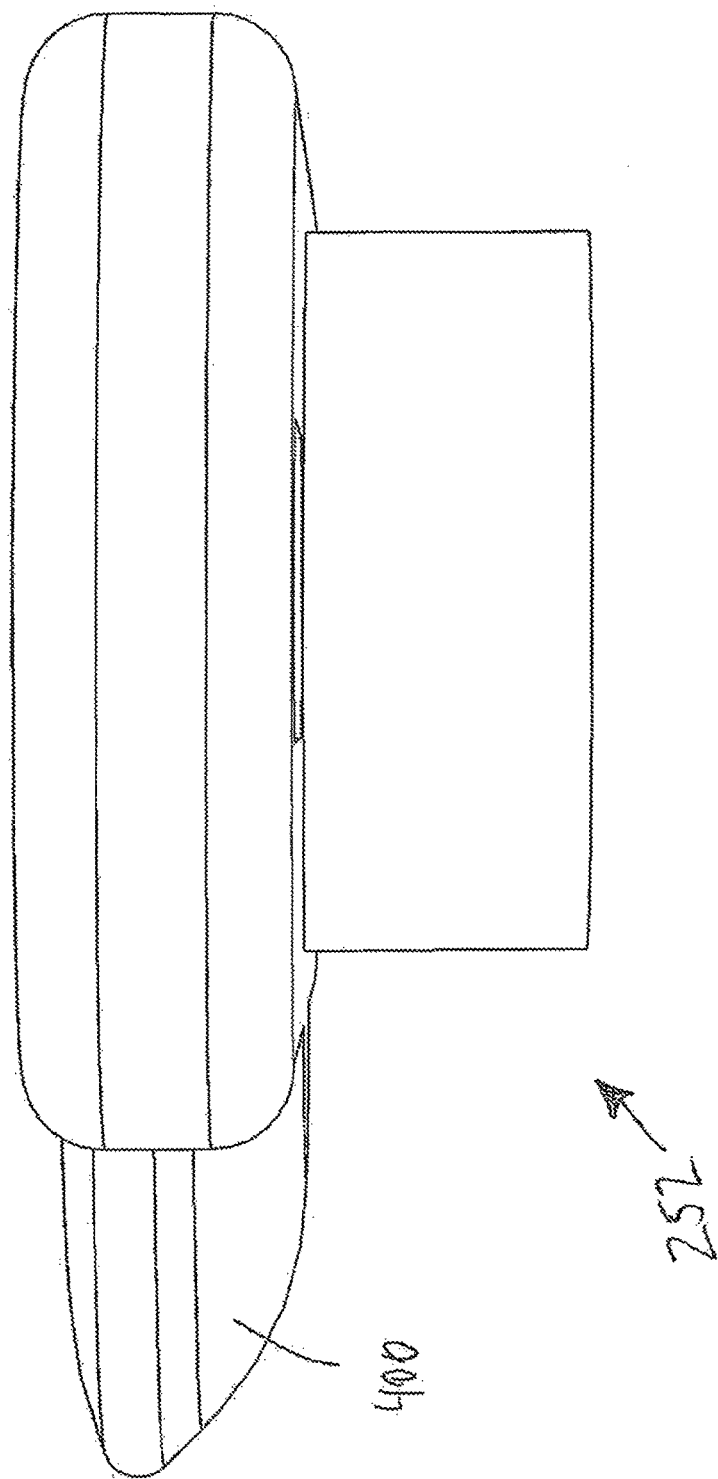

The middle arms 510 and the lower arms 514 can be connected to a clip (not shown) or another portion of the mask assembly such that the middle arms 510 and the lower arms 514 secure the headgear assembly 500 to the mask either directly or indirectly (e.g., with a clip, such as that shown in FIG. 40, for example but without limitation). The ends 520 of the middle arms 510 and the lower arms 514 can be passed through loops or other structures on the mask assembly and doubled back with a fold. The overlapping portions can be secured in any suitable manner. For example but without limitation, the overlapping portions can be secured with a hook-and-loop fastening arrangement (e.g., Velcro® fasteners).

Figures 55, 56:
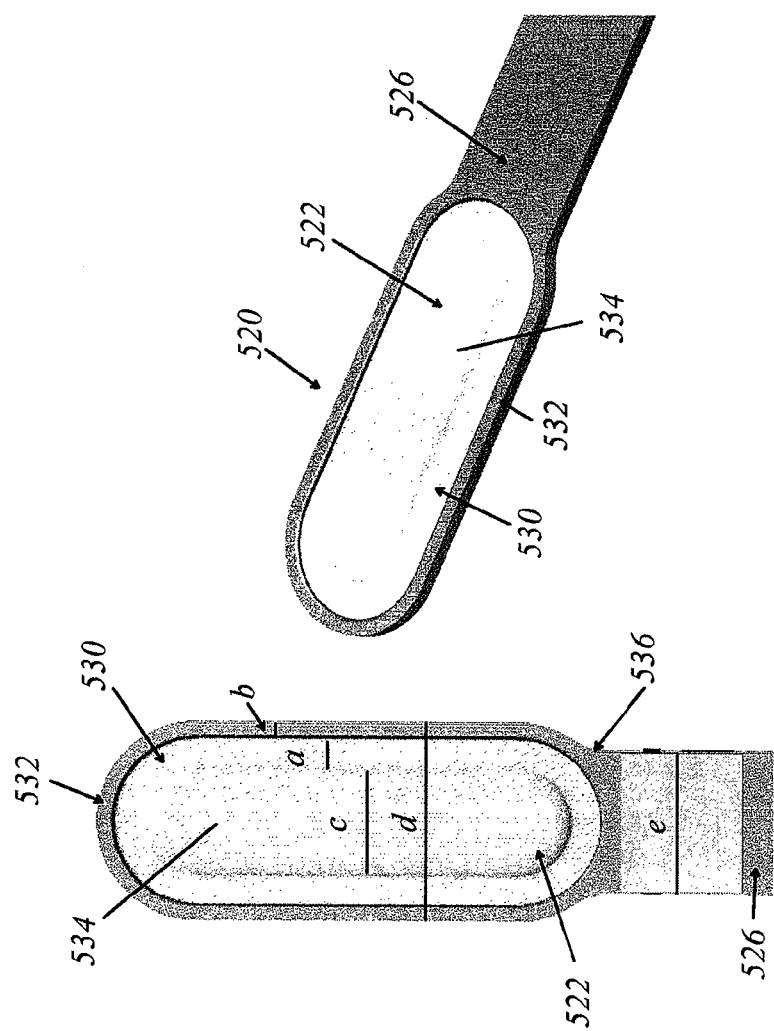
FIG. 55 is a view of an enlarged end enlarged region of arms of FIG. 54 with an embedded hook-fabric tab attached thereto.
FIG. 56 is a perspective view of the end region of FIG. 55.

With reference now to FIG. 55, at least one of the end portions of the upper arms 506, the middle arms 510 and the lower arms 514 can comprise enlarged ends 520. Preferably, the enlarged ends 520 are formed on at least the middle arms 510 and the lower arms 514 of the flexible headgear 500. In some configurations, the enlarged ends 520 can be found on one or more arm that connects to the mask assembly. The enlarged ends 520 can be integrally formed with the main portion of the arms 510, 514.

As described above, the arm 526 can be formed integrally with the enlarged end 520. The illustrated enlarged end 520 has a width d while the arm 526 has a width e. The width e of the arm 526 can be between about 12 mm and about 20 mm, between about 14 mm and about 18 mm, or preferably about 16 mm. The width d of the enlarged end 520 can be between about 18 mm and about 26 mm, between about 20 mm and about 24 mm, or preferably about 22 mm. In some embodiments, the difference between the largest width d of the enlarged end 520 and the arm width e is between about 3 mm and about 10 mm, or between about 5 mm and about 8 mm. In some configurations, the difference between the largest width d of the enlarged end 520 and the arm width e is about 6 mm. Because the width d of the enlarged end 520 is greater than the width e of the arm 526, an edge of the enlarged end 520 can more easily be located such that the portion used to secure the end 520 to the arm can be more easily located in order to refit the arm 526 (e.g., in order to tighten, loosen, remove, or otherwise reposition the flexible headgear 500).

Moreover, when the width d of the enlarged end 520 is greater than the width e of the arm 526, a neck portion 536 can be formed at a location between the enlarged end 520 and the arm 526. The neck portion 536 can provide reduce the likelihood of the enlarged end 520 sliding out of the attachment portion on the mask assembly when secured to the user's head. For example, an opening in the attachment portion on the mask assembly may be about 16 mm to about 18 mm wide while the enlarged end 520 may be about 22 mm and the arm 526 may be about 16 mm. Accordingly, the likelihood of the enlarged end 520 inadvertently pulling through the opening is greatly reduced.

The geometry of the neck portion 536 can further reduce the likelihood of the enlarged end 520 inadvertently pulling through the opening. Any suitable transition can be used. As illustrated in FIG. 56, the neck portion 536 can be curved to facilitate removal of the arm from the mask assembly, when desired. The neck portion can extend at an angle between about 0 degrees and about 90 degrees relative to the arm. Preferably, the neck portion 536 extends at an angle of between about 20 degrees and about 60 degrees. In some configurations, the neck portion 536 can be a more abrupt transition or a less abrupt transition. The more abrupt the transition, the less likely the arm will inadvertently separate from the mask assembly.

The neck portion 536 forms a portion of the geometry of the enlarged end 520. In some configurations, the enlarged end 520 can be substantially oval-shaped. In some configurations, the enlarged end 520 can be configured to resemble various shapes, including, for example, a parallelogram, an ellipse, a circle, a triangle, or any other suitable shape.

With continued reference to FIG. 55, each of the enlarged ends 520 can comprise an embedded panel 522 having hook fasteners or the like. The panels 522 can be located on the enlarged ends 520 such that the enlarged ends 520 can be secured to another portion of the corresponding arm when the arm has been folded back over itself. The embedded panels 522 can be comprised of a hook-fabric (e.g., Velcro®). Thus, the enlarged ends 520, and the hook materials of the panels 522 in particular, can be fastened onto another portion of the corresponding arm to secure the headgear assembly 500 to the mask assembly.

The panels 522 can be attached to the ends of the arms in any suitable manner. In some configurations, the panel 522 is attached to the enlarged end 520 by ultrasonic welding. For example, the panel 522 can be located in a desired location along the arm and then the ultrasonic welding process can effectively melt the two materials together. With reference to FIG. 56, when ultrasonic welding is used to attach the enlarged hook-fabric panel 522 to the enlarged end 520, a weld edge 530 having width a is formed around a perimeter of the enlarged hook-fabric panel 522. As a result of the ultrasonic welding procedures in the illustrated configuration, a width a of the weld edge 530 is approximately 3 mm. An area of the hook-fabric panel 522 that comprises the weld edge 530 generally is not functional to engage hook-receptive materials as a result of the ultrasonic welding procedure melting or otherwise deforming the hooks of the hook-fabric. Thus, a functional surface area of the hook-fabric panel 522 is decreased by a surface area equal to that of the weld edge.

The weld edge 530 can be bound by a soft edge 532 having width b comprised of the hook-receptive breathable composite materials of the enlarged end 520. Preferably, the weld edge 530 is recessed below the surface of the soft edge 532. A projection of the width e of the arm 526 can extend through the weld edge 530 such that the soft edge 532 would be positioned slightly outward of the projection of the width e of the arm 526.

The width b of the soft edge can be from about 0.5 mm to about 4 mm, from about 1 mm to about 3 mm, or preferably about 2 mm. An active hook portion 534 can adjoin the weld edge 530 and have a width c. The width c of the active hook portion can be slightly narrower than the width e of the arm 526. By increasing the width c, the functional surface area of hook-fabric material can be increased, thus improving a sheer force resistance and durability. By having the width c smaller than the width e of the arm 526, the arm 526 reduces the likelihood of the active hook portion 534 contacting the skin of the user. The width c of the active hook-fabric portion 534 can be from about 8 mm to 16 mm, from about 10 mm to about 14 mm, or preferably about 12 mm. The enlarged end width e enables the width c of the functional surface area to be increased. In other words, the end of the arm has been enlarged such that the width of the active hook portion 534 can be increased, which can provide a more secure attachment of the enlarged end to the surface of the arm.

The flexible headgear assembly 500 can be formed of any suitable material. In some configurations, the flexible headgear assembly 500 can be covered with or have at least some portion formed of a hook-fastener receptive breathable composite material. In some configurations, the flexible headgear assembly 500 can be at least partially formed of Nylon/Lycra Breath-O-Prene® material. In some embodiments, when a 150 mm long by 20 mm wide sample of the material is subjected to a 10 N axial load, the sample elongates to about 207 mm, which is an elongation of about 38% caused by the 10 N axial load. Thus, the material preferably is fairly elastic. In some embodiments, the headgear assembly 500 can comprise one or more rounded edges. The rounded edges can be formed in any suitable manner. In some configurations, the rounded edges are formed by applying heat and pressure to the edges of the headgear assembly 500. In some configurations, the rounded edges are formed in a manner similar to the techniques described in U.S. Pat. No. 3,295,529, which is hereby incorporated by reference in its entirety.

As introduced above, the back strap portion 502 of the illustrated flexible headgear assembly 500 preferably comprises at least one relatively inelastic panel 504. The panel can be formed of a relatively low-stretch material, such as a polyester Breath-O-Prene® material, for example but without limitation. In some embodiments, when a 150 mm long by 20 mm wide sample of the material is subjected to a 10 N axial load, the sample elongates to about 160 mm, which is an elongation of about 7% caused by the 10 N axial load. Thus, the material preferably is fairly inelastic or non-stretch when compared to the more elastic material of the flexible portion.

Because the panel 504 is formed of a less elastic material than the surrounding portions of the headgear assembly 500, the panel 504 resists stretching in at least a portion of the headgear assembly 500. By resisting elongation of at least a portion of the otherwise elastic headgear assembly, the panel helps maintain the headgear 500 in a desired shape and helps maintain the headgear 500 at a desired location relative to a back of the user's head.

Figure 57A:
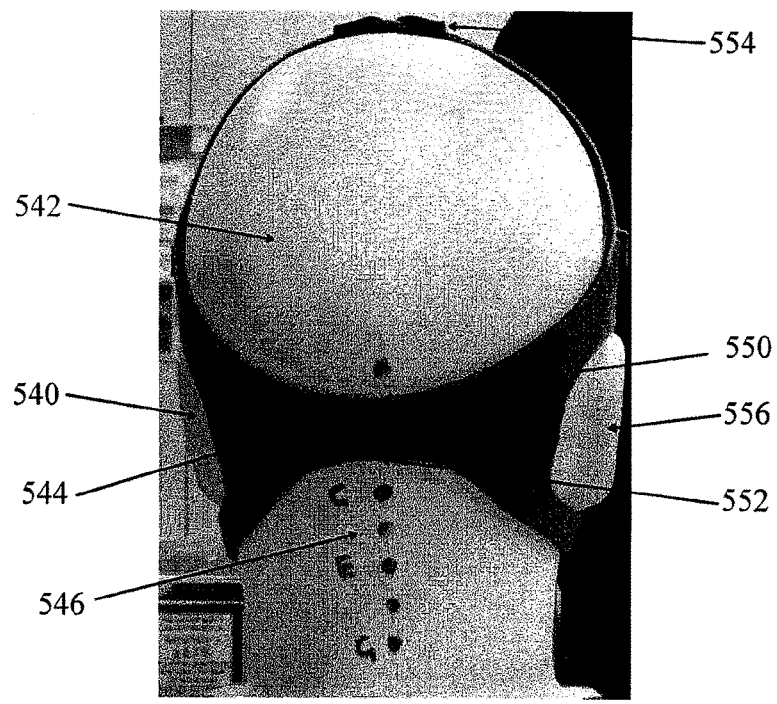
FIG. 57A is a rear view of a headgear without a panel attached to a testing model before a force is applied to lower arms of the headgear.
Figure 57B:
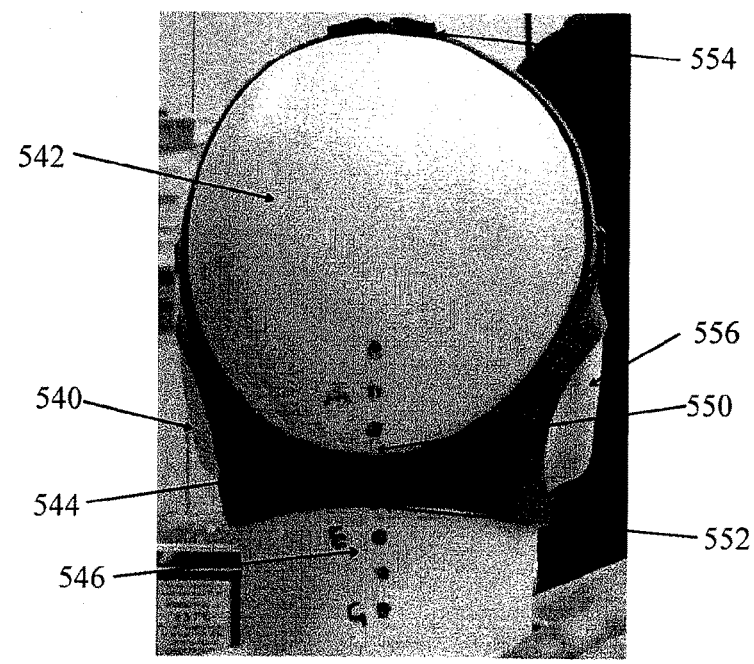
FIG. 57B is a rear view of the headgear of FIG. 57A illustrating the displacement of a back strap portion of the headgear when a force is applied to the lower arms of the headgear.
Figure 58A:
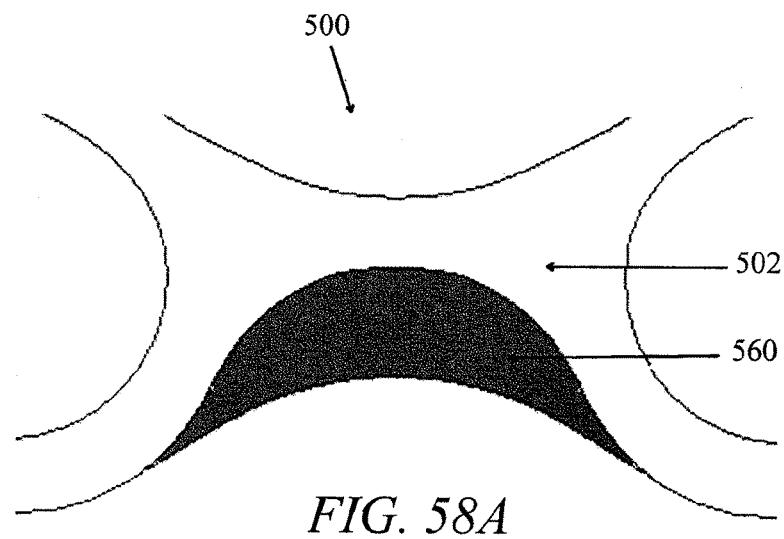
FIGS. 58A-58D are alternate configurations of panels compatible for use with the headgear of FIG. 54.
Figure 58B:
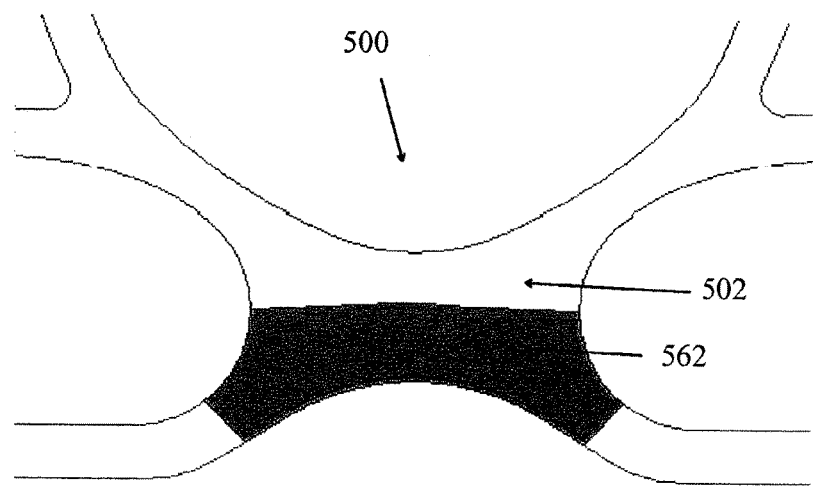
Figure 58C:
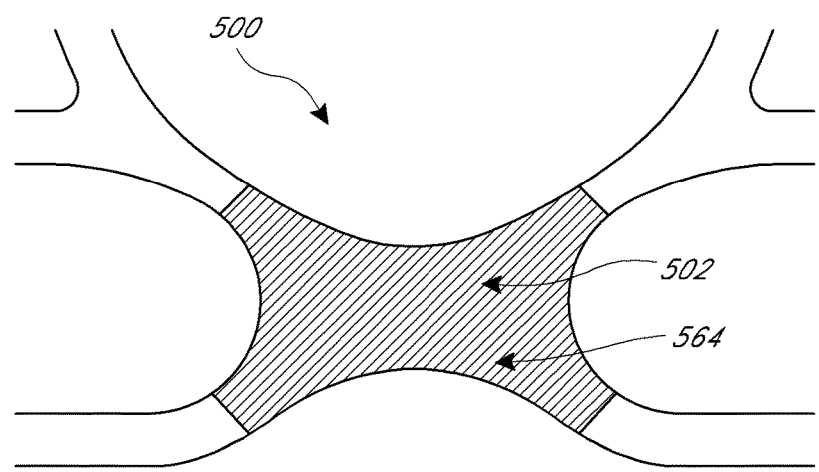
Figure 58D:
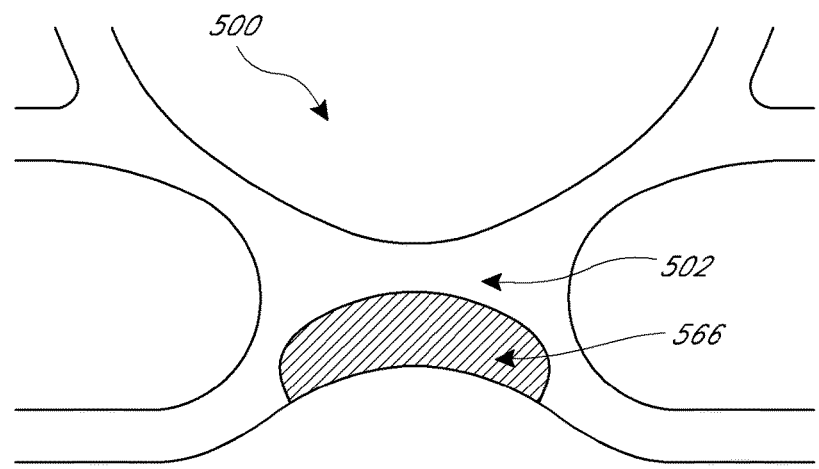

Testing has shown that, without the use of the panel 504, elongation in the back of headgear assembly 500 can cause the headgear assembly to elongate and move downward toward the user's neck when increasing loads are applied to the lower straps. FIGS. 57A and 57B illustrate the effect of applying increasing force to the lower arms 514 of the flexible headgear 540 with a back strap portion 544 completely comprised of an elastic material. The illustrated configuration in FIGS. 57A and 57B do not feature the panel 504.

As described above, the back strap portion 544 is positioned in a desired location when it is located on or below the external occipital protuberance and above the nape of the neck of the user. In FIG. 57A, the back strap portion 544 is shown in a more preferred position. To aid in visualizing movement, position markers 546 are shown on the testing model 542. When increasing loads are applied to the lower arms 514, as shown in FIG. 57B, the elastic nature of the back strap portion 544 allows it to elongate and deform, which allows the back strap portion 544 to move downward along the neck of the user. Reference to the position markers 524 illustrates the movement. With downward movement, more force from the back strap portion 544 is applied to the neck rather than the head, which is less desired. Because the flexible headgear 540 can be worn for a period of minutes to hours, or for a period of hours to days when used for respiratory therapy, the lowered positioning of the back strap portion 544 can create discomfort for the user.

In order to reduce the degree of elongation of the back strap portion 502 when increasing force is applied to the lower arms 514, the less-elastic panel 504 can be attached to the back strap portion 502. In some configurations, the panel 504 can comprise of a substantially non-stretch insert 560. The insert 560 can be attached to the back strap portion 502, for example, by over-lock stitching, by ultrasonic welding, by use of glue or other adhesives, or by any other method known to those of skill in the art. When the insert 560 is attached to the back strap portion 502, it can provide a greater tension resistance, which allows a greater force to be applied to the lower arms 514 when attaching and using the flexible headgear 500. Thus, the insert 560 can advantageously reduce deformation of the back strap portion 502 and aid in keeping it located in a desired position relative to the head and neck of the user.

As illustrated in FIGS. 58A-58D, the non-stretch insert 560, 562, 564, 566 can be configured in a variety of shapes, including but not limited to those shown in FIGS. 58A-58D. Preferably, the non-stretch insert 560, 562, 564, 566 adjoins or covers at least the backstrap portion 502. In some configurations, the non-stretch insert 562, 564 adjoins or covers at least a portion of the lower arms 514. In some configurations, the non-stretch insert 562, 564 adjoins or covers at least a portion of a junction between the lower arms 514 and the backstrap portion 502. In some configurations, the non-stretch insert 564 adjoins or covers at least a portion of the middle arms 510. In some configurations, the non-stretch insert 564 adjoins or covers at least a portion of a junction between the middle arms 510 and the backstrap portion 502. In some configurations, a height of the non-stretch insert 560 is at least about half of a height h of the back strap portion 502. In some configurations, the height of the non-stretch insert 560 is preferably more than about half of the height h of the back strap portion 502. By leaving a portion of the back strap portion 502 formed of the more elastic material, the back strap portion 502 is able to stretch and conform in a limited degree but more than would be possible with a back strap portion fully formed from a less elastic material.

The non-stretch insert 560 can be configured to have any suitable surface area. The non-stretch insert 560 can be configured to extend along varying lengths of the lower edge 516 of the back strap portion 502. In some configurations, the non-stretch insert 560 extends along more than half of the lower edge 516 of the back strap portion 502. Preferably, the non-stretch insert 560 extends along substantially all of the lower edge 516 of the back strop portion 502. Other configurations are possible.

Figure 59:
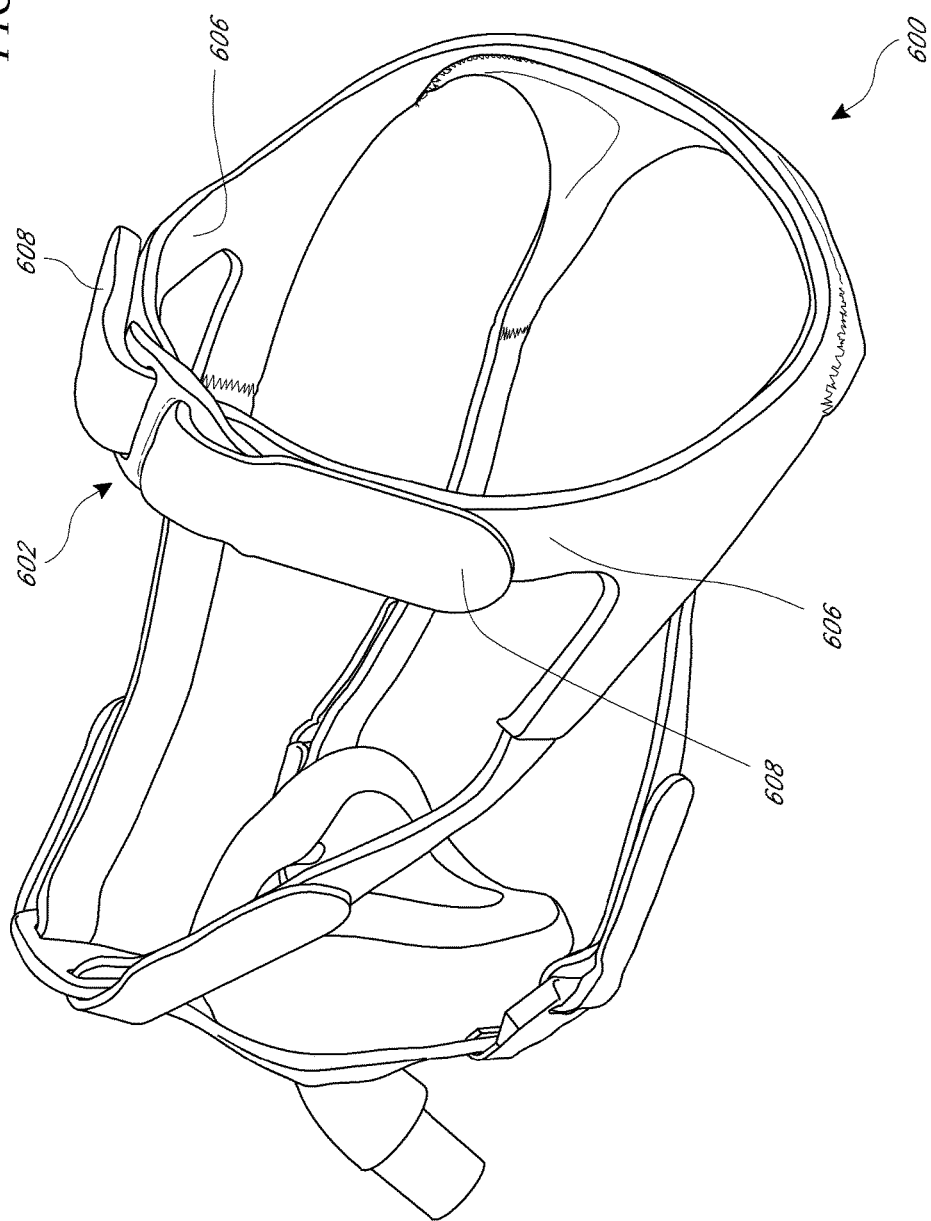
FIG. 59 is an assembly incorporating headgear with a winged buckle connection.

With reference now to FIG. 59, an assembly is illustrated comprising headgear 600 having two or more straps that can be connected with a winged buckle 602. As with the other headgear described herein, the headgear 600 can be used with any suitable mask assembly, including but not limited to any of the mask configurations disclosed herein. Moreover, the illustrated configuration comprises straps that are connected by a winged buckle 602 and such a configuration can be used with any of the headgear disclosed herein, for example but without limitation.

In the illustrated configuration of FIG. 59, the headgear assembly 600 comprises at least a pair of upper arms 606. Each of the upper arms 606 can terminate with ends 608. In some configurations, at least one of the pair of upper arms 606 comprises a securing portion, such as any of the securing portions described elsewhere. In the illustrated configuration, each of the upper arms 606 comprises a securing portion. Preferably, the securing portions are positioned at least partially on the ends 608. In some configurations, the securing portions can be formed of hook or loop components for a hook-and-loop style fastening arrangement. Preferably, the securing portions comprise at least hook portions that can engage with the material of another portion of the headgear assembly 600.

Figure 61:
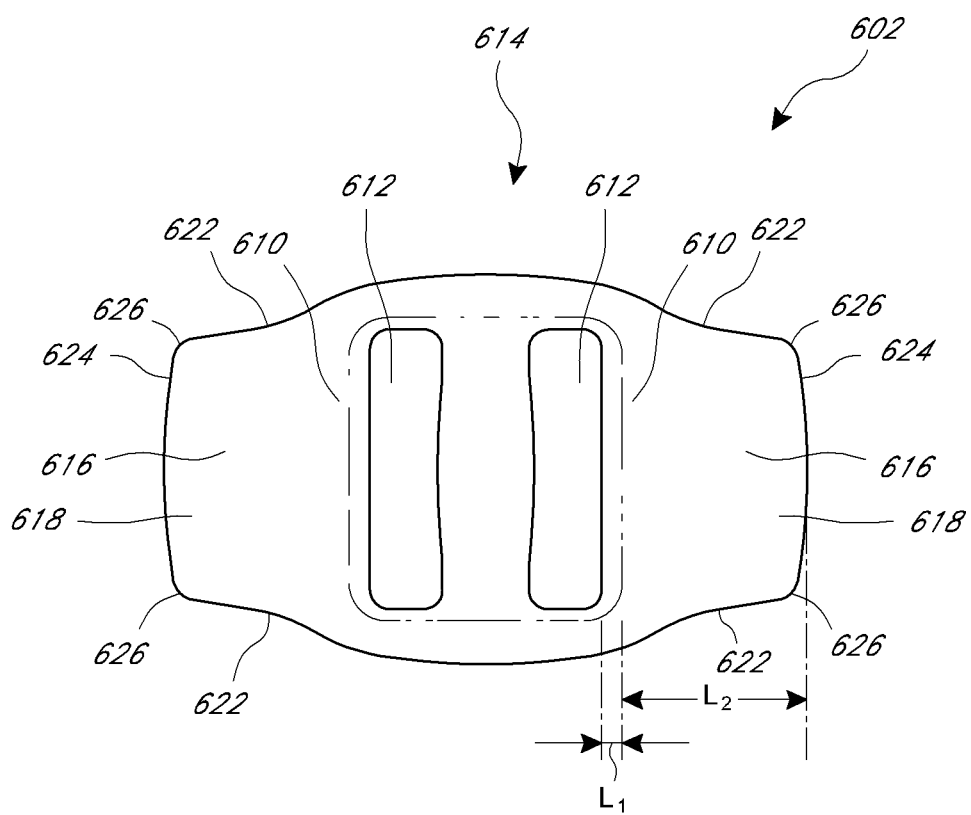
FIG. 61 is a top view of a winged buckle used in the winged buckle connection of FIG. 59.

With reference to FIG. 59, the upper arms 606 can be joined by the winged buckle 602, for example but without limitation. As illustrated in FIG. 61, the winged buckle 602 can comprise a body 610 that defines at least one slot 612, and preferably at least two slots 612. The at least one slot 612 accommodates the ends 608 of the straps 606 such that the ends 608 of the straps 606 can be passed through the at least one slot 612 and then folded over and secured in position with the securing portions as described above.

The body 610 of the illustrated buckle 602 comprises a tri-glide slide connector portion 614 and a pair of wings 616. Accordingly, the at least one slot 612 can be defined by the tri-glide slide connector portion 614. In some configurations, however, the at least one slot 612 can be formed by one or more of the following (including multiples of one or more of the following components): a loop, a square ring, a D-ring, an oval ring, a sliplock buckle, a ladder lock or the like.

The wings 616 advantageously provide support to the straps 606 such that, as shown in FIG. 59, the headgear assembly 600, including the straps 606 can substantially maintain a three dimensional shape. In some configurations, a buckle without wings will allow folding and flopping of the headgear assembly and more particularly the straps 606 about the buckle, which can cause the headgear assembly to not substantially maintain a three dimensional shape. Accordingly, the wings 616 have been found to enhance usability of the headgear assembly 600.

Figure 62:
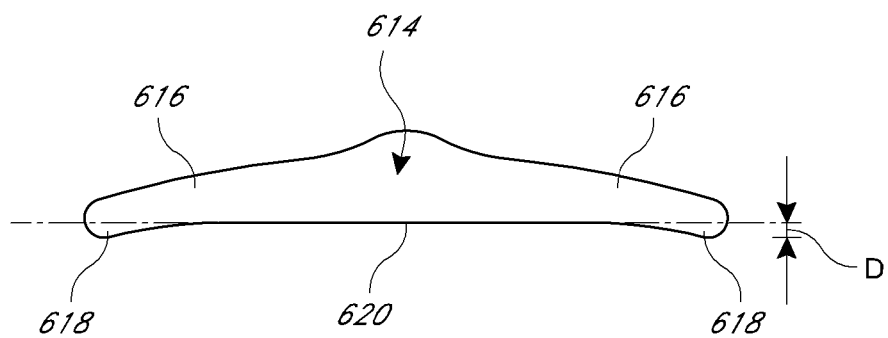
FIG. 62 is a side view of the winged buckle used in the winged buckle connection of FIG. 59.

With reference to FIG. 62, laterally outward extents 618 of the wings 616 extend downward beyond a lower surface 620 of the connector portion 614. By extending the lateral extents 618 below the lower surface 620, the buckle 602 can better conform to and/or follow a crown of a head of a user relative to a flat buckle. In some configurations, however, the laterally outward extents 618 may not extend downward below the lower surface 620 and/or the bottom of the buckle, including the wings, may be substantially flat or rounded.

The buckle 602 can be formed of any suitable material. In some configurations, the buckle 602 can comprise two or more different materials such that the connector portion 614 can be formed of a more rigid material while at least the wings 616 can be formed of a softer material. The softer wings 616 can improve comfort while the more rigid connector 614 enables the buckle 602 to carry the loads that are expected to be experienced in the headgear assembly 602.

In some configurations, the two or more different materials can be overmolded or comolded to form the buckle 602. In some configurations, the two or more different materials can be mechanically connected (e.g., snapfit, keyed or the like) or can be joined by cohering, adhering, or the like. In some configurations, at least the wings 616 can be formed of a thermoplastic elastomer or an impact-modified polyethylene, for example but without limitation. In some configurations, the connector portion 614 can be formed from a nylon or the like, for example but without limitation. In some configurations, the connector portion and the wings can be formed from materials having the same base material (e.g., materials that have suitable chemical relationships to allow joining of the materials).

With reference still to FIG. 62, the wings 616 preferably generally taper in thickness from the region proximate the connector portion 614 toward the lateral extents 616. While any suitable tapering profile can be used, the reduction in thickness facilitates flexure of the wings 616 to enable better conformity to the anatomy of the user. In other words, the reduced thickness of the wings 616 at locations laterally outward from the portion adjoining the connector portion

614 results in a weaker flexural strength, which helps conformity to the anatomy of the user.

Figure 60:
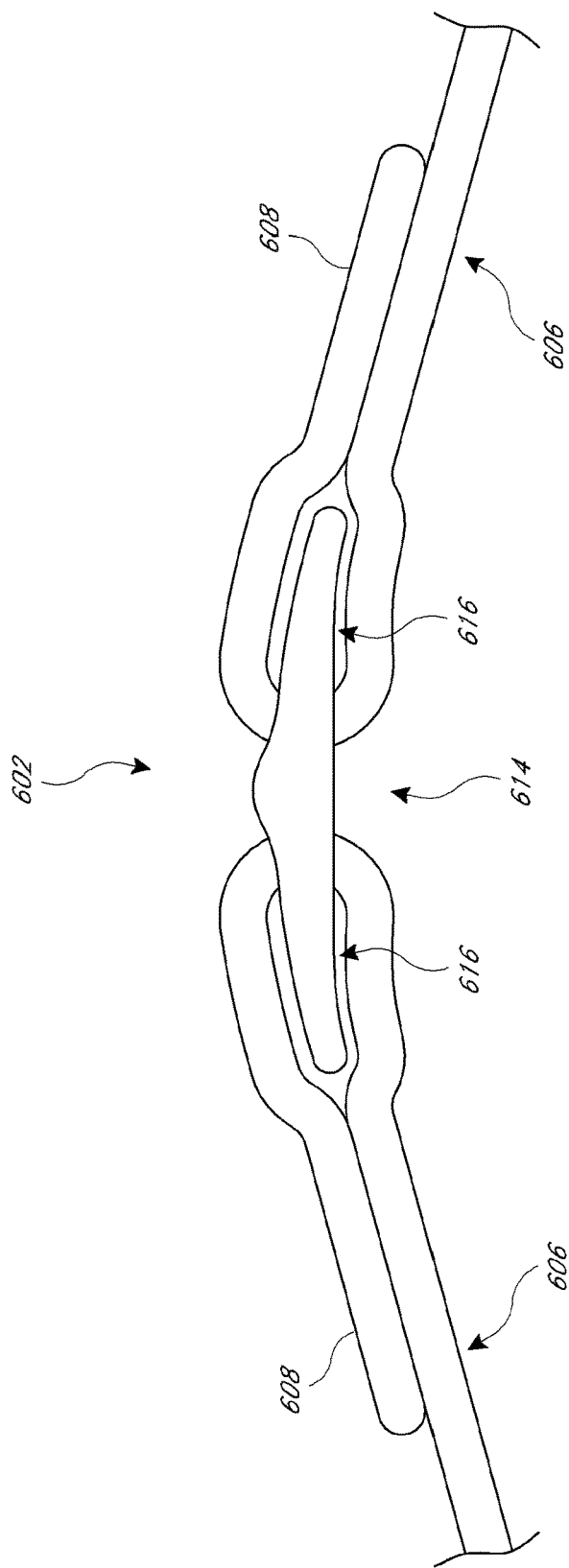
FIG. 60 is a portion of the headgear having the winged buckle connection.

With reference again to FIG. 61, the wings 616 have side walls 622 that taper inward. The inwardly tapering side walls 622 join to end walls 624 with rounded corners 626 in the illustrated configuration. The rounded corners 626 improve user comfort while the tapering side walls 622 reduce the width of the wings 616. The reduced width of at least the ends of the wings 616 facilitate capturing the wings 616 within the folded regions of the straps 606 underneath the ends 608, which is best shown in FIG. 59 and FIG. 60. In some configurations, the folded ends 608 and/or the adjoining portion of the straps 606 define a pocket that receives the tapering ends of the wings 616. In some configurations, the straps 606 can widen in a region as discussed above. In the illustrated configuration, the connector portion 614 of the buckle 602 is wider than at least a portion of the strap 606 such that the strap 606 can extend through the opening 612 defined in the connector portion 614 while the wings 616 taper such that the strap 606 can overlie and/or envelope the wings 616.

In some configurations, the wings 616 extend away from the connector portion 604 a length L2 that is greater than twice the thickness L1 of the wall of the connector portion 604 defining the slot 612. Other configurations also are possible. As discussed above, the extended length L2 of the wings 616 reduces flop over of the straps 606 when connected with the winged buckle 602. The wings 616 can have a length L2 that is less than a length of the connector portion of the ends 608 such that lateral extents 618 of the wings 616 can be enveloped by the connector portion of the ends 608.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. An elbow assembly configured to connect a mask assembly to an air conduit, the elbow assembly comprising:
    an elbow and a sleeve, the elbow comprising inner and outer walls and defining an air flow channel therebetween, the inner wall having an inner surface and an outer surface, the outer wall having an inner surface and an outer surface, the inner surface of the outer wall spaced from the outer surface of the inner wall and the air flow channel defined between the inner surface of the outer wall and the outer surface of the inner wall, the inner wall comprising a port in fluid communication with the air flow channel, the elbow having a frontmost surface facing away from a user in use, a rearmost surface facing toward the user in use, a first lateral side surface facing in a first lateral direction in use, and a second lateral side surface facing in a second lateral direction in use opposite the first direction, each of the first and second lateral side surfaces extending between the frontmost surface and the rearmost surface, the elbow comprising a first opening located in the first lateral side surface and a second opening located in the second lateral side surface, each of the first and second openings defined between the outer surface of the inner wall and a lateral edge of the outer wall, the sleeve being coupled with the elbow, wherein the frontmost surface is defined by the outer surface of the inner wall and the rearmost surface is defined by the outer surface of the outer wall; and
    a flap, wherein when the flap is at a first position, the flap at least partially blocks the port and allows gas from the air conduit to pass to the user via the elbow, and when the flap is at a second position, the flap at least partially blocks the air conduit thereby allowing gas to flow from the user through the port into the air flow channel and then to a location outside of the elbow, wherein the air flow channel directs air out of the lateral side surfaces of the elbow relative to the user and away from the user.

2. The elbow assembly of claim 1, wherein the air flow channel comprises two air flow channels.

3. The elbow assembly of claim 1, wherein the second opening is diametrically opposed to the first opening.

4. The elbow assembly of claim 1, wherein the frontmost surface extends across an entire width of the elbow.

5. The elbow assembly of claim 1, wherein the rearmost surface extends across an entire width of the elbow.

6. The elbow assembly of claim 1, wherein the first and second openings are located laterally outward of laterally-outermost extents of a flow channel through the elbow defined by the inner surface of the inner wall.

7. The elbow assembly of claim 1, wherein the first and second openings extend vertically along a length of the first and second lateral side surfaces.

8. The elbow assembly of claim 1, wherein the sleeve further comprises a bump extending around an outer surface of the sleeve and a recess adjacent to the bump.

9. The elbow assembly of claim 8, wherein the bump and the recess are adapted to receive a swiveling component incorporating a ridge to engage with the bump.

10. An elbow assembly configured to connect a mask assembly to an air conduit, the elbow assembly comprising:
    an elbow and a sleeve, the elbow comprising inner and outer walls and defining an air venting channel therebetween, the inner wall having an inner surface and an outer surface, the outer wall having an inner surface and an outer surface, the air venting channel defined between the inner surface of the outer wall and the outer surface of the inner wall, the inner surface of the inner wall defining a flow channel through the elbow from the air conduit to the mask assembly, the inner wall comprising a port located in a portion of the inner wall positioned toward a user and between the flow channel and the user in use, the air venting channel in fluid communication with the flow channel via the port, the sleeve being coupled with the elbow; and
    a flap, wherein when the flap is at a first position, the flap at least partially blocks the port and allows gas from the air conduit to pass to the user via the flow channel through the elbow, and when the flap is at a second position, the flap at least partially blocks the flow channel thereby allowing gas to flow from the user to a location outside of the elbow assembly via the port and the air venting channel,
    wherein during exhalation, gas flows from the flow channel toward the user through the port into the air venting channel, and changes direction from the port and flows out of the elbow assembly,
    wherein the air venting channel directs air away from the user.

11. The elbow assembly of claim 10, wherein the elbow comprises two openings at sides of the elbow that are in fluid communication with the air venting channel.

12. The elbow assembly of claim 10, wherein the elbow comprises a recess and the sleeve comprises a flange, the flange secured within the recess.

13. The elbow assembly of claim 10, wherein the flap extends into the flow channel from a base that is sandwiched between the elbow and the sleeve.

14. The elbow assembly of claim 10, wherein in the second position, the flap pivots downward into contact with the sleeve to obstruct the flow channel.

15. The elbow assembly of claim 10, wherein in the first position the flap at least partially or completely covers the port.

16. The elbow assembly of claim 10, wherein the port extends through a wall of the elbow that comprises a generally planar inner wall.

17. The elbow assembly of claim 10, wherein the elbow comprises one or more bias flow vent holes, wherein the bias flow vent holes are positioned in a forwardly directed orientation such that any bias flow does not directly impinge upon the user.

18. The elbow assembly of claim 10, wherein the sleeve further comprises at least one bump extending around an outer surface of the sleeve and at least one recess adjacent to the bump.

19. The elbow assembly of claim 18, wherein the bump and the recess are adapted to receive a swiveling component, the swiveling component comprising a ridge on an inner surface of the swiveling component configured to engage with the bump.

20. The elbow assembly claim 18, wherein the sleeve comprises two or more recesses.

21. The elbow assembly of claim 18, wherein the recess has a semicircular configuration and extends upward into the sleeve.

22. The elbow assembly of claim 18, wherein the sleeve comprises two or more bumps.

23. The elbow assembly of claim 18, wherein the at least one bump extends around an arc of about 70 degrees.

24. The elbow assembly of claim 18, wherein the at least one recess comprises at least two recesses and the at least one bump is generally centered between two recesses.

25. The elbow assembly of claim 10, wherein the elbow assembly comprises a swivel and a lever, the lever comprising a lower inwardly extending catch, and an upper portion of the swivel comprises a shoulder,
the catch securing the swivel in an axial position on the sleeve by engaging with the shoulder, and wherein when an upper portion of the lever is depressed, the catch moves away from the shoulder to allow the swivel to be removed from the sleeve.

26. The elbow assembly of claim 25, wherein the lever overlies the port such that the port is generally obscured from view.

27. The elbow assembly of claim 25, wherein the sleeve comprises a section that extends outward to connect to the lever.

28. The elbow assembly of claim 27, wherein the sleeve and the lever are integrally formed.

* * * * *